United States Patent
Burova et al.

(10) Patent No.: US 12,089,575 B2
(45) Date of Patent: *Sep. 17, 2024

(54) GENETICALLY MODIFIED MOUSE THAT EXPRESSES HUMANIZED PD1 AND PD-L1 PROTEINS

(71) Applicant: Regeneron Pharmaceuticals, Inc., Tarrytown, NY (US)

(72) Inventors: Elena Burova, Mount Kisco, NY (US); Yajun Tang, White Plains, NY (US); Ka-Man Venus Lai, Tarrytown, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 514 days.

This patent is subject to a terminal disclaimer.

(21) Appl. No.: 17/110,868

(22) Filed: Dec. 3, 2020

(65) Prior Publication Data

US 2021/0105983 A1    Apr. 15, 2021

Related U.S. Application Data

(63) Continuation of application No. 15/883,477, filed on Jan. 30, 2018, now Pat. No. 10,881,086, which is a continuation of application No. 14/963,402, filed on Dec. 9, 2015, now Pat. No. 9,913,461.

(60) Provisional application No. 62/106,525, filed on Jan. 22, 2015, provisional application No. 62/089,549, filed on Dec. 9, 2014.

(51) Int. Cl.
| | |
|---|---|
| *A01K 67/027* | (2024.01) |
| *A01K 67/0278* | (2024.01) |
| *A61K 49/00* | (2006.01) |
| *C07K 14/705* | (2006.01) |
| *C07K 16/30* | (2006.01) |
| *A61K 39/00* | (2006.01) |

(52) U.S. Cl.
CPC ...... *A01K 67/0278* (2013.01); *A61K 49/0008* (2013.01); *C07K 14/70596* (2013.01); *C07K 16/30* (2013.01); *A01K 2207/15* (2013.01); *A01K 2217/072* (2013.01); *A01K 2217/15* (2013.01); *A01K 2227/105* (2013.01); *A01K 2267/02* (2013.01); *A01K 2267/03* (2013.01); *A01K 2267/0331* (2013.01); *A61K 2039/505* (2013.01)

(58) Field of Classification Search
None
See application file for complete search history.

(56) References Cited

U.S. PATENT DOCUMENTS

| | | |
|---|---|---|
| 6,586,251 B2 | 7/2003 | Economides et al. |
| 7,432,059 B2 | 10/2008 | Freeman et al. |
| 7,488,802 B2 | 2/2009 | Collins et al. |
| 7,709,214 B2 | 5/2010 | Freeman et al. |
| 7,794,710 B2 | 9/2010 | Chen et al. |
| 7,892,540 B2 | 2/2011 | Chen et al. |
| 8,354,389 B2 | 1/2013 | Frendewey et al. |
| 8,383,796 B2 | 2/2013 | Korman et al. |
| 8,518,392 B2 | 8/2013 | Frendewey et al. |
| 8,574,872 B2 | 11/2013 | Minato et al. |
| 8,697,851 B2 | 4/2014 | Frendewey et al. |
| 8,741,295 B2 | 6/2014 | Olive |
| 8,779,108 B2 | 7/2014 | Queva et al. |
| 9,913,461 B2 * | 3/2018 | Burova ............ A61P 35/00 |
| 10,881,086 B2 * | 1/2021 | Burova ............ A01K 67/0278 |
| 2003/0177515 A1 | 9/2003 | Wu et al. |
| 2006/0179501 A1 | 8/2006 | Chan et al. |
| 2011/0251259 A1 | 10/2011 | DeFougerolles et al. |
| 2011/0268766 A1 | 11/2011 | Beech et al. |
| 2012/0263692 A1 | 10/2012 | Bertone et al. |
| 2013/0111616 A1 | 5/2013 | MacDonald et al. |
| 2013/0111617 A1 | 5/2013 | MacDonald et al. |
| 2013/0117873 A1 | 5/2013 | Wang et al. |
| 2013/0122014 A1 | 5/2013 | Korman et al. |
| 2013/0291136 A1 | 10/2013 | Freeman et al. |
| 2014/0047572 A1 | 2/2014 | Chen et al. |
| 2014/0134662 A1 | 5/2014 | Flavell et al. |
| 2014/0235933 A1 | 8/2014 | Lee et al. |
| 2014/0245466 A1 | 8/2014 | MacDonald et al. |
| 2014/0245467 A1 | 8/2014 | MacDonald et al. |

(Continued)

FOREIGN PATENT DOCUMENTS

| | | |
|---|---|---|
| CN | 102292445 A | 12/2011 |
| CN | 102762590 A | 10/2012 |

(Continued)

OTHER PUBLICATIONS

Description of Pdcd1 Mus musculus, 2023.*
Wikipedia definition of "locus", 2023.*
National Human Genome Res. Institute defintion of "locus", 2023.*
Tong C. et al., "Generating Gene Knockout Rats by Homologous Recombination in Embryonic Stem Cells", Nat. Protoc. 6(6):doi:10.1038/nprot.2011.338 (Jun. 2011).
Tong C. et al., "Production of p53 Gene Knockout Rats by Homologous Recombination in Embryonic Stem Cells", Nature 467:211-215 (Sep. 9, 2010).

(Continued)

*Primary Examiner* — Michael C Wilson
(74) *Attorney, Agent, or Firm* — Scully, Scott, Murphy & Presser, P.C.; Casey Donahoe

(57) ABSTRACT

Non-human animals, methods and compositions for making and using the same, are provided, wherein said non-human animals comprise a humanization of a Cluster of Differentiation 274 (CD274) gene. Such non-human animals may be described, in some embodiments, as having a genetic modification to an endogenous CD274 gene so that said non-human animals express a Programmed cell death ligand 1 (PD-L) polypeptide that includes a human portion and an endogenous portion (e.g., a non-human portion).

7 Claims, 20 Drawing Sheets

Specification includes a Sequence Listing.

(56) References Cited

U.S. PATENT DOCUMENTS

| | | |
|---|---|---|
| 2014/0309487 A1 | 10/2014 | Lee et al. |
| 2014/0310828 A1 | 10/2014 | Lee et al. |
| 2015/0089678 A1 | 3/2015 | Murphy et al. |
| 2015/0143558 A1 | 5/2015 | McWhirter et al. |
| 2015/0282463 A1 | 10/2015 | Murphy et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0366174 A1 | 12/2015 | Burova et al. |
| 2016/0157469 A1 | 6/2016 | Burova et al. |
| 2016/0345549 A1 | 12/2016 | Gurer et al. |
| 2017/0142943 A1 | 5/2017 | Mujica et al. |
| 2017/0164588 A1 | 6/2017 | Olson et al. |
| 2018/0160663 A1 | 6/2018 | Burova et al. |

FOREIGN PATENT DOCUMENTS

| | | |
|---|---|---|
| CN | 102782148 A | 11/2012 |
| CN | 103242448 A | 8/2013 |
| CN | 103251952 A | 8/2013 |
| CN | 104039132 A | 9/2014 |
| EP | 1 297 135 B1 | 4/2003 |
| EP | 1 537 878 A1 | 6/2005 |
| JP | 2012-50451 A | 3/2012 |
| JP | 2014-532412 A | 12/2014 |
| RU | 2 425 880 C2 | 8/2011 |
| WO | 97/07668 A1 | 3/1997 |
| WO | 97/07669 A1 | 3/1997 |
| WO | 02/00692 A2 | 1/2002 |
| WO | 2004/004771 A1 | 1/2004 |
| WO | 2005/060739 A1 | 7/2005 |
| WO | 2007/005874 A2 | 1/2007 |
| WO | 2011/044050 A2 | 4/2011 |
| WO | 2011/066389 A1 | 6/2011 |
| WO | 2012/112544 A2 | 8/2012 |
| WO | 2013/063346 A1 | 5/2013 |
| WO | 2013/078230 A1 | 5/2013 |
| WO | 2013/079174 A1 | 6/2013 |
| WO | 2014/022758 A1 | 2/2014 |
| WO | 2014/031610 A1 | 2/2014 |
| WO | 2014/039782 A2 | 3/2014 |
| WO | 2014/116846 A2 | 7/2014 |
| WO | 2014/130667 A1 | 8/2014 |
| WO | 2014/130671 A1 | 8/2014 |
| WO | 2014/130706 A1 | 8/2014 |
| WO | 2014/172489 A2 | 10/2014 |
| WO | 2014/197369 A1 | 12/2014 |
| WO | 2015/112805 A1 | 7/2015 |
| WO | 2015/196051 A1 | 12/2015 |
| WO | 2016/085889 A1 | 6/2016 |
| WO | 2018/041118 A1 | 3/2018 |

OTHER PUBLICATIONS

Zhou H. et al., "Developing tTA Transgenic Rats for Inducible and Reversible Gene Expression", International Journal of Biological Sciences 5(2):171-181 (2009).

Russian Office Action and Search Report dated Jun. 24, 2019 received in Russian Patent Application No. 2017123754, together with an English-language translation.

Japanese Final Office Action dated Jun. 3, 2020 received in Japanese Patent Application No. 2017-530591, together with an English-language translation.

Japanese Notice of Reasons for Rejection dated Oct. 7, 2019 received in Japanese Patent Application No. 2017-530591, together with an English-language translation.

Chinese Office Action dated Mar. 4, 2020 received in Chinese Patent Application No. 201580067025.6, together with an English-language translation.

European Examination Report dated Dec. 20, 2018 received in European Patent Application No. 15 816 631.4.

Krzywinski M. et al., "Integrated and Sequence-Ordered BAC-and YAC-Based Physical Maps for the Rat Genome", *Genome Research* 14:766-779 (Apr. 2004).

Ma Y. et al., "Building Cre Knockin Rat Lines Using CRISPR/Cas9", Methods in Molecular Biology 1642:37-52 (2017).

Ma Y. et al., "CRISPR/Cas9-Mediated Targeting of the Rosa26 Locus Produces Cre Reporter Rat Strains for Monitoring Cre-LoxP-Mediated Lineage Tracing", *The FEBS Journal* 284:3262-3277 (2017).

Ma Y. E al., "Generating Rats With Conditional Alleles Using CRISPR/Cas9", Cell Research 24:122-125 (2014).

Ma Y. et al., "Heritable Multiplex Genetic Engineering in Rats Using CRISPR/Cas9", PLoS One 9(3):e89413 (Mar. 2014).

Ma Y. et al., Generation of eGFP and Cre Knockin Rats by CRISPR/Cas9? The FEBS Journal 281:3779-3790.

Osoegawa K. et al., "BAC Resources for the Rat Genome Project", Genome Research 14:780-785 (Apr. 2004).

Pakula A.A., "Genetic Analysis of Protein Stability and Function", Annu. Rev. Genet. 23:289-310 (1989).

Paris D.B.B.P. et al., "Equine Embryos and Embryonic Stem Cells: Defining Reliable Markers of Pluripotency", Theriogenology 74:516-524 (2010).

Rybchin V.N., "Fundamentals of Genetic Engineering", Textbook for High Schools, Saint-Petersburg, Publishing House SPbSTU 522:411-413 (2002).

Genbank Accession No. NM_001163412.1 (2 pages) (Dec. 24, 2015).

Genbank Accession No. NP_001156884.1 (2 pages) (Dec. 24, 2015).

Genbank Accession No. XM_541302.3 (1 page) (Dec. 2, 2011).

Genbank Accession No. NM_001083889.1 (2 pages) (Dec. 27, 2015).

Genbank Accession No. NP_001077358.1 (2 pages) (Dec. 27, 2015).

Genbank Accession No. NM_001191954.1 (2 pages) (Dec. 25, 2015).

Genbank Accession No. NP_001178883.1 (2 pages) (Dec. 25, 2015).

PD-L1 Definition, Wikipedia (4 pages) (2016).

Brevini T.A.L. et al., "No Shortcuts to Pig Embryonic Stem Cells", Theriogenology 74:544-550 (2010).

Cao S. et al., "Isolation and Culture of Primary Bovine Embryonic Stem Cell Colonies by a Novel Method", Journal of Experimental Zoology 311A:368-376 (2009).

Barber D.L. et al., "Restoring Function in Exhausted CD8 T Cells During Chronic Viral Infection", Nature 439:682-687 (Feb. 9, 2006).

Burova E. et al., "Abstract 266: Antitumor Activity of REGN2810, a Fully Human Anti-PD-1 Monoclonal Anitbody, Against MC38. Ova Tumors Grown in Immune-Competent Humanized PD-1 Mice", Cancer Research 75:266 (2 pages total) (Apr. 18, 2015).

Butte M.J. et al., "PD-L1 Interacts Specifically with B7-1 to Inhibit T Cell Proliferation", Immunity 27(1):111-122 (Jul. 2007).

Cao Y. et al., "B7-H1 Overexpression Regulates Epithelial-Mesenchymal Transition and Accelerates Carcinogenesis in Skin", Cancer Research 71(4):1235-1243 (2010).

Cao Y. et al., "Immunoregulatory Molecule B7-H1 (CD274) Contributes to Skin Carcinogenesis", Cancer Research 71(14):4737-4741 (Jul. 15, 2011).

Carter L.L. et al., "PD-1/PD-L1, But Not PD-1/PD-L2, Interactions Regulate the Severity of Experimental Autoimmune Encephalomyelitis", Journal of Neuroimmunology 182:124-134 (2007).

Devoy A. et al., "Genomically Humanized Mice: Technologies and Promises", Nature Reviews Genetics 13:14-20 (Jan. 2012).

Ding Q. et al., "Human PD-L1-Overexpressing Porcine Vascular Endothelial Cells Induce Functionally Suppressive Human CD4+CD25hiFoxp3+ Treg Cells", Journal of Leukocyte Biology 90:77-86 (Jul. 2011).

Dong H. et al., "Costimulating Aberrant T Cell Responses by B7-H1 Autoantibodies in Rheumatoid Arthritis", The Journal of Clinical Investigation 111(3):363-370 (Feb. 2003).

Dong H. et al., "B7-H1, a Third Member of the B7 Family, Co-Stimulates T-Cell Proliferation and Interleukin-10 Secretion", Nature Medicine 5(12):1365-1369 (Dec. 1999).

(56) References Cited

OTHER PUBLICATIONS

Durgan K. et al., "Targeting NKT Cells and PD-L1 Pathway Results in Augmented Anti-Tumor Responses in a Melanoma Model", Cancer Immunol Immunother. 60(4):547-558 (Apr. 2011).
Freeman G.J. et al., "Engagement of the PD-1 Immunoinhibitory Receptor by a Novel B7 Family Member Leads to Negative Regulation of Lymphocyte Activation", J. Exp. Med. 192(7):1027-1034 (Oct. 2, 2000).
Garanto A. et al., "Unexpected CEP290 mRNA Splicing in a Humanized Knock-In Mouse Model for Leber Congenital Amaurosis", PLOS One 8(11):e79369 (Nov. 2013).
Ghazizadeh S. et al., "Distinct Strategies are Required to Suppress Antigen-Specific Responses to Genetically Modified Keratinocytes and Fibroblasts", Molecular Therapy 20(1):196-203 (Jan. 2012).
Guleria I. et al., "A Critical Role for the Programmed Death Ligand 1 in Fetomaternal Tolerance", J. Exp. Med. 202 (2):231-237 (Jul. 18, 2005).
He X-H et al., "Identification of a Novel Splice Variant of Human PD-L1 mRNA Encoding as Isoform-Lacking Igv-Like Domain", Acta Pharmacologica Sinica 26(4):462-468 (Apr. 2005).
Iwai Y. et al., "Involvement of PD-L1 on Tumor Cells in the Escape from Host Immune System and Tumor Immunotherapy by PD-L1 Blockade", PNAS 99(19):12293-12297 (Sep. 17, 2002).
Kawaharada K. et al., "Rat Embryonic Stem Cells Create New Era in Development of Genetically Manipuated Rat Models", World Journal of Stem Cells 7(7):1054-1063 (Aug. 26, 2015).
Keir M.E. et al., "PD-1 and its Ligands in Tolerance and Immunity", Annu. Rev. Immunol. 26:677-704 (2008).
Keir M.E. et al., "PD-1 Regulates Self-Reactive CD8+ T Cell Responses to Antigen in Lymph Nodes and Tissues", The Journal of Immunology 179:5064-5070 (2007).
Keir M.E. et al., "Tissue Expression of PD-L1 Mediates Peripheral T Cell Tolerance", J. Exp. Med. 203(4):883-895 (Apr. 17, 2006).
Keir M.E. et al., "Programmed Death-1 (PD-1):PD-Ligand 1 Interactions Inhibit TCR-Mediated Positive Selection of Thymocytes", The Journal of Immunology 175:7372-7379 (2005).
Kuipers H. et al., "Contribution of the PD-1 Ligands/PD-1 Signaling Pathway to Dendritic Cell-Mediated CD4+ T Cell Activation", European Journal of Immunology 36:2472-2482 (2006).
Lakso M. et al., "Targeted Oncogene Activation by Site-Specific Recombination in Transgenic Mice", Proc. Natl. Acad. Sci. USA 89:6232-6236 (Jul. 1992).
Latchman Y.E. et al., "PD-L1-Deficient Mice Show that PD-L1 on T Cells, Antigen-Presenting Cells, and Host Tissues Negatively Regulates T Cells", PNAS 101(29):10691-10696 (Jul. 20, 2014).
Lee S-J et al., "Interferon Regulatory Factor-1 is Prerequisite to the Constitutive Expression and IFN-γ-Induced Upregulation of B7-H1 (CD274)", FEBS Letters 580:755-762 (2006).
Liu X. et al., "B7DC/PDL2 Promotes Tumor Immunity by a PD-1-Independent Mechanism", The Journal of Experimental Medicine 197(12):1721-1730 (Jun. 16, 2003).
Matsumoto K. et al., "B7-DC Regulates Asthmatic Response by an IFN-γ-Dependent Mechanism", The Journal of Immunology 172:2530-2541 (2004).
O'gorman S. et al., "Rocombinase-Mediated Gene Activation and Site-Specific Integration in Mammalian Cells", Science 251:1351-1355 (Mar. 15, 1991).
Ostrand-Rosenberg S. et al., "The Programmed Death-1 Immune Suppressive Pathway: Barrier to Anti-Tumor Immunity", The Journal of Immunology 193(8):3835-3841 (Oct. 15, 2014).
Paterson A.M. et al., "The PD-L1:B7-1 Pathway Restrains Diabetogenic Effector T Cells In Vivo", The Journal of Immunology 187(3):1097-1105 (Aug. 1, 2011).
Pedoeem A. et al., "Programmed Death-1 Pathway in Cancer and Autoimmunity", Clinical Immunology 153:145-152 (2014).
Philips G.K. et al., "Therapeutic Uses of Anti-PD-1 and Anti-PD-L1 Antibodies", International Immunology 27(1):39-46 (2014).
Plege A. et al., "Suppression of Human T-Cell Activation and Expansion of Regulatory T Cells by Pig Cells Overexpression PD-Ligands", Transplantation 87(7):975-982 (Apr. 15, 2009).
Plege A. et al., "Downregulation of Cytolytic Activity of Human Effector Cells by Transgenic Expression of Human PD-Ligand-1 on Porcine Target Cells", European Society for Organ Transplantation 23:1293-1300 (2010).
Ritprajak P. et al., "Keratinocyte-Associated B7-H1 Directly Regulates Cutaneous Effector CD8+ T Cell Responses", The Journal of Immunology 1844918-4925 (2010).
Rongvaux A. et al., "Human Thrombopoietin Knockin Mice Efficiently Support Human Hematopoiesis In Vivo", PNAS 108(6):2378-2383 (Feb. 8, 2011).
Seo S-K et al., "Blockade of Endogenous B7-H1 Suppresses Antibacterial Protection After Primary Listeria Monocytogenes Infection", Immunology 123:90-99 (2007).
Shin T. et al., "In Vivo Costimulatory Role of B7-DC in Tuning T Helper Cell 1 and Cytotoxic T Lymphocyte Responses", The Journal of Experimental Medicine 201(10):1531-1541 (May 16, 2005).
Subudhi S.K. et al., "Local Expression of B7-H1 Promotes Organ-Specific Autoimmunity and Transplant Rejection", The Journal of Clinical Investigation 113(5):694-700 (Mar. 2004).
Tanaka K. et al., "PDL1 is Required for Peripheral Transplantation Tolerance and Protection from Chronic Allograft Rejection", J. Immunol. 179(8):5204-5210 (Oct. 15, 2007).
Tang L. et al., "Establishment of PD-L1 Transgenic Mouse Model and Recovery of the Motor Function After Spinal Cord Injury", ChinJ. Cell Mol Immunol. 27(4):357-359 (2011), together with an English-language abstract.
Valenzuela D.M. et al., "High-Throughput Engineering of the Mouse Genome Coupled with High-Resolution Expression Analysis", Nature Biotechnology 21(6):652-659 (Jun. 2003).
Wang X.F. et al., "PD-1/PDL1 and CD28/CD80 Pathways Modulate Natural Killer T Cell Function to Inhibit Hepatitis B Virus Replication", Journal of Viral Hepatitis 20(Suppl 1):27-39 (2013).
Wang C-J et al., "Protective Role of Programmed Death 1 Ligand 1 (PD-L1) in Nonobese Diabetic Mice", Diabetes 67:1861-1869 (Jul. 2008).
Wen X. et al., "Transplantation of NIT-1 Cells Expression pD-L1 for Treatment of Streptozotocin-Induced Diabetes", Transplantation 86(11):1596-1602 (Dec. 15, 2008).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).
Willinger T. et al., "Improving Human Hemato-Lymphoid-System Mice by Cytokine Knock-in Gene Replacement", Trends in Immunology 32(7):321-327 (Jul. 2011).
Wilmut I. et al., "Viable Offspring Derived from Fetal and Adult Mammalian Cells", Nature 385:810-813 (Feb. 27, 1997).
Yang W. et al., "Increased Expression of Programmed Death (PD)-1 and its Ligand PD-L1 Correlates With Impaired Cell-Mediated Immunity in High-Risk Human Papillomavirus-Related Cervical Intraepithelial Neoplasia", Immunology 139:513-522 (2013).
Yantha J. et al., "Unexpected Acceleration of Type 1 Diabetes by Transgenic Expression of B7-H1 in NOD Mouse Peri-Islet Glia", Diabetes 59:2588-2596 (Oct. 2010).
International Search Report and Written Opinion dated Mar. 30, 2016 received in International Application No. PCT/US2015/064626.
Genbank Accession No. NM_001267706.1 (5 pages) (Sep. 25, 2015).
Genbank Accession No. NP_001254635.1 (3 pages) (Sep. 25, 2015).
Genbank Accession No. XM_006716759.1 (2 pages) (Feb. 3, 2014).
Genbank Accession No. XP_006716822.1 (1 page) (Mar. 12, 2015).
Genbank Accession No. XM_424811.3 (2 pages) (Dec. 16, 2011).
Genbank Accession No. XP_424811.3 (1 page) (Dec. 16, 2011).
Genbank Accession No. XM_001140705.2 (3 pages) (Oct. 25, 2012).
Genbank Accession No. XP_001140705.1 (2 pages) (Oct. 8, 2014).
Dennis Jr. M.B., "Welfare Issues of Genetically Modified Animals", ILAR Journal 43(2):100-109 (2002).
Frankel A.E. et al., "Characterization of Diphtheria Fusion Proteins Targeted to the Human Interleukin-3 Receptor", Protein Engineering 13(8):575-581 (2000).

(56) References Cited

OTHER PUBLICATIONS

Gibbs R.A. et al., "Genome Sequence of the Brown Norway Rat Yields Insights into Mammalian Evolution", Nature 482:493-521 (Apr. 1, 2004).
Glick B. et al., Moleculyarnaya Biotehnologiya. Printsipy i primeneniye. Moscow: Mir, 2002, together with an English-language translation.
Harari D. et al., "Bridging the Species Divide: Transgenic Mice Humanized for Type-I Interferon Response", *PLoS ONE* 9(1):e84259, XP055553720. DOI:10.1371/journal.pone.0084259 (Jan. 9, 2014).
Hofker M.H. et al., "Transgenic Mouse Methods and Protocols", Methods in Molecular Biology 209:51-58 (2002-2003).
Houdebine L-M, "Methods to Generate Transgenic Animais", Genetic Engineering in Livestock, New Applications and Interdisciplinary Perspectives, Engelhard M. et al., XVI, 1 46, p. 8, illu. pp. 31-47 (2009).
Hu X. et al., "Heritable Gene-Targeting With gRNA/Cas9 in Rats", Cell Research 23:1322-1325 (2013).
Li W. et al., "Simultaneous Generation and Germline Transmission of Multiple Gene Mutations in Rat Using CRISPR-Cas Systems", *Nature Biotechnology* 31(8):684-686 (Aug. 2013).
Li W. et al., "Heritable Gene Targeting in the Mouse and Rat Using a CRISPR-Cas System", Nature Biotechnology 31(8):681-683 (Aug. 2013).

\* cited by examiner

Figure 6

Mouse CD274 mRNA (NM_021893.3)
GAAATCGTGGTCCCCAAGCCTCATGCCAGGCTGCACTTGCACGTCGCGGGCCAGTCTCCTCGCCTG
CAGATAGTTCCCAAAACATGAGGATATTTGCTGGCATTATATTCACAGCCTGCTGTCACTTGCT
ACGGGCGTTTACTATCACGGCTCCAAAGGACTTGTACGTGGTGGAGTATGGCAGCAACGTCA
CGATGGAGTGCAGATTCCCTGTAGAACGGGAGCTGGACCTGCTTGCGTTAGTGGTGTACTGG
GAAAAGGAAGATGAGCAAGTGATTCAGTTTGTGGCAGGAGAGGAGGACCTTAAGCCTCAGCA
CAGCAACTTCAGGGGGAGAGCCTCGCTGCCAAAGGACCAGCTTTTGAAGGGAAATGCTGCCC
TTCAGATCACAGACGTCAAGCTGCAGGACGCAGGCGTTTACTGCTGCATAATCAGCTACGGT
GGTGCGGACTACAAGCGAATCACGCTGAAAGTCAATGCCCCATACCGCAAAATCAACCAGAG
AATTTCCGTGGATCCAGCCACTTCTGAGCATGAACTAATATGTCAGGCCGAGGGTTATCAG
AAGCTGAGGTAATCTGGACAAACAGTGACCACCAACCCGTGAGTGGGAAGAGAAGTGTCACC
ACTTCCCGGACAGAGGGGATGCTTCTCAATGTGACCAGCAGTCTGAGGGTCAACGCCACAGC
GAATGATGTTTCTACTGTACGTTTGGAGATCACAGCCAGGGCAAAACCACACAGCGGAGC
TGATCATCCCAGAACTGCCTGCAACACATCCTCCACAGAACAGGACTCACTGGGTGCTTCTG
GGATCCATCCTGTTGTTCCTCATTGTAGTGTCCACGGTCCTCCTCTTCTTGAGAAAACAAGTG
AGAATGCTAGATGTGGAGAAATGTGGCGTTGAAGATACAAGCTCAAAAAACCGAAATGATAC
ACAATTCGAGGAGACGTAAGCAGTGTTAACCCTCTGATCGTCGATTGGCAGCTTGTGGTCTGTG
AAAGAAAGGGCCCATGGGACATGAGTCCAAAGACTCAAGATGGAACCTGAGGGAGAGAACCAAG
AAAGTGTTGGGAGAGGAGCCTGGAACAACGGACATTTTTCCAGGGAGACACTGCTAAGCAAGTT
GCCCATCAGTCGTCTTGGGAAATGGATTGAGGGTTCCTGGCTTAGCAGCTGGTCCTTGCACAGTGA
CCTTTTCCTCTGCTCAGTGCCGGGATGAGAGATGGAGTCATGAGTGTTGAAGAATAAGTGCCTTCT
ATTTATTTTGAGTCTGTGTGTTCTCACTTTGGGCATGTAATTATGACTGGTGAATTCTGACGACATG
ATAGATCTTAAGATGTAGTCACCAAACTCAACTGCTGCTTAGCATCCTCCGTAACTACTGATACAA
GCAGGGAACACAGAGGTCACCTGCTTGGTTTGACAGGCTCTTGCTGTCTGACTCAAATAATCTTTAT
TTTTCAGTCCTCAAGGCTCTTCGATAGCAGTTGTTCTGTATCAGCCTTATAGGTGTCAGGTATAGCA
CTCAACATCTCATCTCATTACAATAGCAACCCTCATCACCATAGCAACAGCTAACCTCTGTTATCCT
CACTTCATAGCCAGGAAGCTGAGCGACTAAGTCACTTGCCCACAGAGTATCAGCTCTCAGATTTCT
GTTCTTCAGCCACTGTCCTTTCAGGATAGAATTTGTCGTTAAGAAATTAATTTAAAAACTGATTATT
GAGTAGCATTGTATATCAATCACAACATGCCTTGTGCACTGTGCTGGCCTCTGAGCATAAAGATGT
ACGCCGGAGTACCGGTCGGACATGTTTATGTGTGTTAAATACTCAGAGAAATGTTCATTAACAAGG
AGCTTGCATTTTAGAGACACTGGAAAGTAACTCCAGTTCATTGTCTAGCATTACATTTACCTCATTT
GCTATCCTTGCCATACAGTCTCTTGTTCTCCATGAAGTGTCATGAATCTTGTTGAATAGTTCTTTTAT
TTTTTAAATGTTTCTATTTAAATGATATTGACATCTGAGGCGATAGCTCAGTTGGTAAAACCCTTTC
CTCACAAGTGTGAAACCCTGAGTCTTATCCCTAGAACCCACATAAAAAACAGTTGCGTATGTTTGT
GCATGCTTTTGATCCCAGCACTAGGGAGGCAGAGGCAGGCAGATCCTGAGCTCTCATTGACCACCC
AGCCTAGCCTACATGGTTAGCTCCAGGCCTACAGGAGCTGGCAGAGCCTGAAAAACGATGCCTAG
ACACACACACACACACACACACACACACACACACACACACCATGTACTCATAGACCTAAGT
GCACCCTCCTACACATGCACACACATACAATTCAAACACAAATCAACAGGGAATTGTCTCAGAATG
GTCCCCAAGACAAAGAAGAAGAAAAACACCAAACCAGCTCTATTCCCTCAGCCTATCCTCTCTACT
CCTTCCTAGAAGCAACTACTATTGTTTTTGTATATAAATTTACCCAACGACAGTTAATATGTAGAAT
ATATATTAAAGTGTCTGTCAATATATATTATCTCTTTCTTTCTTCCTTTCTTTCTTTCTTTCTTTC
TTTCTTTCTTTCTTTCTTTCTTTCTTCCTTCCTTCCTTCCTTCCTTCCTTCCTTCCTTTCTTT
CTTTCTTTCTTTTTTCTGTCTATCTGTACCTAAATGGTTGCTCACTATGCATTTCTGTGCTCTTCGC
CCTTTTTATTTAATGTATGGATATTTATGCTGCTTCCAGAATGGATCTAAAGCTCTTTGTTTCTAGGT
TTTCTCCCCATCCTTCTAGGCATCTCTCACACTGTCTAGGCCAGACACCATGTCTGCTGCCTGAAT
CTGTAGACACCATTTATAAAGCACGTACTCACCGAGTTTGTATTTGGCTTGTTCTGTGTCTGATTAA
AGGGAGACCATGAGTCCCCAGGGTACACTGAGTTACCCAGTACCAAGGGGGAGCCTTGTTTGTGT
CTCCATGGCAGAAGCAGGCCTGGAGCCATTTTGGTTTCTTCCTTGACTTCTCTCAAACACAGACGCC
TCACTTGCTCATTACAGGTTCTCCTTTGGGAATGTCAGCATTGCTCCTTGACTGCTGGCTGCCCTGG
AAGGAGCCCATTAGCTCTGTGTGAGCCCTTGACAGCTACTGCCTCTCCTTACCACAGGGGCCTCTA
AGATACTGTTACCTAGAGGTCTTGAGGATCTGTGTTCTCTGGGGGGAGGAAAGGAGGAGGAACCC
AGAACTTTCTTACAGTTTTCCTTGTTCTGTCACATGTCAAGACTGAAGGAACAGGCTGGGCTACGTA

Figure 6 (continued)

GTGAGATCCTGTCTCAAAGGAAAGACGAGCATAGCCGAACCCCCGGTGGAACCCCCTCTGTTACCT
GTTCACACAAGCTTATTGATGAGTCTCATGTTAATGTCTTGTTTGTATGAAGTTTAAGAAAATATCG
GGTTGGGCAACACATTCTATTTATTCATTTTATTTGAAATCTTAATGCCATCTCATGGTGTTGGATTG
GTGTGGCACTTTATTCTTTTGTGTTGTGTATAACCATAAATTTTATTTTGCATCAGATTGTCAATGTA
TTGCATTAATTTAATAAATATTTTATTTATTAAAAAAAAAAAAAAAAAA (SEQ ID NO:1)

Mouse PD-L1 amino acid (Q9EP73)
<u>MRIFAGIIFTACCHLLRA</u>(FTITAPKDLYVVEYGSNVTMECRFPVERELDLLALVVYWEKEDEQVIQ
FVAGEEDLKPQHSNFRGRASLPKDQLLKGNAALQITDVKLQDAGVYCCIISYGGADYKRIT)LKVN
APYRKINQRISVDPATSEHELICQAEGYPEAEVIWTNSDHQPVSGKRSVTTSRTEGMLLNVTSSLR
VNATANDVFYCTFWRSQPGQNHTAELIIPELPATHPPQNRTH<u>WVLLGSILLFLIVVSTVLLFLRKQVR</u>
<u>MLDVEKCGVEDTSSKNRNDTQFEET</u> (SEQ ID NO:2)

Human CD274 mRNA (NM_014143.3)
GGCGCAACGCTGAGCAGCTGGCGCGTCCCGCGCGGCCCCAGTTCTGCGCAGCTTCCCGAGGCTCCG
CACCAGCCGCGCTTCTGTCCGCCTGCAG<u>GGCATTCCAGAAAGATGAGGATATTTGCTGTCTTTAT</u>
<u>ATTCATGACCTACTGGCATTTGCTGAACG</u>CATTTACTGTCACGGTTCCCAAGGACCTATATGT
GGTAGAGTATGGTAGCAATATGACAATTGAATGCAAATTCCCAGTAGAAAAACAATTAGACC
TGGCTGCACTAATTGTCTATTGGGAAATGGAGGATAAGAACATTATTCAATTTGTGCATGGAG
AGGAAGACCTGAAGGTTCAGCATAGTAGCTACAGACAGAGGGCCCGGCTGTTGAAGGACCA
GCTCTCCCTGGGAAATGCTGCACTTCAGATCACAGATGTGAAATTGCAGGATGCAGGGGTGT
ACCGCTGCATGATCAGCTATGGTGGTGCCGACTACAAGCGAATTACTGTGAAAGTCAATG<u>CC</u>
<u>CCATACAACAAAATCAACCAAAGAATTTTGGTTGTGGATCCAGTCACCTCTGAACATGAACTG</u>
<u>ACATGTCAGGCTGAGGGCTACCCCAAGGCCGAAGTCATCTGGACAAGCAGTGACCATCAAGT</u>
<u>CCTGAGTGGTAAGACCACCACCACCAATTCCAAGAGAGAGGAGAAGCTTTTCAATGTGACCA</u>
<u>GCACACTGAGAATCAACACAACAACTAATGAGATTTTCTACTGCACTTTTAGGAGATTAGATC</u>
<u>CTGAGGAAAACCATACAGCTGAATTGGTCATCCCAG</u>AACTACCTCTGGCACATCCTCCAAAT
GAAAGGACTCACTTGGTAATTCTGGGAGCCATCTTATTATGCCTTGGTGTAGCACTGACATTC
ATCTTCCGTTTAAGAAAGGGAGAATGATGGATGTGAAAAATGTGGCATCCAAGATACAAA
<u>CTCAAAGAAGCAAAGTGA</u>TACACATTTGGAGGAGACGTAATCCAGCATTGGAACTTCTGATCTT
CAAGCAGGGATTCTCAACCTGTGGTTTAGGGGTTCATCGGGGCTGAGCGTGACAAGAGGAAGGAA
TGGGCCCGTGGGATGCAGGCAATGTGGGACTTAAAAGGCCCAAGCACTGAAAATGGAACCTGGCG
AAAGCAGAGGAGGAGAATGAAGAAAGATGGAGTCAAACAGGGAGCCTGGAGGGAGACCTTGATA
CTTTCAAATGCCTGAGGGGCTCATCGACGCCTGTGACAGGGAGAAAGGATACTTCTGAACAAGGA
GCCTCCAAGCAAATCATCCATTGCTCATCCTAGGAAGACGGGTTGAGAATCCCTAATTTGAGGGTC
AGTTCCTGCAGAAGTGCCCTTTGCCTCCACTCAATGCCTCAATTTGTTTTCTGCATGACTGAGAGTC
TCAGTGTTGGAACGGGACAGTATTTATGTATGAGTTTTTCCTATTTATTTTGAGTCTGTGAGGTCTTC
TTGTCATGTGAGTGTGGTTGTGAATGATTTCTTTTGAAGATATATTGTAGTAGATGTTACAATTTTG
TCGCCAAACTAAACTTGCTGCTTAATGATTTGCTCACATCTAGTAAAACATGGAGTATTTGTAAGGT
GCTTGGTCTCCTCTATAACTACAAGTATACATTGGAAGCATAAAGATCAAACCGTTGGTTGCATAG
GATGTCACCTTTATTTAACCCATTAATACTCTGGTTGACCTAATCTTATTCTCAGACCTCAAGTGTCT
GTGCAGTATCTGTTCCATTTAAATATCAGCTTTACAATTATGTGGTAGCCTACACACATAATCTCAT
TTCATCGCTGTAACCACCCTGTTGTGATAACCACTATTATTTTACCCATCGTACAGCTGAGGAAGCA
AACAGATTAAGTAACTTGCCCAAACCAGTAAATAGCAGACCTCAGACTGCCACCCACTGTCCTTTT
ATAATACAATTTACAGCTATATTTTACTTTAAGCAATTCTTTTATTCAAAAACCATTTATTAAGTGC
CCTTGCAATATCAATCGCTGTGCCAGGCATTGAATCTACAGATGTGAGCAAGACAAAGTACCTGTC
CTCAAGGAGCTCATAGTATAATGAGGAGATTAACAAGAAAATGTATTATTACAATTTAGTCCAGTG
TCATAGCATAAGGATGATGCGAGGGGAAAACCCGAGCAGTGTTGCCAAGAGGAGGAAATAGGCCA
ATGTGGTCTGGGACGGTTGGATATACTTAAACATCTTAATAATCAGAGTAATTTTCATTTACAAAG
AGAGGTCGGTACTTAAAATAACCCTGAAAAATAACACTGGAATTCCTTTTCTAGCATTATATTTATT
CCTGATTTGCCTTTGCCATATAATCTAATGCTTGTTTATATAGTGTCTGGTATTGTTTAACAGTTCTG
TCTTTTCTATTTAAATGCCACTAAATTTTAAATTCATACCTTTCCATGATTCAAAATTCAAAAGATCC
CATGGGAGATGGTTGGAAAATCTCCACTTCATCCTCCAAGCCATTCAAGTTTCCTTTCCAGAAGCA

Figure 6 (continued)

ACTGCTACTGCCTTTCATTCATATGTTCTTCTAAAGATAGTCTACATTTGGAAATGTATGTTAAAAG
CACGTATTTTTAAAATTTTTTCCTAAATAGTAACACATTGTATGTCTGCTGTGTACTTTGCTATTTT
TATTTATTTTAGTGTTTCTTATATAGCAGATGGAATGAATTTGAAGTTCCCAGGGCTGAGGATCCAT
GCCTTCTTTGTTTCTAAGTTATCTTTCCCATAGCTTTTCATTATCTTTCATATGATCCAGTATATGTTA
AATATGTCCTACATATACATTTAGACAACCACCATTTGTTAAGTATTTGCTCTAGGACAGAGTTTGG
ATTTGTTTATGTTTGCTCAAAAGGAGACCCATGGGCTCTCCAGGGTGCACTGAGTCAATCTAGTCCT
AAAAAGCAATCTTATTATTAACTCTGTATGACAGAATCATGTCTGGAACTTTTGTTTTCTGCTTTCT
GTCAAGTATAAACTTCACTTTGATGCTGTACTTGCAAAATCACATTTTCTTTCTGGAAATTCCGGCA
GTGTACCTTGACTGCTAGCTACCCTGTGCCAGAAAAGCCTCATTCGTTGTGCTTGAACCCTTGAATG
CCACCAGCTGTCATCACTACACAGCCCTCCTAAGAGGCTTCCTGGAGGTTTCGAGATTCAGATGCC
CTGGGAGATCCAGAGTTTCCTTTCCCTCTTGGCCATATTCTGGTGTCAATGACAAGGAGTACCTTG
GCTTTGCCACATGTCAAGGCTGAAGAAACAGTGTCTCCAACAGAGCTCCTTGTGTTATCTGTTTGTA
CATGTGCATTTGTACAGTAATTGGTGTGACAGTGTTCTTTGTGTGAATTACAGGCAAGAATTGTGGC
TGAGCAAGGCACATAGTCTACTCAGTCTATTCCTAAGTCCTAACTCCTCCTTGTGGTGTTGGATTTG
TAAGGCACTTTATCCCTTTTGTCTCATGTTTCATCGTAAATGGCATAGGCAGAGATGATACCTAATT
CTGCATTTGATTGTCACTTTTTGTACCTGCATTAATTTAATAAAATATTCTTATTTATTTGTTACTTG
GTACACCAGCATGTCCATTTTCTTGTTTATTTGTGTTTAATAAAATGTTCAGTTTAACATCCCAGTG
GAGAAAGTTAAAAAA (SEQ ID NO:3)

Human PD-L1 amino acid (Q9NZQ7)
<u>MRIFAVFIFMTYWHLLNA</u>(FTVTVPKDLYVVEYGSNMTIECKFPVEKQLDLAALIVYWEMEDKNII
QFVHGEEDLKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNSKREEKLFNV
TSTLRINTTTNEIFYCTFRRLDPEENHTAELVIPELPLAHPPNERTHL)VILGAILLCLGVALTFIF*RLRK
GRMMDVKKCGIQDTNSKKQSDTHLEET* (SEQ ID NO:4)

Humanized CD274 mRNA
GAAATCGTGGTCCCCAAGCCTCATGCCAGGCTGCACTTGCACGTCGCGGGCCAGTCTCCTCGCCTG
CAG<u>ATAGTTCCCAAAACATGAGGATATTTGCTGGCATTATATTCACAGCCTGCTGTCACTTGCT
ACGGG</u>(CATTTACTGTCACGGTTCCCAAGGACCTATATGTGGTAGAGTATGGTAGCAATATGA
CAATTGAATGCAAATTCCCAGTAGAAAAACAATTAGACCTGGCTGCACTAATTGTCTATTGGG
AAATGGAGGATAAGAACATTATTCAATTTGTGCATGGAGAGGAAGACCTGAAGGTTCAGCAT
AGTAGCTACAGACAGAGGGCCCGGCTGTTGAAGGACCAGCTCTCCCTGGGAAATGCTGCACT
TCAGATCACAGATGTGAAATTGCAGGATGCAGGGGTGTACCGCTGCATGATCAGCTATGGTG
GTGCCGACTACAAGCGAATTACTGTGAAAGTCAATG<u>CCCCATACAACAAAATCAACCAAAGA
ATTTTGGTTGTGGATCCAGTCACCTCTGAACATGAACTGACATGTCAGGCTGAGGGCTACCC
CAAGGCCGAAGTCATCTGGACAAGCAGTGACCATCAAGTCCTGAGTGGTAAGACCACCACCA
CCAATTCCAAGAGAGAGGAGAAGCTTTTCAATGTGACCAGCACACTGAGAATCAACACAACA
ACTAATGAGATTTTCTACTGCACTTTTAGGAGATTAGATCCTGAGGAAAACCATACAGCTGAA
TTGGTCATCCCAG</u>AACTACCTCTGGCACATCCTCCAAATGAAAGG)ACTCACTGGGTGCTTCT
GGGATCCATCCTGTTGTTCCTCATTGTAGTGTCCACGGTCCTCCTCTTCTTGAGAAAACAAG<u>T
GAGAATGCTAGATGTGGAGAAATGTGGCGTTGAAGATACAAGCTCAAAAAACCGAAATGATA</u>
CACAATTCGAGGAGACGTAAGCAGTGTTGAACCCTCTGATCGTCGATTGGCAGCTTGTGGTCTGT
GAAAGAAAGGGCCCATGGGACATGAGTCCAAAGACTCAAGATGGAACCTGAGGGAGAGAACCAA
GAAAGTGTTGGGAGAGGAGCCTGGAACAACGGACATTTTTCCAGGGAGACACTGCTAAGCAAGT
TGCCCATCAGTCGTCTTGGGAAATGGATTGAGGGTTCCTGGCTTAGCAGCTGGTCCTTGCACAGTG
ACCTTTCCTCTGCTCAGTGCCGGGATGAGAGATGGAGTCATGAGTGTTGAAGAATAAGTGCCTTC
TATTTATTTTGAGTCTGTGTGTTCTCACTTTGGGCATGTAATTATGACTGGTGAATTCTGACGACAT
GATAGATCTTAAGATGTAGTCACCAAACTCAACTGCTGCTTAGCATCCTCCGTAACTACTGATACA
AGCAGGGAACACAGAGGTCACCTGCTTGGTTTGACAGGCTCTTGCTGTCTGACTCAAATAATCTTT
ATTTTTCAGTCCTCAAGGCTCTTCGATAGCAGTTGTTCTGTATCAGCCTTATAGGTGTCAGGTATAG
CACTCAACATCTCATCTCATTACAATAGCAACCCTCATCACCATAGCAACAGCTAACCTCTGTTATC
CTCACTTCATAGCCAGGAAGCTGAGCGACTAAGTCACTTGCCCACAGAGTATCAGCTCTCAGATTT

Figure 6 (continued)

```
CTGTTCTTCAGCCACTGTCCTTTCAGGATAGAATTTGTCGTTAAGAAATTAATTTAAAAACTGATTA
TTGAGTAGCATTGTATATCAATCACAACATGCCTTGTGCACTGTGCTGGCCTCTGAGCATAAAGAT
GTACGCCGGAGTACCGGTCGGACATGTTTATGTGTGTTAAATACTCAGAGAAATGTTCATTAACAA
GGAGCTTGCATTTTAGAGACACTGGAAAGTAACTCCAGTTCATTGTCTAGCATTACATTTACCTCAT
TTGCTATCCTTGCCATACAGTCTCTTGTTCTCCATGAAGTGTCATGAATCTTGTTGAATAGTTCTTTT
ATTTTTTAAATGTTTCTATTTAAATGATATTGACATCTGAGGCGATAGCTCAGTTGGTAAACCCTT
TCCTCACAAGTGTGAAACCCTGAGTCTTATCCCTAGAACCCACATAAAAACAGTTGCGTATGTTT
GTGCATGCTTTTGATCCCAGCACTAGGGAGGCAGAGGCAGGCAGATCCTGAGCTCTCATTGACCAC
CCAGCCTAGCCTACATGGTTAGCTCCAGGCCTACAGGAGCTGGCAGAGCCTGAAAAACGATGCCTA
GACACACACACACACACACACACACACACACACACACACACACACACCATGTACTCATAGACCTAAG
TGCACCCTCCTACACATGCACACACATACAATTCAAACACAAATCAACAGGGAATTGTCTCAGAAT
GGTCCCCAAGACAAAGAAGAAGAAAAACACCAAACCAGCTCTATTCCCTCAGCCTATCCTCTCTAC
TCCTTCCTAGAAGCAACTACTATTGTTTTGTATATAAATTTACCCAACGACAGTTAATATGTAGAA
TATATATTAAAGTGTCTGTCAATATATATTATCTCTTTCTTTCTTTCTTCCTTTCTTTCTTTCTTT
CTTTCTTTCTTTCTTTCTTTCTTTCTTCCTTCCTTCCTTCCTTCCTTCCTTCCTTCCTTCCTTTCTT
TCTTTCTTTCTTTTTTCTGTCTATCTGTACCTAAATGGTTGCTCACTATGCATTTTCTGTGCTCTTCG
CCCTTTTTATTTAATGTATGGATATTTATGCTGCTTCCAGAATGGATCTAAAGCTCTTTGTTTCTAGG
TTTTCTCCCCCATCCTTCTAGGCATCTCTCACACTGTCTAGGCCAGACACCATGTCTGCTGCCTGAA
TCTGTAGACACCATTTATAAAGCACGTACTCACCGAGTTTGTATTTGGCTTGTTCTGTGTCTGATTA
AAGGGAGACCATGAGTCCCCAGGGTACACTGAGTTACCCCAGTACCAAGGGGGAGCCTTGTTTGTG
TCTCCATGGCAGAAGCAGGCCTGGAGCCATTTTGGTTTCTTCCTTGACTTCTCTCAAACACAGACGC
CTCACTTGCTCATTACAGGTTCTCCTTTGGGAATGTCAGCATTGCTCCTTGACTGCTGGCTGCCCTG
GAAGGAGCCCATTAGCTCTGTGTGAGCCCTTGACAGCTACTGCCTCTCCTTACCACAGGGGCCTCT
AAGATACTGTTACCTAGAGGTCTTGAGGATCTGTGTTCTCTGGGGGGAGGAAAGGAGGAGGAACC
CAGAACTTTCTTACAGTTTTCCTTGTTCTGTCACATGTCAAGACTGAAGGAACAGGCTGGGCTACGT
AGTGAGATCCTGTCTCAAAGGAAAGACGAGCATAGCCGAACCCCGGTGGAACCCCCTCTGTTACC
TGTTCACACAAGCTTATTGATGAGTCTCATGTTAATGTCTTGTTTGTATGAAGTTTAAGAAAATATC
GGGTTGGGCAACACATTCTATTTATTCATTTTATTTGAAATCTTAATGCCATCTCATGGTGTTGGATT
GGTGTGGCACTTTATTCTTTTGTGTTGTGTATAACCATAAATTTTATTTTGCATCAGATTGTCAATGT
ATTGCATTAATTTAATAAATATTTTTATTTATTAAAAAAAAAAAAAAAAAA (SEQ ID NO:5)
```

Humanized PD-L1 amino acid

<u>MRIFAGIIFTACCHLLRA</u>(FTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRIT)VKV
NAPYNKINQRILVVDPVTSEHELTCQAEGYPKAEVIWTSSDHQVLSGKTTTTNSKREEKLFNVTST
LRINTTTNEIFYCTFRRLDPEENHTAELVIPELPLAHPPNERTHWVLLGSILLFLIVVSTVLLFL<u>RKQVR</u>
<u>MLDVEKCGVEDTSSKNRNDTQFEET</u> (SEQ ID NO:6)

Humanization fragment A

```
GTCACGGTTCCCAAGGACCTATATGTGGTAGAGTATGGTAGCAATATGACAATTGAATGCAAATTC
CCAGTAGAAAAACAATTAGACCTGGCTGCACTAATTGTCTATTGGGAAATGGAGGATAAGAACATT
ATTCAATTTGTGCATGGAGAGGAAGACCTGAAGGTTCAGCATAGTAGCTACAGACAGAGGGCCCG
GCTGTTGAAGGACCAGCTCTCCCTGGGAAATGCTGCACTTCAGATCACAGATGTGAAATTGCAGGA
TGCAGGGGTGTACCGCTGCATGATCAGCTATGGTGGTGCCGACTACAAGCGAATTACTGTGAAAGT
CAATGGTAAGAATTATTATAGATGAGAGGCCTGATCTTTATTGAAAACATATTCCAAGTGTTGAAG
ACTTTTCATTCTTGTAAGTCCATACTTATTTTCAAACAGAACAGCATAGTCTGTTCATTCATTCATTC
AATTCATGAATTCATTCACATAATTATCCAATTTCTTGAGCACCTATTTGATAGTCACTGGAAATCC
AGAGACAAACAACACAGAGCCATGTTCTACAGTATGTACAGTTTCCAAAAAGAATTTCTAGTCTT
TACTTTTTATTACAAATGGAATACGTATACTTGCAAATAATTCAGATACTGTGGAAGAGATCAAA
TGAATTGCAAAAGTGTCCCTCCTCCCTTCACCACTATCTCCCATGGCATGCAGAGAGAGTAACCATT
ATTTGTGTGTCCCTCCAGAAATTTTTTATTCAACTACTATTTTTTATTTTATTAGGTCCGTCAGTTT
TCCTTTTTTGAGCCTCTCTATATCAAATGCAAATAAATATATTCAGAACAAACCCCACTGTAAGGTT
CACATTAAAAAAGACTTGAAGTCACCCTATGAAGACAAAAAATAATCACATTAAGTGTGAAAGAA
```

Figure 6 (continued)

```
CCTATTCTTCCAGTACAGGATAAGCCATACTTACTGGGCATATATTCATCTTGAAAATCTATACTGA
TGTTGTCTTGGGGAATTGAAAAGGAACTAGGAGTGTTAGTTCCTCGGTATTGACCCACAGTTATGTT
ATCAGGTCACTTGAGTTCAAAGTTTTGTGTTGGCACTAGCTAAGTAAAGGAAAACACCTCTGCTTTC
ATTGTTGAGTTTCACAGAATTGAGAGCTGAAAGGATCCCAGGCAGGAGCAGCTAATCCAAACTCCC
ACAAAGAACAAAAATCCCCAGAGGATCTTCTGTTCTTATATTTCCTGCAATGGCGTCCCTGTCATA
TCCCACAATGGCCTCCCTGCCATTTGGATATCCCTTCCATATCCTGTTGAATTACTCCCTAATAGT
AAGCTGAAATCTGCCCCTCTAGTTGTAGTCTTGGGATTATTTCATTTACATGATGACCTTTTAATATT
TGACTAGAATTAAATCATCTCCCCTTGGTCTTTCCATTCCTGGGCTAACTACCATCAATCTGAGGGC
TAACAATACAAGTAGAAAAGTATACATTTGTCACTGATCACTGATCAATTATTAATCAATGATCA
CTGATAACTATAAACTCAAAAACAAAATCATGTGGGGATTAAGAGAAATGTATCAGTTTTATGTTG
TATTTCTGGTCCCTGATACTGGCTCAGGTAATGCCACTATTGTCAAGAAGATACCACTTGTAAAGTA
GATTTAATTTTCATTATATTTTACCATATGCTTCTCCATTCATGACATCTCTTGAGATGTTGTGGTTT
ATACTTTCAGTTTTTCTCCAGTCCATCCGCAAATATCAGGCATCTACTGTGTTCCAAGATATTAAAG
AAATCATCATGACTTAGCCTCATCAACAGCATTGCTAGATCTGGGATGGAAAGGAAGAGTATAATC
CTGGCAGTCAGGAAGAAGGCAGCATAAAGTATAAGTTTCTGCTTCCAAAAAAGGTCTCTCATCAGC
CTGTAGGGAGTGTGTAGGGAAGGGACAGCTGTCCTTGTAGTAGGGAAGGGTTTTATTCAGGTCGTC
TGGGCTCCATAATATCCCTTGTGTATCTGCAGTCTCCTTTGCCATGGATCAACACAATAGGAAATCT
TCCGGCACTGATGGTTTTTCCAAGGGGGAGTTCTTCCTGGAGCAAAGCAAATGACCAACCAGGTTT
GAGGACCTGATTTGTTTGACAATTCCATTTTGTATTGTAAATTACTTAATTGGCATTCTACTCCCAAT
CCATCTTGTCATTTGCATACAGTGGTTTTGGGATTGAGTTCAGCTATACCAAAAGTCTGAACCTTCT
GCACTTAGAACAAGGCAACCACCAAGCTTCACTTGCACTGAGGCCGTGTCTCCAATGGAAATGAGG
CAGCTGGCTTGCAGGAGCTTCCCAACTCAGGGAAGTAGAACTCCTGAGTCACCTCCATATGCAAAT
GATTTCACAGTAATGCTGTTGAACTTCACTTCCCATCACAGCAAATGTGTGGTAACATAGCTTCCCC
ACAGGAGTTTACTCACCATGGTATTTTAAAGGTGAAACATTTCAAAACTGAAATTTGAAAGAATTT
AGTTTTGGATTCACTCAATTATCACTATCACTTCGGGTGTTATTGCACCTTTCTTGTTTGTGAGTTTA
AATGCCAGACTCTCAGGCCACTAACTTTCAATTAAAAGTGTTTTTCTTTAATCGCTGAACCTAACAG
CAGGGAAAACGAAATGTTCATTCAGACTTTCAGAACCTTCAATGAGATTAGGCAGCTGAAAGATCA
AAGTGTTGCATAGTTGTCCCGATAAAGCTATTTGGATCATATGGACCAAATCGACTGCTGTCATTCC
CCACCAACCCCATCTCTCCCAAAATTCCCAGCCCTGTTTAAGTGTTCTCTGTAGCATTTATCTCTAT
CTAGTATATTGTGTAGCATATCATATCATACTTTTCTGTTTTGTTTATTGTCTCTCTCCTCCTAGAAT
ATAAACTCCACAAGCACAAAGATTTGGGCCTGTTTTATAATATTGTTGCATCCCCAGGGCCTGATAT
ACAGCAGAGTGGTGGTACGAAAAGAGCACACAAAAAAATATTTGTTGAGTCAATGAATGAATGAT
TTCCTCAAATAGGATTAGCCTAAAATTTTGGAAACATGAACAGATTTGGATATGTGAAAATTTATTT
CCAGACTGTTCATCAGGAACTGTTAGCAGCTTCTAAAGGGTACACTGGAGCAGCAGTAGTAAAAG
GAGGAAGAGGAGCAGCTCTGCTACTGCTACTATCGAGTACTACTACAATTAGCACTTGCTTATTCT
GTGTGTTAGGCCCTGTACTGAACACTCTGTCTAAATTAGTTCATTTCCTCCTGGAAATGACTCTAGG
GGGTAAGTGCTTCATCATGTAAGATGAGTATTTTTCACATTTTGTTGTGTCTGAAATCTGAGTGTGT
CTTTCAATGATGGAATCTTTGATTCCATGATAAGTGGTATTATTCCCATTTTAAGGATGAGGAAACT
GAGGTCCAAAGAAATTAAGTAATTTGCCCAAATTCACCCAGCCTAGAAAATGATAAAGCTAGTTCT
AAACCCAAGCAGATTAGCTCTGAAGTCTGGGCCCTTAATAACCACTTTTTATTGCCTATATTTGTAC
CTCTGGTGTACGTATCAAGTTATATGTTGACTTCAAAACTATCATGACCTTTTCTTGGTTTTGATTGT
CCAACATTAGTATAGTGTTCTGGGTCTGCAAAAATTTTGATTACTCATCTCATCTGTAAAACATTTT
GAACTCGTGTGTTTGTGCATGCACATTTGTGTGTAATTATAAAATTTTACTTTCTGTTAATATATA
AGTTGTATCATAAGAAACTGCCGTTTTGAAGAGCAAAAAAGGTTGAATGTTACCAGTTACATCT
GGTTCAACCTAATAGACATTTGTACAAAAACAGACATTTTAAGAGGTTGAAATAAAAATTTAATAA
ACAATATTTTCAGTTTTACTAATTGTGATGCTTCACTATCATTAGCTAATATGTCAAGGCATAATA
TACCTTAGGGTGAACTTTATCATTAACAAAGGTGGATGGTGTCAATAATCTTGAGGTTTGTGTTTT
TTATATAACACTGCGAGGTCTAATTAAGTACTTACTGTTTACCACCTCATACAGTGGCCGATAAAA
AGTGTCACTTCTGCTGTTTCCTCTGGGTTGTGCTTGAATTATTAGTATTATCTTCAGTCCTCAGTTTC
TTTGTGGGAAACTTTTTAATTAGTTGTTTAATTTTGTAAGATGGTTAGTTTAGTCAAAATTAGATAA
GAGAATTTGAAAATCCGTAGCTACCCCAAAGCAACCTACACATAAGAACTATTATTTTGTGTTTTG
AAATCATAATTTTATTGATTTCCAGTGTTTCCACTGGTAGTGGTTTCATTGATATAGGAGTATCAAA
ACATCACTCATTATTTATTTCAGTTTCATTTGATCCTAGCCGTTTTGTATTAACTCTCTGTGAAGAAA
```

Figure 6 (continued)

```
TTACCTCACAAATCTATTGCTGTCGCTAGCTCGCTACCTTAGGACCGTTATAGTTACTAGCATAACT
TCGTATAGCATACATTATACGAAGTTATTCCAGACATGATAAGATACATTGATGAGTTTGGACAAA
CCACAACTAGAATGCAGTGAAAAAAATGCTTTATTTGTGAAATTTGTGATGCTATTGCTTTATTTGT
AACCATTATAAGCTGCAATAAACAAGTTAACAACAACAATTGCATTCATTTTATGTTTCAGGTTCA
GGGGGAGGTGTGGGAGGTTTTTAAAGCAAGTAAAACCTCTACAGATGTGATATGGCTGATTATGA
TCATTACTTATCTAGAGCTTAGATCCCCCCTGCCCGGTTATTATTATTTTGACACCAGACCAACTG
GTAATGGTGCGGAGGCACGCTCAGCTGGAATTGGCCGCAACTAGGGCAGGTTTAACAACAACAAT
TGCATTCATTTTATGTTTCAGGTTCAGGGGGAGGTGTGGGAGGTTTTTAAAGCAAGTAAAACCTCT
ACAGATGTGATATGGCTGATTATGATCATTACTTATCTAGATCAATCGCCATCTTCCAGCAGGCGCA
CCATTGCCCCTGTTTCACTATCCAGGTTACGGATATAGTTCATGACAATATTTACATTGGTCCAGCC
ACCAGCTTGCATGATCTCCGGTATTGAAACTCCAGCGCGGGCCATATCTCGCGCGGCTCCGACACG
GGCACTGTGTCCAGACCAGGCCAGGTATCTCTGACCAGAGTCATCCTAAAATACACAAACAATTAG
AATCAGTAGTTTAACACATTATACACTTAAAAATTTTATATTTACCTTAGCGCCGTAAATCAATCGA
TGAGTTGCTTCAAAAATCCCTTCCAGGGCGCGAGTTGATAGCTGGCTGGTGGCAGATGGCGCGGCA
ACACCATTTTTCTGACCCGGCAAAACAGGTAGTTATTCGGATCATCAGCTACACCAGAGACGGAA
ATCCATCGCTCGACCAGTTTAGTTACCCCAGGCTAAGTGCCTTCTCTACACCTGCGGTGCTAACCA
GCGTTTTCGTTCTGCCAATATGGATTAACATTCTCCCACCGTCAGTACGTGAGATATCTTTAACCCT
GATCCTGGCAATTTCGGCTATACGTAACAGGGTGTTATAAGCAATCCCCAGAAATGCCAGATTACG
TATATCCTGGCAGCGATCACTATTTTCCATGAGTGAACGAACCTGGTCGAAATCAGTGCGTTCGAA
CGCTAGAGCCTGTTTTGCACGTTCACCGGCATCAACGTTTTCTTTTCGGATCCGCCGCATAACCAGT
GAAACAGCATTGCTGTCACTTGGTCGTGGCAGCCCGGACCGACGATGAAGCATGTTTAGCTGGCCC
AAATGTTGCTGGATAGTTTTTACTGCCAGACCGCGCGCCTGAAGATATAGAAGATAATCGCGAACA
TCTTCAGGTTCTGCGGGAAACCATTTCCGGTTATTCAACTTGCACCATGCCGCCCACGACCGGCAA
ACGGACAGAAGCATTTTCCAGGTATGCTCAGAAAACGCCTGGCGATCCCTGAACATGTCCATCAGG
TTCTTGCGAACCTCATCACTCGTTGCATCGACCGGTAATGCAGGCAAATTTTGGTGTACGGTCAGTA
AATTGGAATTTAAATCGGTACGCACCTTCCTCTTCTTCTTGGGGGTACCCATGGTGCTGGCTTGGCC
GGGAGCTGGCTCAGAGCAGGGGACACCACCTGGGTCGAGCCAGCCAACCTGTGAGCAGGTGGAAT
TTTGTGGGCTGTGGCCTGGGAGCCAGCACCCTCTTCCTCTTATAGATACTAGTGGCCCCTAGGAATT
ATGAAGTCAAAGAGGACCAGGACCTCACAGACCATGGCCAGTGAGGACCTGTACCATGTCCAAAT
ATGGGCATGAGAGGGGTGGGCAGGGCTTTGGCATCAGGAGTTGCTTGTGTCACAGTCAAGAAGTG
ACAAAGATGGCATCCACTTGAGTGTTCAGTTAGTCACTCAGCTTAGGTGTTAAGTGCCACACACCT
GCTTCTAGGCTAGGTCCTGATAGATAACCCAAGGCCAGGCAGGTGGGTGAAACAGCCACATGGAT
TTGAACTGTGAAAAGCACACATCTTCAGACTGCTCAGAGAATGCTGCTGAGGGAACTTGACCTTTT
AAGAAATTATCCAACGCCCCAGTGAGGCACTGACAGACAAATCCAGAGGGTCTCAGAGTTGCAGG
GGGGTGGGCTCTAGTAAAACATTGAGGCCCCATCAAGTGCTTCAGGTATAAATGGGAGCCACATG
GATGCAGAGCAGTGTTTGGACTGAGGGAGGTGTTGGACATTACTAGACAGAAGGTGGACGTGGGT
GCTGCTACTGGCGCCCGGGCTAGGGGCTGCAGGTCGAGGTCTGATGGAATTAGAACTTGGCAAAA
CAATACTGAGAATGAAGTGTATGTGGAACAGAGGCTGCTGATCTCGTTCTTCAGGCTATGAAACTG
ACACATTTGGAAACCACAGTACTTAGAACCACAAAGTGGGAATCAAGAGAAAAACAATGATCCCA
CGAGAGATCTATAGATCTATAGATCATGAGTGGGAGGAATGAGCTGGCCCTTAATTTGGTTTTGCT
TGTTTAAATTATGATATCCAACTATGAAACATTATCATAAAGCAATAGTAAAGAGCCTTCAGTAAA
GAGCAGGCATTTATCTAATCCCACCCCACCCCCACCCCCGTAGCTCCAATCCTTCCATTCAAAATGT
AGGTACTCTGTTCTCACCCTTCTTAACAAAGTATGACAGGAAAACTTCCATTTTAGTGGACATCTT
TATTGTTTAATAGATCATCAATTTCTGCAGACTTACAGCGGATCCCTCAGAAGAACTCGTCAAGA
AGGCGATAGAAGGCGATGCGCTGCGAATCGGGAGCGGCGATACCGTAAAGCACGAGGAAGCGGT
CAGCCCATTCGCCGCCAAGCTCTTCAGCAATATCACGGGTAGCCAACGCTATGTCCTGATAGCGGT
CCGCCACACCCAGCCGGCCACAGTCGATGAATCCAGAAAAGCGGCCATTTTCCACCATGATATTCG
GCAAGCAGGCATCGCCATGGGTCACGACGAGATCATCGCCGTCGGGCATGCGCGCCTTGAGCCTG
GCGAACAGTTCGGCTGGCGCGAGCCCCTGATGCTCTTCGTCCAGATCATCCTGATCGACAAGACCG
GCTTCCATCCGAGTACGTGCTCGCTCGATGCGATGTTTCGCTTGGTGGTCGAATGGGCAGGTAGCC
GGATCAAGCGTATGCAGCCGCCGCATTGCATCAGCCATGATGGATACTTTCTCGGCAGGAGCAAGG
TGAGATGACAGGAGATCCTGCCCCGGCACTTCGCCCAATAGCAGCCAGTCCCTTCCCGCTTCAGTG
ACAACGTCGAGCACAGCTGCGCAAGGAACGCCCGTCGTGGCCAGCCACGATAGCCGCGCTGCCTC
```

Figure 6 (continued)

```
GTCCTGCAGTTCATTCAGGGCACCGGACAGGTCGGTCTTGACAAAAAGAACCGGGCGCCCCTGCGC
TGACAGCCGGAACACGGCGGCATCAGAGCAGCCGATTGTCTGTTGTGCCCAGTCATAGCCGAATAG
CCTCTCCACCCAAGCGGCCGGAGAACCTGCGTGCAATCCATCTTGTTCAATGGCCGATCCCATGGT
TTAGTTCCTCACCTTGTCGTATTATACTATGCCGATATACTATGCCGATGATTAATTGTCAACACGT
CTAACAAAAAAGCCAAAAACGGCCAGAATTTAGCGGACAATTTACTAGTCTAACACTGAAAATTA
CATATTGACCCAAATGATTACATTTCAAAAGGTGCCTAAAAAACTTCACAAAACACACTCGCCAAC
CCCGAGCGCATAGTTCAAAACCGGAGCTTCAGCTACTTAAGAAGATAGGTACATAAAACCGACCA
AAGAAACTGACGCCTCACTTATCCCTCCCCTCACCAGAGGTCCGGCGCCTGTCGATTCAGGAGAGC
CTACCCTAGGCCCGAACCCTGCGTCCTGCGACGGAGAAAAGCCTACCGCACACCTACCGGCAGGTG
GCCCCACCCTGCATTATAAGCCAACAGAACGGGTGACGTCACGACACGACGAGGGCGCGCGCTCC
CAAAGGTACGGGTGCACTGCCCAACGGCACCGCCATAACTGCCGCCCCGCAACAGACGACAAAC
CGAGTTCTCCAGTCAGTGACAAACTTCACGTCAGGGTCCCAGATGGTGCCCCAGCCCATCTCACC
CGAATAAGAGCTTTCCCGCATTAGCGAAGGCCTCAAGACCTTGGGTTCTTGCCGCCCACCATGCCC
CCCACCTTGTTTCAACGACCTCACAGCCCGCCTCACAAGCGTCTTCCATTCAAGACTCGGGAACAG
CCGCCATTTTGCTGCGCTCCCCCAACCCCCAGTTCAGGGCAACCTTGCTCGCGGACCCAGACTAC
AGCCCTTGGCGGTCTCTCCACACGCTTCCGTCCCACCGAGCGGCCCGGCGGCCACGAAAGCCCCGG
CCAGCCCAGCAGCCCGCTACTCACCAAGTGACGATCACAGCGATCCACAAACAAGAACCGCGACC
CAAATCCCGGCTGCGACGGAACTAGCTGTGCCACACCCGGCGCGTCCTTATATAATCATCGGCGTT
CACCGCCCCACGGAGATCCCTCCGCAGAATCGCCGAGAAGGGACTACTTTTCCTCGCCTGTTCCGC
TCTCTGGAAAGAAAACCAGTGCCCTAGAGTCACCCAAGTCCCGTCCTAAAATGTCCTTCTGCTGAT
ACTGGGGTTCTAAGGCCGAGTCTTATGAGCAGCGGGCCGCTGTCCTGAGCGTCCGGGCGGAAGGAT
CAGGACGCTCGCTGCGCCCTTCGTCTGACGTGGCAGCGCTCGCCGTGAGGAGGGGGGCGCCCGCG
GGAGGCGCCAAAACCCGGCGCGGAGGCCATGCATATAACTTCGTATAGCATACATTATACGAAGTT
ATCTCGAGCTTGGTAAAGGAATGGAGAATTAAGGCTCTAGATCATTAGTGGTTACACTATAGTATT
AGAAGTAAAAAAAAGATTATACCAACAAAATAAGAACATGTTAATGTACTTGTAATGAATAAACA
TGAATAAAGCTCTTATGCTATATAGGTGCACTAAACAATCTACTAGAATTGTCAGCAAACTACGTA
TCTTAATCCTGAAAGGGTCCCAAACCAATGATCTAAAATTGAATCAAACTTTCTTCCTTGAGCATAA
TTACTTAAATGATTTATTAAAATAGCCAGCATTTAAAAGCTTAAAATGTAAATATCATAATGTGGT
ATCCTAGATAGCATCCAGAACAGAAAAAGGATATTAGGGAAAAACTGGAGGAATGGAATAAATT
ATGCAGTTTAGTTATTAATAATGTACTAACGTCCTTAGTTATGACGATTGTACCATGGTAATGTAAG
ATACTAACAATAGAGGAAACCGGGTAAGGAGTATACAGTAACTCTATACTATCTTTGCAACTTTTT
TGTAAATTTAAAACTTCTAAAATAAAGAACAAATTTAAACATTAAAAAGTATCACCAGGAACATAT
ATCACTGTTTACAGATGAAATACTATGTATTTTCATATCTAATTTCTGATCATTGACTTCAAATCAG
AAAAGTGAATGACACCTCAAAATCAGGTTTTCTGTTTACTGAAGTCTAAGAAAAGAAAGCATACCA
GCTGGAGAGATTCATGTTTATAAAGACAGATTTATAACAACAAAAATAAAATATCCAAGAATAAA
TTTAAGAAGAAGCACTTTACTGAGAAACATATGAAAACCTGAACAAATGGAGAGGGATATTTTGT
ATTTGAATAGAAAGACTTCTGGTTTAAAGATAATTCTCTTTAAATTATTTTTTGTAGAAATTTAAGG
GGTACAAGAGCAGTGTTGTCACATGGATATATTACATAGTGGTGAAGTCTGGGGTTTTAGTGTAAA
TTAATCTTTACATTTTGTTTGAGCCCAATAAATGTACCAACATGATTTTATAGAAAGATAGTCATT
CCTATTAATCCAAACTTGTCCCAACTTTGAATTGAATTGAGGCAGAGCTAGCAGGTGTTCCCCACG
GCTGAGGCATCTGAACATTAAGCATATCCCTCTGAGAACCAGCCTGCATTGATACTCTTTCTAATGT
GGACAGCATCAAGCTATGTACGTAGTTCTGTGCTCAGCAAAAGCCCTGACTTCTTTTTGTTTATGTC
CTAGCCCCATACAACAAAATCAACCAAAGAATTTGGTTGTGGATCCAGTCACCTCTGAACATGAA
CTGACATGTCAGGCTGAGGGCTACCCCAAGGCCGAAGTCATCTGGACAAGCAGTGACCATCAAGT
CCTGAGTGGTAAGACCACCACCACCAATTCCAAGAGAGAGGAGAAGCTTTTCAATGTGACCAGCA
CACTGAGAATCAACACAACAACTAATGAGATTTTCTACTGCACTTTTAGGAGATTAGATCCTGAGG
AAAACCATACAGCTGAATTGGTCATCCCAGGTAATATTCTGAATGTGTCCATTAAAATATGTCTAA
CACTGTCCCCTAGCACCTAGCATGATGTCTGCCTATCATAGTCATTCAGTGATTGTTGAATAAATGA
ATGAATGAATAACACTATGTTTACAAAATATATCCTAATTCCTCACCTCCATTCATCCAAACCATAT
TGTTACTTAATAAACATTCAGCAGATATTTATGGAATATACCTTTTGTTCCATGCATTGTAGTACTC
ATTGGATACACATAGAATAATAAGACTCAGTTCACACTCTTCAGGAAACAGATAAAAAACTAAGA
AACAAACAAAAAACAGGCAATCCAACACCATGTGGGAAATGCTTTCATAGCCGGGAAACCTGGGG
AATACCTGAGAGGAATACTCAATTCAGGCCTTGTTTCAGGAATCCAAATCCTGGCACATCAGAGCT
```

Figure 6 (continued)

```
GCTTCCCTCTTTCCAGGGTGGCAGGAAATAAATGGAACATATTTTCTATCTTATGCCAAACATGAG
GGACCCTTTCTCCCCGGTGCCTCTCCCAAGGTAGTCTACAATATTTCAACTCTAGCAGTCTGCTTAG
TGCATAGAACATGAGGCTGTGTGTCCCTGGGCAAATTACTAGACTTCTGTGTGCTTCACTTTCCCTG
TAGGATTATAATCTACTGAGCAAGCTTATTGTAAGGGTCAGATTAGCAACAGTGTATGAAAATGAT
TTGAGACCATTGCCTGCACAAATTCAACTATTTTTTTTATCTCACTACTCTACAGAAGTAGGTAGG
GTGGGAGACAGAGTCTGATGAGAGGCTCAGAATGTGAAAGAAAGTGAGGCGAGTGAGCATGATAT
TTAATATAAACACAAAGATATTCTGAGAAGAGCTGCTCACTGCCCCCTCCCCCAATACATGTTGAT
AGGAAAATGCCACGTACTTCAGCAAAAACAACTGAAAAATTAGATAGAAAAGTCAATCAATAGGA
AAAGATAATCCAGGACGGTGTTGTGAACAGAAAGAGGGGGAAAAAACTTTAGAAAATGATGGGG
ATGCTCTTACTGGGGTACGAGTCCTCAGGTATTGAACTGGCTTTCAGTAAAAGCTAGATTAGTGGG
TTCCTGCCATTTACAAGCTGTTTATGACAACTTACTTGTTGGGTGGCCTACAGTAACTCACCTAAC
TGCACTGAGTCTGTTTCCTCATCTGTAAATTGGGGATTTTTTTTAAATACCTGGCATGCCTAACTCA
TAAAGTTGTTCTGAAACTGAAATAAAACATACGTGAACAGGCATTGTAAACTGTAAGTTACGGAAA
AAGCTGGCTGTTGTTGTGTCTTTAAAGTTTCACCTGGGTAGTCAAAGATGGATCATGGGTCTCAGTG
GAGAGCTGAGCCAGGCAGGAGCTGACTAAGGGTGAGAGGTGGGAGTTAGCAGCCTCTGAACATCT
GTGTACCATGGGACCCCCTTTCCTCCTGCATGGTACCCCAGACAAGGAGCCTAGTAAGAGATACTA
ATGGCTTGTTGTCCAGAGATGTTCAAACTGCAGAGAAAGATAAGACAACAAGCATTGGCCTCCAAT
CATGATGACAGATAGGAGGAGGTGGGAGCTCCTTAGCAGTGCTGGTTGGCCTTCCATGTTCTACTG
TGGGCCATCTCTGCCATGTACTGTAGGCTACTAGCTTCTATATTAAAGAATGCAAGAGGGGCCAGG
AGCGGAGGCTCATGCCTGTAATCTCAGCACTTTGGGAGGCCAAGGTGGGCAGATCACTTGAGGTCA
GGAGTTTGTGACCAGCCTGGCCAACATGGTGAAACTCTGCCTTTACTAAAAATATAAAAATTAGCT
GGGTGTGGTGGTGTGCACCTGTAATCCCAGCTACTCGGGAGACTGAGGCACAAGAATTGCTTGAAC
CTGGGAGGCGGAAGTTGCAGTGAGCCCAGATTGCGCCACTGCACTCCACCCTGGGCAACAGAGAA
AGACTCTGCCTCAAAAAAAAAAAAAAAAAGCAAGAGGAAGTGAAATAATCAAGGCCGCCATTTAA
TAGTGAGCAGCCACTCCATGTGGTACTGTGCAAGCACATTATAAATATTAGCCTCACAAGAAATGT
ATTAGCATTTGTATTTTGTACACTGGTTAAGTATCTTGCCCAAGACCTCAAAACTGGTTAAGGGCAG
CAGAATTTAGCCCCAGCACCACCTTTTCAAAGCCTGGGCTTCTCACACTTCTCCATGCTGTTCCCAT
TTTAACACAGGTATCTCGCCATTCCAGCCACTCAAACTTTGGCATTTAAGAAAATTATCCTAAAGCT
AAACTAAACTTCAAGGATGACCATTCTCCTGACCCCTTCCCATCAAAATTTTATCTTTAGTCAGTTT
GTTTTCGTTTTGTTTTGTTTTCAGAACTACCTCTGGCACATCCTCCAAATGAAAGG (SEQ ID NO:7)
```

Humanization fragment B
```
GTCACGGTTCCCAAGGACCTATATGTGGTAGAGTATGGTAGCAATATGACAATTGAATGCAAATTC
CCAGTAGAAAAACAATTAGACCTGGCTGCACTAATTGTCTATTGGGAAATGGAGGATAAGAACATT
ATTCAATTTGTGCATGGAGAGGAAGACCTGAAGGTTCAGCATAGTAGCTACAGACAGAGGGCCCG
GCTGTTGAAGGACCAGCTCTCCCTGGGAAATGCTGCACTTCAGATCACAGATGTGAAATTGCAGGA
TGCAGGGGTGTACCGCTGCATGATCAGCTATGGTGGTGCCGACTACAAGCGAATTACTGTGAAAGT
CAATGGTAAGAATTATTATAGATGAGAGGCCTGATCTTTATTGAAAACATATTCCAAGTGTTGAAG
ACTTTTCATTCTTGTAAGTCCATACTTATTTTCAAACAGAACAGCATAGTCTGTTCATTCATTCATTC
AATTCATGAATTCATTCACATAATTATCCAATTTCTTGAGCACCTATTTGATAGTCACTGGAAATCC
AGAGACAAACAACACAGAGCCATGTTCTACAGTATGTACAGTTTTCCAAAAAGAATTTCTAGTCTT
TACTTTTTTATTACAAATGGAATACGTATACTTGCAAATAATTCAGATACTGTGGAAGAGATCAAA
TGAATTGCAAAGTGTCCCTCCTCCCTTCACCACTATCTCCCATGGCATGCAGAGAGTAACCATT
ATTTGTGTGTCCCTCCAGAAATTTTTTATTCAACTACTATTTTTTATTTATTAGGTCCGTCAGTTT
TCCTTTTTTGAGCCTCTCTATATCAAATGCAAATAAATATATTCAGAACAAACCCCACTGTAAGGTT
CACATTAAAAAGACTTGAAGTCACCCTATGAAGACAAAAAATAATCACATTAAGTGTGAAAGAA
CCTATTCTTCCAGTACAGGATAAGCCATACTTACTGGGCATATATTCATCTTGAAAATCTATACTGA
TGTTGTCTTGGGGAATTGAAAAGGAACTAGGAGTGTTAGTTCCTCGGTATTGACCCACAGTTATGTT
ATCAGGTCACTTGAGTTCAAAGTTTTGTGTTGGCACTAGCTAAGTAAAGGAAAACACCTCTGCTTTC
ATTGTGAGTTTCACAGAATTGAGAGCTGAAAGGATCCCAGGCAGGAGCAGCTAATCCAAACTCCC
ACAAAGAACAAAAATCCCCAGAGGATCTTCTGTTCTTATATTTCCTGCAATGGCGTCCCTGTCATA
TCCCACAATGGCCTCCCTGCCATTTGGATATCCCTTCCATATCCTGTTGAAATTACTCCCTAATAGT
AAGCTGAAATCTGCCCCTCTAGTTGTAGTCTTGGGATTATTTCATTTACATGATGACCTTTTAATATT
```

Figure 6 (continued)

```
TGACTAGAATTAAATCATCTCCCCTTGGTCTTTCCATTCCTGGGCTAACTACCATCAATCTGAGGGC
TAACAATACAAGTAGAAAAAGTATACATTTGTCACTGATCACTGATCAATTATTAATCAATGATCA
CTGATAACTATAAACTCAAAAACAAAATCATGTGGGGATTAAGAGAAATGTATCAGTTTTATGTTG
TATTTCTGGTCCCTGATACTGGCTCAGGTAATGCCACTATTGTCAAGAAGATACCACTTGTAAAGTA
GATTTAATTTTCATTATATTTTACCATATGCTTCTCCATTCATGACATCTCTTGAGATGTTGTGGTTT
ATACTTTCAGTTTTTCTCCAGTCCATCCGCAAATATCAGGCATCTACTGTGTTCCAAGATATTAAAG
AAATCATCATGACTTAGCCTCATCAACAGCATTGCTAGATCTGGGATGGAAAGGAAGAGTATAATC
CTGGCAGTCAGGAAGAAGGCAGCATAAAGTATAAGTTTCTGCTTCCAAAAAGGTCTCTCATCAGC
CTGTAGGGAGTGTGTAGGGAAGGGACAGCTGTCCTTGTAGTAGGGAAGGGTTTTATTCAGGTCGTC
TGGGCTCCATAATATCCCTTGTGTATCTGCAGTCTCCTTTGCCATGGATCAACACAATAGGAAATCT
TCCGGCACTGATGGTTTTTCCAAGGGGGAGTTCTTCCTGGAGCAAAGCAAATGACCAACCAGGTTT
GAGGACCTGATTTGTTTGACAATTCCATTTTGTATTGTAAATTACTTAATTGGCATTCTACTCCCAAT
CCATCTTGTCATTTGCATACAGTGGTTTTGGGATTGAGTTCAGCTATACCAAAAGTCTGAACCTTCT
GCACTTAGAACAAGGCAACCACCAAGCTTCACTTGCACTGAGGCCGTGTCTCCAATGGAAATGAGG
CAGCTGGCTTGCAGGAGCTTCCCAACTCAGGGAAGTAGAACTCCTGAGTCACCTCCATATGCAAAT
GATTTCACAGTAATGCTGTTGAACTTCACTTCCCATCACAGCAAATGTGTGGTAACATAGCTTCCCC
ACAGGAGTTTACTCACCATGGTATTTTAAAGGTGAAACATTTCAAAACTGAAATTTGAAAGAATTT
AGTTTTGGATTCACTCAATTATCACTATCACTTCGGGTGTTATTGCACCTTTCTTGTTTGTGAGTTTA
AATGCCAGACTCTCAGGCCACTAACTTTCAATTAAAAGTGTTTTTCTTTAATCGCTGAACCTAACAG
CAGGGAAAACGAAATGTTCATTCAGACTTTCAGAACCTTCAATGAGATTAGGCAGCTGAAAGATCA
AAGTGTTGCATAGTTGTCCCGATAAAGCTATTTGGATCATATGGACCAAATCGACTGCTGTCATTCC
CCACCAACCCCATCTCTCCCCAAAATTCCCAGCCCTGTTTAAGTGTTCTCTGTAGCATTTATCTCTAT
CTAGTATATTGTGTAGCATATCATATCATACTTTTCTGTTTGTTTATTGTCTCTCTCCTCCTAGAAT
ATAAACTCCACAAGCACAAAGATTTGGGCCTGTTTTATAATATTGTTGCATCCCCAGGGCCTGATAT
ACAGCAGAGTGGTGGTACGAAAAGAGCACACAAAAAAATATTTGTTGAGTCAATGAATGAATGAT
TTCCTCAAATAGGATTAGCCTAAAATTTTGGAAACATGAACAGATTTGGATATGTGAAAATTTATTT
CCAGACTGTTCATCAGGAACTGTTAGCAGCTTCTAAAGGGTACACTGGAGCAGCAGTAGTAAAAG
GAGGAAGAGGAGCAGCTCTGCTACTGCTACTATCGAGTACTACTACAATTAGCACTTGCTTATTCT
GTGTGTTAGGCCCTGTACTGAACACTCTGTCTAAATTAGTTCATTTCCTCCTGGAAATGACTCTAGG
GGGTAAGTGCTTCATCATGTAAGATGAGTATTTTCACATTTGTTGTGTCTGAAATCTGAGTGTGT
CTTTCAATGATGGAATCTTTGATTCCATGATAAGTGGTATTATTCCCATTTTAAGGATGAGGAAACT
GAGGTCCAAAGAAATTAAGTAATTTGCCCAAATTCACCCAGCCTAGAAAATGATAAAGCTAGTTCT
AAACCCAAGCAGATTAGCTCTGAAGTCTGGGCCCTTAATAACCACTTTTTATTGCCTATATTTGTAC
CTCTGGTGTACGTATCAAGTTATATGTTGACTTCAAAACTATCATGACCTTTTCTTGGTTTTGATTGT
CCAACATTAGTATAGTGTTCTGGGTCTGCAAAAATTTTGATTACTCATCTCATCTGTAAAACATTTT
GAACTCGTGTGTTTGTGCATGCACATTTGTGTGTAATTATAAAAATTTTACTTTCTGTTAATATATA
AGTTGTATCATAAGAAACTGCCGTTTTTGAAGAGCAAAAAAGGTTGAATGTTACCAGTTACATCT
GGTTCAACCTAATAGACATTTGTACAAAAACAGACATTTTAAGAGGTTGAAATAAAAATTTAATAA
ACAATATTTTCAGTTTTTACTAATTGTGATGCTTCACTATCATTAGCTAATATGTCAAGGCATAATA
TACCTTAGGGTGAACTTTATCATTAACAAAGGTGGATGGTGTCAATAATCTTGAGGTTTGTGTTTTT
TTATATAACACTGCGAGGTCTAATTAAGTACTTACTGTTTACCACCTCATACAGTGGCCGATAAAA
AGTGTCACTTCTGCTGTTTCCTCTGGGTTGTGCTTGAATTATTAGTATTATCTTCAGTCCTCAGTTTC
TTTGTGGGAAACTTTTTAATTAGTTGTTTAATTTTGTAAGATGGTTAGTTTAGTCAAAATTAGATAA
GAGAATTTGAAAATCCGTAGCTACCCAAAGCAACCTACACATAAGAACTATTATTTTTGTGTTTTG
AAATCATAATTTTATTGATTTCCAGTGTTTCCACTGGTAGTGGTTTCATTGATATAGGAGTATCAAA
ACATCACTCATTATTTATTTCAGTTTCATTTGATCCTAGCCGTTTTGTATTAACTCTCTGTGAAGAAA
TTACCTCACAAATCTATTGCTGTCGCTAGCTCGCTACCTTAGGACCGTTATAGTTACTAGCATAACT
TCGTATAGCATACATTATACGAAGTTATCTCGAGCTTGGTAAAGGAATGGAGAATTAAGGCTCTAG
ATCATTAGTGGTTACACTATAGTATTAGAAGTAAAAAAAGATTATACCAACAAAATAAGAACAT
GTTAATGTACTTGTAATGAATAAACATGAATAAAGCTCTTATGCTATATAGGTGCACTAAACAATC
TACTAGAATTGTCAGCAAACTACGTATCTTAATCCTGAAAGGGTCCCAAACCAATGATCTAAAATT
GAATCAAACTTTCTTCCTTGAGCATAATTACTTAAATGATTTATTAAAATAGCCAGCATTTAAAAGC
TTAAAATGTAAATATCATAATGTGGTATCCTAGATAGCATCCCAGAACAGAAAAAGGATATTAGGG
```

Figure 6 (continued)

```
AAAAACTGGAGGAATGGAATAAATTATGCAGTTTAGTTATTAATAATGTACTAACGTCCTTAGTTA
TGACGATTGTACCATGGTAATGTAAGATACTAACAATAGAGGAAACCGGGTAAGGAGTATACAGT
AACTCTATACTATCTTTGCAACTTTTTTGTAAATTTAAAACTTCTAAAATAAAGAACAAATTTAAAC
ATTAAAAAGTATCACCAGGAACATATATCACTGTTTACAGATGAAATACTATGTATTTTCATATCTA
ATTTCTGATCATTGACTTCAAATCAGAAAAGTGAATGACACCTCAAAATCAGGTTTTCTGTTTACTG
AAGTCTAAGAAAAGAAAGCATACCAGCTGGAGAGATTCATGTTTATAAAGACAGATTTATAACAA
CAAAAATAAAATATCCAAGAATAAATTTAAGAAGAAGCACTTTACTGAGAAACATATGAAAACCT
GAACAAATGGAGAGGGATATTTTGTATTTGAATAGAAAGACTTCTGGTTTAAAGATAATTCTCTTT
AAATTATTTTTTGTAGAAATTTAAGGGGTACAAGAGCAGTGTTGTCACATGGATATATTACATAGT
GGTGAAGTCTGGGGTTTTAGTGTAAATTAATCTTTACATTTTGTTTGAGCCCAATAAATGTACCAAC
ATGATTTTTATAGAAAGATAGTCATTCCTATTAATCCAAACTTGTCCCAACTTTGAATTGAATTGAG
GCAGAGCTAGCAGGTGTTCCCCACGGCTGAGGCATCTGAACATTAAGCATATCCCTCTGAGAACCA
GCCTGCATTGATACTCTTTCTAATGTGGACAGCATCAAGCTATGTACGTAGTTCTGTGCTCAGCAAA
AGCCCTGACTTCTTTTGTTTATGTCCTAGCCCCATACAACAAAATCAACCAAAGAATTTGGTTGT
GGATCCAGTCACCTCTGAACATGAACTGACATGTCAGGCTGAGGGCTACCCCAAGGCCGAAGTCAT
CTGGACAAGCAGTGACCATCAAGTCCTGAGTGGTAAGACCACCACCACCAATTCCAAGAGAGAGG
AGAAGCTTTTCAATGTGACCAGCACACTGAGAATCAACACAACAACTAATGAGATTTTCTACTGCA
CTTTTAGGAGATTAGATCCTGAGGAAAACCATACAGCTGAATTGGTCATCCCAGGTAATATTCTGA
ATGTGTCCATTAAAATATGTCTAACACTGTCCCCTAGCACCTAGCATGATGTCTGCCTATCATAGTC
ATTCAGTGATTGTTGAATAAATGAATGAATGAATAACACTATGTTTACAAAATATATCCTAATTCCT
CACCTCCATTCATCCAAACCATATTGTTACTTAATAAACATTCAGCAGATATTTATGGAATATACCT
TTTGTTCCATGCATTGTAGTACTCATTGGATACACATAGAATAATAAGACTCAGTTCACACTCTTCA
GGAAACAGATAAAAAACTAAGAAACAAACAAAAAACAGGCAATCCAACACCATGTGGGAAATGC
TTTCATAGCCGGGAAACCTGGGGAATACCTGAGAGGAATACTCAATTCAGGCCTTGTTTCAGGAAT
CCAAATCCTGGCACATCAGAGCTGCTTCCCTCTTTCCAGGGTGGCAGGAAATAAATGGAACATATT
TTTCTATCTTATGCCAAACATGAGGGACCCTTTCTCCCCGGTGCCTCTCCCAAGGTAGTCTACAATA
TTTCAACTCTAGCAGTCTGCTTAGTGCATAGAACATGAGGCTGTGTGTCCCTGGGCAAATTACTAG
ACTTCTGTGTGCTTCACTTTCCCTGTAGGATTATAATCTACTGAGCAAGCTTATTGTAAGGGTCAGA
TTAGCAACAGTGTATGAAAATGATTTGAGACCATTGCCTGCACAAATTCAACTATTTTTTTTATCT
CACTACTCTACAGAAGTAGGTAGGGTGGGAGACAGAGTCTGATGAGAGGCTCAGAATGTGAAAGA
AAGTGAGGCGAGTGAGCATGATATTTAATATAAACACAAAGATATTCTGAGAAGAGCTGCTCACT
GCCCCCTCCCCAATACATGTTGATAGGAAAATGCCACGTACTTCAGCAAAAACAACTGAAAAATT
AGATAGAAAAGTCAATCAATAGGAAAAGATAATCCAGGACGGTGTTGTGAACAGAAAGAGGGGG
AAAAAACTTTAGAAAATGATGGGGATGCTCTTACTGGGGTACGAGTCCTCAGGTATTGAACTGGCT
TTCAGTAAAAGCTAGATTAGTGGGTTCCTGCCATTTACAAGCTGTTTTATGACAACTTACTTGTTGG
GTGGCCTACAGTAACTCACCTAACTGCACTGAGTCTGTTTCCTCATCTGTAAATTGGGGATTTTTTT
TTAAATACCTGGCATGCCTAACTCATAAAGTTGTTCTGAAACTGAAATAAAACATACGTGAACAGG
CATTGTAAACTGTAAGTTACGGAAAAGCTGGCTGTTGTTGTGTCTTTAAAGTTTCACCTGGGTAGT
CAAAGATGGATCATGGGTCTCAGTGGAGAGCTGAGCCAGGCAGGAGCTGACTAAGGGTGAGAGGT
GGGAGTTAGCAGCCTCTGAACATCTGTGTACCATGGGACCCCCTTTCCTCCTGCATGGTACCCCAG
ACAAGGAGCCTAGTAAGAGATACTAATGGCTTGTTGTCCAGAGATGTTCAAACTGCAGAGAAAGA
TAAGACAACAAGCATTGGCCTCCAATCATGATGACAGATAGGAGGAGGTGGGAGCTCCTTAGCAG
TGCTGGTTGGCCTTCCATGTTCTACTGTGGCCATCTCTGCCATGTACTGTAGGCTACTAGCTTCTAT
ATTAAAGAATGCAAGAGGGGCCAGGAGCGGAGGCTCATGCCTGTAATCTCAGCACTTTGGGAGGC
CAAGGTGGGCAGATCACTTGAGGTCAGGAGTTTGTGACCAGCCTGGCCAACATGGTGAAACTCTGC
CTTTACTAAAATATAAAAATTAGCTGGGTGTGGTGGTGTGCACCTGTAATCCCAGCTACTCGGGA
GACTGAGGCACAAGAATTGCTTGAACCTGGGAGGCGGAAGTTGCAGTGAGCCCAGATTGCGCCAC
TGCACTCCACCCTGGGCAACAGAGAAAGACTCTGCCTCAAAAAAAAAAAAAAAAGCAAGAGGA
AGTGAAATAATCAAGGCCGCCATTTAATAGTGAGCAGCCACTCCATGTGGTACTGTGCAAGCACAT
TATAAATATTAGCCTCACAAGAAATGTATTAGCATTTGTATTTTGTACACTGGTTAAGTATCTTGCC
CAAGACCTCAAAACTGGTTAAGGGCAGCAGAATTTAGCCCCAGCACCACCTTTTCAAAGCCTGGGC
TTCTCACACTTCTCCATGCTGTTCCCATTTTAACACAGGTATCTCGCCATTCCAGCCACTCAAACTTT
GGCATTTAAGAAAATTATCCTAAAGCTAAACTAAACTTCAAGGATGACCATTCTCCTGACCCCTTC
```

Figure 6 (continued)

CCATCAAAATTTTATCTTTAGTCAGTTTGTTTTCGTTTTGTTTTGTTTTTCAGAACTACCTCTGGCAC
ATCCTCCAAATGAAAGG (SEQ ID NO:8)

Humanization fragment C
GTCACGGTTCCCAAGGACCTATATGTGGTAGAGTATGGTAGCAATATGACAATTGAATGCAAATTC
CCAGTAGAAAAACAATTAGACCTGGCTGCACTAATTGTCTATTGGGAAATGGAGGATAAGAACATT
ATTCAATTTGTGCATGGAGAGGAAGACCTGAAGGTTCAGCATAGTAGCTACAGACAGAGGGCCCG
GCTGTTAAGGACCAGCTCTCCCTGGGAAATGCTGCACTTCAGATCACAGATGTGAAATTGCAGGA
TGCAGGGGTGTACCGCTGCATGATCAGCTATGGTGGTGCCGACTACAAGCGAATTACTGTGAAAGT
CAATGGTAAGAATTATTATAGATGAGAGGCCTGATCTTTATTGAAAACATATTCCAAGTGTTGAAG
ACTTTTCATTCTTGTAAGTCCATACTTATTTTCAAACAGAACAGCATAGTCTGTTCATTCATTCATTC
AATTCATGAATTCATTCACATAATTATCCAATTTCTTGAGCACCTATTTGATAGTCACTGGAAATCC
AGAGACAAACAACACAGAGCCATGTTCTACAGTATGTACAGTTTTCCAAAAAGAATTTCTAGTCTT
TACTTTTTTATTACAAATGGAATACGTATACTTGCAAATAATTCAGATACTGTGGAAGAGATCAAA
TGAATTGCAAAGTGTCCCTCCTCCCTTCACCACTATCTCCATGGCATGCAGAGAGAGTAACCATT
ATTTGTGTGTCCCTCCAGAAATTTTTTATTCAACTACTATTTTTTATTTTATTAGGTCCGTCAGTTT
TCCTTTTTTGAGCCTCTCTATATCAAATGCAAATAAATATATTCAGAACAAACCCCACTGTAAGGTT
CACATTAAAAAAGACTTGAAGTCACCCTATGAAGACAAAAAATAATCACATTAAGTGTGAAAGAA
CCTATTCTTCCAGTACAGGATAAGCCATACTTACTGGGCATATATTCATCTTGAAAATCTATACTGA
TGTTGTCTTGGGGAATTGAAAAGGAACTAGGAGTGTTAGTTCCTCGGTATTGACCCACAGTTATGTT
ATCAGGTCACTTGAGTTCAAAGTTTTGTGTTGGCACTAGCTAAGTAAAGGAAAACACCTCTGCTTTC
ATTGTTGAGTTTCACAGAATTGAGAGCTGAAAGGATCCCAGGCAGGAGCAGCTAATCCAAACTCCC
ACAAAGAACAAAAATCCCCAGAGGATCTTCTGTTCTTATATTTCCTGCAATGGCGTCCCTGTCATA
TCCCACAATGGCCTCCCTGCCATTTGGATATCCCTTCCATATCCTGTTGAAATTACTCCCTAATAGT
AAGCTGAAATCTGCCCCTCTAGTTGTAGTCTTGGGATTATTTCATTTACATGATGACCTTTTAATATT
TGACTAGAATTAAATCATCTCCCCTTGGTCTTTCCATTCCTGGGCTAACTACCATCAATCTGAGGGC
TAACAATACAAGTAGAAAAAGTATACATTTGTCACTGATCACTGATCAATTATTAATCAATGATCA
CTGATAACTATAAACTCAAAAACAAAATCATGTGGGGATTAAGAGAAATGTATCAGTTTTATGTTG
TATTTCTGGTCCCTGATACTGGCTCAGGTAATGCCACTATTGTCAAGAAGATACCACTTGTAAAGTA
GATTTAATTTTCATTATATTTTACCATATGCTTCTCCATTCATGACATCTCTTGAGATGTTGTGGTTT
ATACTTTCAGTTTTTCTCCAGTCCATCCGCAAATATCAGGCATCTACTGTGTTCCAAGATATTAAAG
AAATCATCATGACTTAGCCTCATCAACAGCATTGCTAGATCTGGGATGGAAAGGAAGAGTATAATC
CTGGCAGTCAGGAAGAAGGCAGCATAAAGTATAAGTTTCTGCTTCCAAAAAAGGTCTCTCATCAGC
CTGTAGGGAGTGTGTAGGGAAGGGACAGCTGTCCTTGTAGTAGGGAAGGGTTTTATTCAGGTCGTC
TGGGCTCCATAATATCCCTTGTGTATCTGCAGTCTCCTTTGCCATGGATCAACACAATAGGAAATCT
TCCGGCACTGATGGTTTTTCCAAGGGGAGTTCTTCCTGGAGCAAAGCAAATGACCAACCAGGTTT
GAGGACCTGATTTGTTTGACAATTCCATTTTGTATTGTAAATTACTTAATTGGCATTCTACTCCCAAT
CCATCTTGTCATTTGCATACAGTGGTTTTGGGATTGAGTTCAGCTATACCAAAAGTCTGAACCTTCT
GCACTTAGAACAAGGCAACCACCAAGCTTCACTTGCACTGAGGCCGTGTCTCCAATGGAAATGAGG
CAGCTGGCTTGCAGGAGCTTCCCAACTCAGGGAAGTAGAACTCCTGAGTCACCTCCATATGCAAAT
GATTTCACAGTAATGCTGTTGAACTTCACTTCCCATCACAGCAAATGTGTGGTAACATAGCTTCCCC
ACAGGAGTTTACTCACCATGGTATTTTAAAGGTGAAACATTTCAAAACTGAAATTTGAAAGAATTT
AGTTTTGGATTCACTCAATTATCACTATCACTTCGGGTGTTATTGCACCTTTCTTGTTTGTGAGTTTA
AATGCCAGACTCTCAGGCCACTAACTTTCAATTAAAAGTGTTTTTCTTTAATCGCTGAACCTAACAG
CAGGGAAAACGAAATGTTCATTCAGACTTTCAGAACCTTCAATGAGATTAGGCAGCTGAAAGATCA
AAGTGTTGCATAGTTGTCCCGATAAAGCTATTTGGATCATATGGACCAAATCGACTGCTGTCATTCC
CCACCAACCCCATCTCTCCCCAAAATTCCCAGCCCTGTTTAAGTGTTCTCTGTAGCATTTATCTCTAT
CTAGTATATTGTGTAGCATATCATATCATACTTTTCTGTTTTGTTTATTGTCTCTCTCCTCCTAGAAT
ATAAACTCCACAAGCACAAAGATTTGGGCCTGTTTATAATATTGTTGCATCCCAGGGCCTGATAT
ACAGCAGAGTGGTGGTACGAAAGAGCACACAAAAAAATATTTGTTGAGTCAATGAATGAATGAT
TTCCTCAAATAGGATTAGCCTAAAATTTTGGAAACATGAACAGATTTGGATATGTGAAAATTTATTT
CCAGACTGTTCATCAGGAACTGTTAGCAGCTTCTAAAGGGTACACTGGAGCAGCAGTAGTAAAAG
GAGGAAGAGGAGCAGCTCTGCTACTGCTACTATCGAGTACTACTACAATTAGCACTTGCTTATTCT

Figure 6 (continued)

GTGTGTTAGGCCCTGTACTGAACACTCTGTCTAAATTAGTTCATTTCCTCCTGGAAATGACTCTAGG
GGGTAAGTGCTTCATCATGTAAGATGAGTATTTTTCACATTTTGTTGTGTCTGAAATCTGAGTGTGT
CTTTCAATGATGGAATCTTTGATTCCATGATAAGTGGTATTATTCCCATTTTAAGGATGAGGAAACT
GAGGTCCAAAGAAATTAAGTAATTTGCCCAAATTCACCCAGCCTAGAAAATGATAAAGCTAGTTCT
AAACCCAAGCAGATTAGCTCTGAAGTCTGGGCCCTTAATAACCACTTTTTATTGCCTATATTTGTAC
CTCTGGTGTACGTATCAAGTTATATGTTGACTTCAAAACTATCATGACCTTTTCTTGGTTTTGATTGT
CCAACATTAGTATAGTGTTCTGGGTCTGCAAAAATTTTGATTACTCATCTCATCTGTAAAACATTTT
GAACTCGTGTGTTTGTGCATGCACATTTGTGTGTAATTATAAAAATTTTACTTTCTGTTAATATATA
AGTTGTATCATAAGAAACTGCCGTTTTTGAAGAGCAAAAAAGGTTGAATGTTACCAGTTACATCT
GGTTCAACCTAATAGACATTTGTACAAAAACAGACATTTTAAGAGGTTGAAATAAAAATTTAATAA
ACAATATTTTCAGTTTTTACTAATTGTGATGCTTCACTATCATTAGCTAATATGTCAAGGCATAATA
TACCTTAGGGTGAACTTTATCATTAACAAAGGTGGATGGTGTCAATAATCTTGAGGTTTGTGTTTTT
TTATATAACACTGCGAGGTCTAATTAAGTACTTACTGTTTACCACCTCATACAGTGGCCGATAAAA
AGTGTCACTTCTGCTGTTTCCTCTGGGTTGTGCTTGAATTATTAGTATTATCTTCAGTCCTCAGTTTC
TTTGTGGGAAACTTTTTAATTAGTTGTTTAATTTTGTAAGATGGTTAGTTTAGTCAAAATTAGATAA
GAGAATTTGAAAATCCGTAGCTACCCCAAAGCAACCTACACATAAGAACTATTATTTTGTGTTTTG
AAATCATAATTTTATTGATTTCCAGTGTTTCCACTGGTAGTGGTTTCATTGATATAGGAGTATCAAA
ACATCACTCATTATTTATTTCAGTTTCATTTGATCCTAGCCGTTTTGTATTAACTCTCTGTGAAGAAA
TTACCTCACAAATCTATTGCTGTC (SEQ ID NO:9)

Humanization fragment D
CTTGGTAAAGGAATGGAGAATTAAGGCTCTAGATCATTAGTGGTTACACTATAGTATTAGAAGTAA
AAAAAAGATTATACCAACAAAATAAGAACATGTTAATGTACTTGTAATGAATAAACATGAATAAA
GCTCTTATGCTATATAGGTGCACTAAACAATCTACTAGAATTGTCAGCAAACTACGTATCTTAATCC
TGAAAGGGTCCCAAACCAATGATCTAAAATTGAATCAAACTTTCTTCCTTGAGCATAATTACTTAA
ATGATTTATTAAAATAGCCAGCATTTAAAAGCTTAAAATGTAAATATCATAATGTGGTATCCTAGA
TAGCATCCAGAACAGAAAAAGGATATTAGGGAAAAACTGGAGGAATGGAATAAATTATGCAGTT
TAGTTATTAATAATGTACTAACGTCCTTAGTTATGACGATTGTACCATGGTAATGTAAGATACTAAC
AATAGAGGAAACCGGGTAAGGAGTATACAGTAACTCTATACTATCTTTGCAACTTTTTGTAAATTT
AAAACTTCTAAAATAAAGAACAAATTTAAACATTAAAAAGTATCACCAGGAACATATATCACTGTT
TACAGATGAAATACTATGTATTTTCATATCTAATTTCTGATCATTGACTTCAAATCAGAAAAGTGAA
TGACACCTCAAAATCAGGTTTTCTGTTTACTGAAGTCTAAGAAAAGAAAGCATACCAGCTGGAGAG
ATTCATGTTTATAAAGACAGATTTATAACAACAAAAATAAAATATCCAAGAATAAATTTAAGAAGA
AGCACTTTACTGAGAAACATATGAAAACCTGAACAAATGGAGAGGGATATTTTGTATTTGAATAGA
AAGACTTCTGGTTTAAAGATAATTCTCTTTAAATTATTTTTTGTAGAAATTTAAGGGGTACAAGAGC
AGTGTTGTCACATGGATATATTACATAGTGGTGAAGTCTGGGGTTTTAGTGTAAATTAATCTTTACA
TTTTGTTTGAGCCCAATAAATGTACCAACATGATTTTTATAGAAAGATAGTCATTCCTATTAATCCA
AACTTGTCCCAACTTTGAATTGAATTGAGGCAGAGCTAGCAGGTGTTCCCCACGGCTGAGGCATCT
GAACATTAAGCATATCCCTCTGAGAACCAGCCTGCATTGATACTCTTTCTAATGTGGACAGCATCA
AGCTATGTACGTAGTTCTGTGCTCAGCAAAAGCCCTGACTTCTTTTTGTTTATGTCCTAGCCCCATA
CAACAAAATCAACCAAAGAATTTTGGTTGTGGATCCAGTCACCTCTGAACATGAACTGACATGTCA
GGCTGAGGGCTACCCCAAGGCCGAAGTCATCTGGACAAGCAGTGACCATCAAGTCCTGAGTGGTA
AGACCACCACCACCAATTCCAAGAGAGAGGAGAAGCTTTTCAATGTGACCAGCACACTGAGAATC
AACACAACAACTAATGAGATTTTCTACTGCACTTTTAGGAGATTAGATCCTGAGGAAAACCATACA
GCTGAATTGGTCATCCCAGGTAATATTCTGAATGTGTCCATTAAAATATGTCTAACACTGTCCCCTA
GCACCTAGCATGATGTCTGCCTATCATAGTCATTCAGTGATTGTTGAATAAATGAATGAATA
ACACTATGTTACAAAATATATCCTAATTCCTCACCTCCATTCATCCAAACCATATTGTTACTTAAT
AAACATTCAGCAGATATTTATGGAATATACCTTTGTTCCATGCATTGTAGTACTCATTGGATACAC
ATAGAATAATAAGACTCAGTTCACACTCTTCAGGAAACAGATAAAAAACTAAGAAACAAACAAAA
AACAGGCAATCCAACACCATGTGGGAAATGCTTTCATAGCCGGGAAACCTGGGGAATACCTGAGA
GGAATACTCAATTCAGGCCTTGTTTCAGGAATCCAAATCCTGGCACATCAGAGCTGCTTCCCTCTTT
CCAGGGTGGCAGGAAATAAATGGAACATATTTTTCTATCTTATGCCAAACATGAGGGACCCTTTCT
CCCCGGTGCCTCTCCCAAGGTAGTCTACAATATTTCAACTCTAGCAGTCTGCTTAGTGCATAGAACA

Figure 6 (continued)

TGAGGCTGTGTGTCCCTGGGCAAATTACTAGACTTCTGTGTGCTTCACTTTCCCTGTAGGATTATAA
TCTACTGAGCAAGCTTATTGTAAGGGTCAGATTAGCAACAGTGTATGAAAATGATTTGAGACCATT
GCCTGCACAAATTCAACTATTTTTTTTTATCTCACTACTCTACAGAAGTAGGTAGGGTGGGAGACAG
AGTCTGATGAGAGGCTCAGAATGTGAAAGAAAGTGAGGCGAGTGAGCATGATATTTAATATAAAC
ACAAAGATATTCTGAGAAGAGCTGCTCACTGCCCCCTCCCCAATACATGTTGATAGGAAAATGCC
ACGTACTTCAGCAAAAACAACTGAAAAATTAGATAGAAAAGTCAATCAATAGGAAAAGATAATCC
AGGACGGTGTTGTGAACAGAAAGAGGGGGAAAAAACTTTAGAAAATGATGGGGATGCTCTTACTG
GGGTACGAGTCCTCAGGTATTGAACTGGCTTTCAGTAAAAGCTAGATTAGTGGGTTCCTGCCATTT
ACAAGCTGTTTATGACAACTTACTTGTTGGGTGGCCTACAGTAACTCACCTAACTGCACTGAGTCT
GTTTCCTCATCTGTAAATTGGGGATTTTTTTTTAAATACCTGGCATGCCTAACTCATAAGTTGTTCT
GAAACTGAAATAAAACATACGTGAACAGGCATTGTAAACTGTAAGTTACGGAAAAAGCTGGCTGT
TGTTGTGTCTTTAAAGTTTCACCTGGGTAGTCAAAGATGGATCATGGGTCTCAGTGGAGAGCTGAG
CCAGGCAGGAGCTGACTAAGGGTGAGAGGTGGGAGTTAGCAGCCTCTGAACATCTGTGTACCATG
GGACCCCCTTTCCTCCTGCATGGTACCCCAGACAAGGAGCCTAGTAAGAGATACTAATGGCTTGTT
GTCCAGAGATGTTCAAACTGCAGAGAAAGATAAGACAACAAGCATTGGCCTCCAATCATGATGAC
AGATAGGAGGAGGTGGGAGCTCCTTAGCAGTGCTGGTTGGCCTTCCATGTTCTACTGTGGGCCATC
TCTGCCATGTACTGTAGGCTACTAGCTTCTATATTAAAGAATGCAAGAGGGGCCAGGAGCGGAGGC
TCATGCCTGTAATCTCAGCACTTTGGGAGGCCAAGGTGGGCAGATCACTTGAGGTCAGGAGTTTGT
GACCAGCCTGGCCAACATGGTGAAACTCTGCCTTTACTAAAAATATAAAAATTAGCTGGGTGTGGT
GGTGTGCACCTGTAATCCCAGCTACTCGGGAGACTGAGGCACAAGAATTGCTTGAACCTGGGAGGC
GGAAGTTGCAGTGAGCCCAGATTGCGCCACTGCACTCCACCCTGGGCAACAGAGAAAGACTCTGC
CTCAAAAAAAAAAAAAAAAGCAAGAGGAAGTGAAATAATCAAGGCCGCCATTTAATAGTGAGC
AGCCACTCCATGTGGTACTGTGCAAGCACATTATAAATATTAGCCTCACAAGAAATGTATTAGCAT
TTGTATTTTGTACACTGGTTAAGTATCTTGCCCAAGACCTCAAAACTGGTTAAGGGCAGCAGAATTT
AGCCCCAGCACCACCTTTTCAAAGCCTGGGCTTCTCACACTTCTCCATGCTGTTCCCATTTTAACAC
AGGTATCTCGCCATTCCAGCCACTCAAACTTTGGCATTTAAGAAAATTATCCTAAAGCTAAACTAA
ACTTCAAGGATGACCATTCTCCTGACCCCTTCCCATCAAAATTTTATCTTTAGTCAGTTTGTTTTCGT
TTTGTTTTGTTTTCAGAACTACCTCTGGCACATCCTCCAAATGAAAGG (SEQ ID NO:10)

Humanization fragment E
GTCACGGTTCCCAAGGACCTATATGTGGTAGAGTATGGTAGCAATATGACAATTGAATGCAAATTC
CCAGTAGAAAAACAATTAGACCTGGCTGCACTAATTGTCTATTGGGAAATGGAGGATAAGAACATT
ATTCAATTTGTGCATGGAGAGGAAGACCTGAAGGTTCAGCATAGTAGCTACAGACAGAGGGCCCG
GCTGTTGAAGGACCAGCTCTCCCTGGGAAATGCTGCACTTCAGATCACAGATGTGAAATTGCAGGA
TGCAGGGGTGTACCGCTGCATGATCAGCTATGGTGGTGCCGACTACAAGCGAATTACTGTGAAAGT
CAATGGTAAGAATTATTATAGATGAGAGGCCTGATCTTTATTGAAAACATATTCCAAGTGTTGAAG
ACTTTTCATTCTTGTAAGTCCATACTTATTTTCAAACAGAACAGCATAGTCTGTTCATTCATTCATTC
AATTCATGAATTCATTCACATAATTATCCAATTTCTTGAGCACCTATTTGATAGTCACTGGAAATCC
AGAGACAAACAACACAGAGCCATGTTCTACAGTATGTACAGTTTCCAAAAAGAATTTCTAGTCTT
TACTTTTTATTACAAATGGAATACGTATACTTGCAAATAATTCAGATACTGTGGAAGAGATCAAA
TGAATTGCAAAAGTGTCCCTCCTCCCTTCACCACTATCTCCCATGGCATGCAGAGAGAGTAACCATT
ATTTGTGTGTCCCTCCAGAAATTTTTTATTCAACTACTATTTTTTATTTTATTAGGTCCGTCAGTTT
TCCTTTTTTGAGCCTCTCTATATCAAATGCAAATAAATATATTCAGAACAAACCCCACTGTAAGGTT
CACATTAAAAAGACTTGAAGTCACCCTATGAAGACAAAAAATAATCACATTAAGTGTGAAAGAA
CCTATTCTTCCAGTACAGGATAAGCCATACTTACTGGGCATATATTCATCTTGAAAATCTATACTGA
TGTTGTCTTGGGGAATTGAAAAGGAACTAGGAGTGTTAGTTCCTCGGTATTGACCCACAGTTATGTT
ATCAGGTCACTTGAGTTCAAAGTTTTGTGTTGGCACTAGCTAAGTAAAGGAAAACACCTCTGCTTTC
ATTGTTGAGTTTCACAGAATTGAGAGCTGAAAGGATCCCAGGCAGGAGCAGCTAATCCAAACTCCC
ACAAAGAACAAAAATCCCCAGAGGATCTTCTGTTCTTATATTCCTGCAATGGCGTCCCTGTCATA
TCCCACAATGGCCTCCCTGCCATTTGGATATCCCTTCCATATCCTGTTGAATTACTCCCTAATAGT
AAGCTGAAATCTGCCCCTCTAGTTGTAGTCTTGGGATTATTTCATTTACATGATGACCTTTTAATATT
TGACTAGAATTAAATCATCTCCCCTTGGTCTTTCCATTCCTGGGCTAACTACCATCAATCTGAGGGC
TAACAATACAAGTAGAAAAAGTATACATTTGTCACTGATCACTGATCAATTATTAATCAATGATCA

Figure 6 (continued)

```
CTGATAACTATAAACTCAAAAACAAAATCATGTGGGATTAAGAGAAATGTATCAGTTTTATGTTG
TATTTCTGGTCCCTGATACTGGCTCAGGTAATGCCACTATTGTCAAGAAGATACCACTTGTAAAGTA
GATTTAATTTTCATTATATTTTACCATATGCTTCTCCATTCATGACATCTCTTGAGATGTTGTGGTTT
ATACTTTCAGTTTTTCTCCAGTCCATCCGCAAATATCAGGCATCTACTGTGTTCCAAGATATTAAAG
AAATCATCATGACTTAGCCTCATCAACAGCATTGCTAGATCTGGGATGGAAAGGAAGAGTATAATC
CTGGCAGTCAGGAAGAAGGCAGCATAAAGTATAAGTTTCTGCTTCCAAAAAAGGTCTCTCATCAGC
CTGTAGGGAGTGTGTAGGGAAGGGACAGCTGTCCTTGTAGTAGGGAAGGGTTTTATTCAGGTCGTC
TGGGCTCCATAATATCCCTTGTGTATCTGCAGTCTCCTTTGCCATGGATCAACACAATAGGAAATCT
TCCGGCACTGATGGTTTTTCCAAGGGGGAGTTCTTCCTGGAGCAAAGCAAATGACCAACCAGGTTT
GAGGACCTGATTTGTTTGACAATTCCATTTTGTATTGTAAATTACTTAATTGGCATTCTACTCCCAAT
CCATCTTGTCATTTGCATACAGTGGTTTTGGGATTGAGTTCAGCTATACCAAAAGTCTGAACCTTCT
GCACTTAGAACAAGGCAACCACCAAGCTTCACTTGCACTGAGGCCGTGTCTCCAATGGAAATGAGG
CAGCTGGCTTGCAGGAGCTTCCCAACTCAGGGAAGTAGAACTCCTGAGTCACCTCCATATGCAAAT
GATTTCACAGTAATGCTGTTGAACTTCACTTCCCATCACAGCAAATGTGTGGTAACATAGCTTCCCC
ACAGGAGTTTACTCACCATGGTATTTTAAAGGTGAAACATTTCAAAACTGAAATTTGAAAGAATTT
AGTTTTGGATTCACTCAATTATCACTATCACTTCGGGTGTTATTGCACCTTTCTTGTTTGTGAGTTTA
AATGCCAGACTCTCAGGCCACTAACTTTCAATTAAAAGTGTTTTTCTTTAATCGCTGAACCTAACAG
CAGGGAAAACGAAATGTTCATTCAGACTTTCAGAACCTTCAATGAGATTAGGCAGCTGAAAGATCA
AAGTGTTGCATAGTTGTCCCGATAAAGCTATTTGGATCATATGGACCAAATCGACTGCTGTCATTCC
CCACCAACCCCATCTCTCCCAAAATTCCCAGCCCTGTTTAAGTGTTCTCTGTAGCATTTATCTCTAT
CTAGTATATTGTGTAGCATATCATATCATACTTTTCTGTTTTGTTTATTGTCTCTCTCCTCCTAGAAT
ATAAACTCCACAAGCACAAAGATTTGGGCCTGTTTTATAATATTGTTGCATCCCCAGGGCCTGATAT
ACAGCAGAGTGGTGGTACGAAAGAGCACACAAAAAAATATTTGTTGAGTCAATGAATGAATGAT
TTCCTCAAATAGGATTAGCCTAAAATTTTGGAAACATGAACAGATTTGGATATGTGAAAATTTATTT
CCAGACTGTTCATCAGGAACTGTTAGCAGCTTCTAAAGGGTACACTGGAGCAGCAGTAGTAAAAG
GAGGAAGAGGAGCAGCTCTGCTACTGCTACTATCGAGTACTACTACAATTAGCACTTGCTTATTCT
GTGTGTTAGGCCCTGTACTGAACACTCTGTCTAAATTAGTTCATTTCCTCCTGGAAATGACTCTAGG
GGGTAAGTGCTTCATCATGTAAGATGAGTATTTTCACATTTTGTTGTGTCTGAAATCTGAGTGTGT
CTTTCAATGATGGAATCTTTGATTCCATGATAAGTGGTATTATTCCCATTTTAAGGATGAGGAAACT
GAGGTCCAAAGAAATTAAGTAATTTGCCCAAATTCACCCAGCCTAGAAAATGATAAAGCTAGTTCT
AAACCCAAGCAGATTAGCTCTGAAGTCTGGGCCCTTAATAACCACTTTTTATTGCCTATATTTGTAC
CTCTGGTGTACGTATCAAGTTATATGTTGACTTCAAAACTATCATGACCTTTCTTGGTTTTGATTGT
CCAACATTAGTATAGTGTTCTGGGTCTGCAAAAATTTTGATTACTCATCTCATCTGTAAACATTTT
GAACTCGTGTGTTTGTGCATGCACATTTGTGTGTAATTATAAAAATTTTACTTTCTGTTAATATATA
AGTTGTATCATAAGAAACTGCCGTTTTTGAAGAGCAAAAAAGGTTGAATGTTACCAGTTACATCT
GGTTCAACCTAATAGACATTTGTACAAAAACAGACATTTTAAGAGGTTGAAATAAAAATTTAATAA
ACAATATTTTCAGTTTTTACTAATTGTGATGCTTCACTATCATTAGCTAATATGTCAAGGCATAATA
TACCTTAGGGTGAACTTTATCATTAACAAAGGTGGATGGTGTCAATAATCTTGAGGTTTGTGTTTTT
TTATATAACACTGCGAGGTCTAATTAAGTACTTACTGTTACCACCTCATACAGTGGCCGATAAAA
AGTGTCACTTCTGCTGTTTCCTCTGGGTTGTGCTTGAATTATTAGTATTATCTTCAGTCCTCAGTTTC
TTTGTGGGAAACTTTTTAATTAGTTGTTTAATTTTGTAAGATGGTTAGTTTAGTCAAAATTAGATAA
GAGAATTTGAAAATCCGTAGCTACCCCAAAGCAACCTACACATAAGAACTATTATTTTGTGTTTTG
AAATCATAATTTTATTGATTTCCAGTGTTTCCACTGGTAGTGGTTTCATTGATATAGGAGTATCAAA
ACATCACTCATTATTTATTTCAGTTTCATTTGATCCTAGCCGTTTTGTATTAACTCTCTGTGAAGAAA
TTACCTCACAAATCTATTGCTGTCCTTGGTAAAGGAATGGAGAATTAAGGCTCTAGATCATTAGTG
GTTACACTATAGTATTAGAAGTAAAAAAAAGATTATACCAACAAAATAAGAACATGTTAATGTACT
TGTAATGAATAAACATGAATAAAGCTCTTATGCTATATAGGTGCACTAAACAATCTACTAGAATTG
TCAGCAAACTACGTATCTTAATCCTGAAAGGGTCCCAAACCAATGATCTAAAATTGAATCAAACTT
TCTTCCTTGAGCATAATTACTTAAATGATTTATTAAAATAGCCAGCATTTAAAAGCTTAAAATGTAA
ATATCATAATGTGGTATCCTAGATAGCATCCCAGAACAGAAAAAGGATATTAGGGAAAAACTGGA
GGAATGGAATAAATTATGCAGTTTAGTTATTAATAATGTACTAACGTCCTTAGTTATGACGATTGTA
CCATGGTAATGTAAGATACTAACAATAGAGGAAACCGGGTAAGGAGTATACAGTAACTCTATACT
ATCTTTGCAACTTTTTTGTAAATTTAAAACTTCTAAAATAAAGAACAAATTTAAACATTAAAAAGTA
```

Figure 6 (continued)

```
TCACCAGGAACATATATCACTGTTTACAGATGAAATACTATGTATTTTCATATCTAATTTCTGATCA
TTGACTTCAAATCAGAAAAGTGAATGACACCTCAAAATCAGGTTTTCTGTTTACTGAAGTCTAAGA
AAAGAAAGCATACCAGCTGGAGAGATTCATGTTTATAAAGACAGATTTATAACAACAAAAATAAA
ATATCCAAGAATAAATTTAAGAAGAAGCACTTTACTGAGAAACATATGAAAACCTGAACAAATGG
AGAGGGATATTTTGTATTTGAATAGAAAGACTTCTGGTTTAAAGATAATTCTCTTTAAATTATTTT
TGTAGAAATTTAAGGGGTACAAGAGCAGTGTTGTCACATGGATATATTACATAGTGGTGAAGTCTG
GGGTTTTAGTGTAAATTAATCTTTACATTTTGTTTGAGCCCAATAAATGTACCAACATGATTTTAT
AGAAAGATAGTCATTCCTATTAATCCAAACTTGTCCCAACTTTGAATTGAATTGAGGCAGAGCTAG
CAGGTGTTCCCCACGGCTGAGGCATCTGAACATTAAGCATATCCCTCTGAGAACCAGCCTGCATTG
ATACTCTTTCTAATGTGGACAGCATCAAGCTATGTACGTAGTTCTGTGCTCAGCAAAAGCCCTGACT
TCTTTTTGTTTATGTCCTAGCCCCATACAACAAAATCAACCAAAGAATTTTGGTTGTGGATCCAGTC
ACCTCTGAACATGAACTGACATGTCAGGCTGAGGGCTACCCCAAGGCCGAAGTCATCTGGACAAG
CAGTGACCATCAAGTCCTGAGTGGTAAGACCACCACCACCAATTCCAAGAGAGAGGAGAAGCTTT
TCAATGTGACCAGCACACTGAGAATCAACACAACAACTAATGAGATTTTCTACTGCACTTTTAGGA
GATTAGATCCTGAGGAAAACCATACAGCTGAATTGGTCATCCCAGGTAATATTCTGAATGTGTCCA
TTAAAATATGTCTAACACTGTCCCCTAGCACCTAGCATGATGTCTGCCTATCATAGTCATTCAGTGA
TTGTTGAATAAATGAATGAATGAATAACACTATGTTTACAAAATATATCCTAATTCCTCACCTCCAT
TCATCCAAACCATATTGTTACTTAATAAACATTCAGCAGATATTTATGGAATATACCTTTGTTCCA
TGCATTGTAGTACTCATTGGATACACATAGAATAATAAGACTCAGTTCACACTCTTCAGGAAACAG
ATAAAAAACTAAGAAACAAACAAAAAACAGGCAATCCAACACCATGTGGGAAATGCTTTCATAGC
CGGGAAACCTGGGGAATACCTGAGAGGAATACTCAATTCAGGCCTTGTTTCAGGAATCCAAATCCT
GGCACATCAGAGCTGCTTCCCTCTTTCCAGGGTGGCAGGAAATAAATGGAACATATTTTTCTATCTT
ATGCCAAACATGAGGGACCCTTTCTCCCCGGTGCCTCTCCCAAGGTAGTCTACAATATTTCAACTCT
AGCAGTCTGCTTAGTGCATAGAACATGAGGCTGTGTGTCCCTGGGCAAATTACTAGACTTCTGTGT
GCTTCACTTTCCCTGTAGGATTATAATCTACTGAGCAAGCTTATTGTAAGGGTCAGATTAGCAACAG
TGTATGAAAATGATTTGAGACCATTGCCTGCACAAATTCAACTATTTTTTTTATCTCACTACTCTAC
AGAAGTAGGTAGGGTGGGAGACAGAGTCTGATGAGAGGCTCAGAATGTGAAAGAAAGTGAGGCG
AGTGAGCATGATATTTAATATAAACACAAAGATATTCTGAGAAGAGCTGCTCACTGCCCCCTCCCC
CAATACATGTTGATAGGAAAATGCCACGTACTTCAGCAAAAACAACTGAAAAATTAGATAGAAAA
GTCAATCAATAGGAAAAGATAATCCAGGACGGTGTTGTGAACAGAAAGAGGGGGAAAAAACTTTA
GAAAATGATGGGGATGCTCTTACTGGGGTACGAGTCCTCAGGTATTGAACTGGCTTTCAGTAAAAG
CTAGATTAGTGGGTTCCTGCCATTTACAAGCTGTTTTATGACAACTTACTTGTTGGGTGGCCTACAG
TAACTCACCTAACTGCACTGAGTCTGTTTCCTCATCTGTAAATTGGGGATTTTTTTTAAATACCTGG
CATGCCTAACTCATAAAGTTGTTCTGAAACTGAAATAAAACATACGTGAACAGGCATTGTAAACTG
TAAGTTACGGAAAAAGCTGGCTGTTGTTGTGTCTTTAAAGTTTCACCTGGGTAGTCAAAGATGGAT
CATGGGTCTCAGTGGAGAGCTGAGCCAGGCAGGAGCTGACTAAGGGTGAGAGGTGGGAGTTAGCA
GCCTCTGAACATCTGTGTACCATGGGACCCCCTTCCTCCTGCATGGTACCCCAGACAAGGAGCCT
AGTAAGAGATACTAATGGCTTGTTGTCCAGAGATGTTCAAACTGCAGAGAAAGATAAGACAACAA
GCATTGGCCTCCAATCATGATGACAGATAGGAGGAGGTGGGAGCTCCTTAGCAGTGCTGGTTGGCC
TTCCATGTTCTACTGTGGGCCATCTCTGCCATGTACTGTAGGCTACTAGCTTCTATATTAAAGAATG
CAAGAGGGGCCAGGAGCGGAGGCTCATGCCTGTAATCTCAGCACTTTGGGAGGCCAAGGTGGGCA
GATCACTTGAGGTCAGGAGTTTGTGACCAGCCTGGCCAACATGGTGAAACTCTGCCTTTACTAAAA
ATATAAAAATTAGCTGGGTGTGGTGGTGTGCACCTGTAATCCCAGCTACTCGGGAGACTGAGGCAC
AAGAATTGCTTGAACCTGGGAGGCGGAAGTTGCAGTGAGCCCAGATTGCGCCACTGCACTCCACCC
TGGGCAACAGAGAAAGACTCTGCCTCAAAAAAAAAAAAAAAGCAAGAGGAAGTGAAATAATC
AAGGCCGCCATTTAATAGTGAGCAGCCACTCCATGTGGTACTGTGCAAGCACATTATAAATATTAG
CCTCACAAGAAATGTATTAGCATTTGTATTTTGTACACTGGTTAAGTATCTTGCCCAAGACCTCAAA
ACTGGTTAAGGGCAGCAGAATTTAGCCCCAGCACCACCTTTTCAAAGCCTGGGCTTCTCACACTTCT
CCATGCTGTTCCCATTTTAACACAGGTATCTCGCCATTCCAGCCACTCAAACTTTGGCATTTAAGAA
AATTATCCTAAAGCTAAACTAAACTTCAAGGATGACCATTCTCCTGACCCCTTCCCATCAAAATTTT
ATCTTTAGTCAGTTTGTTTTCGTTTTGTTTTGTTTTCAGAACTACCTCTGGCACATCCTCCAAATGA
AAGG (SEQ ID NO:11)
``` ers to the US Patent Office...

SEQUENCE LISTING

```
<160> NUMBER OF SEQ ID NOS: 38

<210> SEQ ID NO 1
<211> LENGTH: 3653
<212> TYPE: DNA
<213> ORGANISM: Mus musculus

<400> SEQUENCE: 1
gaaatcgtgg tccccaagcc tcatgccagg ctgcacttgc acgtcgcggg ccagtctcct      60
cgcctgcaga tagttcccaa acatgagga tatttgctgg cattatattc acagcctgct     120
gtcacttgct acgggcgttt actatcacgg ctccaaagga cttgtacgtg gtggagtatg     180
gcagcaacgt cacgatggag tgcagattcc ctgtagaacg ggagctggac ctgcttgcgt     240
tagtggtgta ctgggaaaag gaagatgagc aagtgattca gtttgtggca ggagaggagg     300
accttaagcc tcagcacagc aacttcaggg ggagagcctc gctgccaaag gaccagcttt     360
tgaagggaaa tgctgccctt cagatcacag acgtcaagct gcaggacgca ggcgtttact     420
gctgcataat cagctacggt ggtgcggact acaagcgaat cacgctgaaa gtcaatgccc     480
cataccgcaa aatcaaccag agaatttccg tggatccagc cacttctgag catgaactaa     540
tatgtcaggc cgagggttat ccagaagctg aggtaatctg gacaaacagt gaccaccaac     600
ccgtgagtgg gaagagaagt gtcaccactt cccggacaga ggggatgctt ctcaatgtga     660
ccagcagtct gagggtcaac gccacagcga atgatgtttt ctactgtacg ttttggagat     720
cacagccagg gcaaaaccac acagcggagc tgatcatccc agaactgcct gcaacacatc     780
ctccacagaa caggactcac tgggtgcttc tgggatccat cctgttgttc ctcattgtag     840
tgtccacggt cctcctcttc ttgagaaaac aagtgagaat gctagatgtg gagaaatgtg     900
gcgttgaaga tacaagctca aaaaaccgaa atgatacaca attcgaggag acgtaagcag     960
tgttgaaccc tctgatcgtc gattggcagc ttgtggtctg tgaaagaaag ggcccatggg    1020
acatgagtcc aaagactcaa gatggaacct gagggagaga accaagaaag tgttgggaga    1080
ggagcctgga acaacggaca tttttccag ggagacactg ctaagcaagt tgcccatcag    1140
tcgtcttggg aaatggattg agggttcctg gcttagcagc tggtccttgc acagtgacct    1200
tttcctctgc tcagtgccgg gatgagagat ggagtcatga gtgttgaaga ataagtgcct    1260
tctatttatt ttgagtctgt gtgttctcac tttgggcatg taattatgac tggtgaattc    1320
tgacgacatg atagatctta agatgtagtc accaaactca actgctgctt agcatcctcc    1380
```

```
gtaactactg atacaagcag ggaacacaga ggtcacctgc ttggtttgac aggctcttgc    1440
tgtctgactc aaataatctt tattttcag tcctcaaggc tcttcgatag cagttgttct    1500
gtatcagcct ataggtgtc aggtatagca ctcaacatct catctcatta caatagcaac    1560
cctcatcacc atagcaacag ctaacctctg ttatcctcac ttcatagcca ggaagctgag    1620
cgactaagtc acttgcccac agagtatcag ctctcagatt tctgttcttc agccactgtc    1680 cttcaggat agaatttgtc gttaagaaat taatttaaaa actgattatt gagtagcatt     1740
gtatatcaat cacaacatgc cttgtgcact gtgctggcct ctgagcataa agatgtacgc    1800
cggagtaccg gtcggacatg tttatgtgtg ttaaatactc agagaaatgt tcattaacaa    1860
ggagcttgca ttttagagac actggaaagt aactccagtt cattgtctag cattacattt    1920
acctcatttg ctatccttgc catacagtct cttgttctcc atgaagtgtc atgaatcttg    1980
ttgaatagtt cttttatttt ttaaatgttt ctatttaaat gatattgaca tctgaggcga    2040
tagctcagtt ggtaaaaccc tttcctcaca agtgtgaaac cctgagtctt atccctagaa    2100
cccacataaa aaacagttgc gtatgtttgt gcatgctttt gatcccagca ctagggaggc    2160
agaggcaggc agatcctgag ctctcattga ccacccagcc tagcctacat ggttagctcc    2220
aggcctacag gagctggcag agcctgaaaa acgatgccta gacacacaca cacacacaca    2280
cacacacaca cacacacaca caccatgt actcatagac ctaagtgcac cctcctacac     2340
atgcacacac atacaattca aacacaaatc aacagggaat tgtctcagaa tggtccccaa    2400
gacaaagaag aagaaaaaca ccaaaccagc tctattccct cagcctatcc tctctactcc    2460
ttcctagaag caactactat tgttttgta tataaattta cccaacgaca gttaatatgt     2520
agaatatata ttaaagtgtc tgtcaatata tattatctct ttctttcttt cttccttct    2580 ttctttcttt ctttctttct ttctttcttt ctttctttct ttcttccttc cttccttcct   2640
tccttccttc cttccttcct ttctttcttt cttttctttt ttctgtctat ctgtacctaa    2700
atggttgctc actatgcatt ttctgtgctc ttcgcccttt ttatttaatg tatggatatt    2760
tatgctgctt ccagaatgga tctaaagctc tttgtttcta ggttttctcc cccatccttc    2820
taggcatctc tcacactgtc taggccagac accatgtctg ctgcctgaat ctgtagacac    2880
catttataaa gcacgtactc accgagtttg tatttggctt gttctgtgtc tgattaaagg    2940
gagaccatga gtccccaggg tacactgagt taccccagta ccaagggga gccttgtttg     3000 tgtctccatg gcagaagcag gcctggagcc attttggttt cttccttgac ttctctcaaa    3060
cacagacgcc tcacttgctc attacaggtt ctcctttggg aatgtcagca ttgctccttg    3120
actgctggct gccctggaag gagcccatta gctctgtgtg agcccttgac agctactgcc    3180
tctccttacc acaggggcct ctaagatact gttacctaga ggtcttgagg atctgtgttc    3240 tctggggga ggaaaggagg aggaacccag aactttctta cagttttcct tgttctgtca     3300
catgtcaaga ctgaaggaac aggctgggct acgtagtgag atcctgtctc aaaggaaaga    3360
cgagcatagc cgaaccccg gtggaacccc ctctgttacc tgttcacaca agcttattga     3420
tgagtctcat gttaatgtct tgtttgtatg aagtttaaga aaatatcggg ttgggcaaca    3480
cattctattt attcatttta tttgaaatct taatgccatc tcatggtgtt ggattggtgt    3540
ggcactttat tcttttgtgt tgtgtataac cataaatttt attttgcatc agattgtcaa    3600
tgtattgcat taatttaata aatattttta tttattaaaa aaaaaaaaaa aaa            3653
```

<210> SEQ ID NO 2

<211> LENGTH: 290
<212> TYPE: PRT
<213> ORGANISM: Mus musculus

<400> SEQUENCE: 2

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
290

<210> SEQ ID NO 3
<211> LENGTH: 3691
<212> TYPE: DNA
<213> ORGANISM: Homo sapiens

<400> SEQUENCE: 3
ggcgcaacgc tgagcagctg gcgcgtcccg cgcggcccca gttctgcgca gcttcccgag      60
gctccgcacc agccgcgctt ctgtccgcct gcagggcatt ccagaaagat gaggatattt     120
gctgtcttta tattcatgac ctactggcat tgctgaacg catttactgt cacggttccc     180
aaggacctat atgtggtaga gtatggtagc aatatgacaa ttgaatgcaa attcccagta     240

-continued

```
gaaaaacaat tagacctggc tgcactaatt gtctattggg aaatggagga taagaacatt      300
attcaatttg tgcatggaga ggaagacctg aaggttcagc atagtagcta cagacagagg      360
gcccggctgt tgaaggacca gctctccctg ggaaatgctg cacttcagat cacagatgtg      420
aaattgcagg atgcaggggt gtaccgctgc atgatcagct atggtggtgc cgactacaag      480
cgaattactg tgaaagtcaa tgccccatac aacaaaatca accaaagaat tttggttgtg      540
gatccagtca cctctgaaca tgaactgaca tgtcaggctg agggctaccc caaggccgaa      600
gtcatctgga caagcagtga ccatcaagtc ctgagtggta agaccaccac caccaattcc      660
aagagagagg agaagctttt caatgtgacc agcacactga gaatcaacac aacaactaat      720
gagattttct actgcacttt taggagatta gatcctgagg aaaaccatac agctgaattg      780
gtcatcccag aactacctct ggcacatcct ccaaatgaaa ggactcactt ggtaattctg      840
ggagccatct tattatgcct tggtgtagca ctgacattca tcttccgttt aagaaaaggg      900
agaatgatgg atgtgaaaaa atgtggcatc aagatacaa actcaaagaa gcaaagtgat      960
acacatttgg aggagacgta atccagcatt ggaacttctg atcttcaagc agggattctc     1020
aacctgtggt ttaggggttc atcggggctg agcgtgacaa gaggaaggaa tgggcccgtg     1080
ggatgcaggc aatgtgggac ttaaaaggcc caagcactga aaatggaacc tggcgaaagc     1140
agaggaggag aatgaagaaa gatggagtca acagggagc ctggagggag accttgatac     1200
tttcaaatgc ctgaggggct catcgacgcc tgtgacaggg agaaggata cttctgaaca     1260 aggagcctcc aagcaaatca tccattgctc atcctaggaa gacgggttga gaatccctaa     1320
tttgagggtc agttcctgca gaagtgccct ttgcctccac tcaatgcctc aatttgtttt     1380
ctgcatgact gagagtctca gtgttggaac gggacagtat ttatgtatga gtttttccta     1440 tttatttga gtctgtgagg tcttcttgtc atgtgagtgt ggttgtgaat gatttctttt     1500
gaagatatat tgtagtagat gttacaattt tgtcgccaaa ctaaacttgc tgcttaatga     1560
tttgctcaca tctagtaaaa catggagtat ttgtaaggtg cttggtctcc tctataacta     1620
caagtataca ttggaagcat aaagatcaaa ccgttggttg cataggatgt caccttattt     1680
taacccatta atactctggt tgacctaatc ttattctcag acctcaagtg tctgtgcagt     1740
atctgttcca tttaaatatc agctttacaa ttatgtggta gcctacacac ataatctcat     1800
ttcatcgctg taaccaccct gttgtgataa ccactattat tttacccatc gtacagctga     1860
ggaagcaaac agattaagta acttgcccaa accagtaaat agcagacctc agactgccac     1920
ccactgtcct tttataatac aatttacagc tatattttac tttaagcaat tcttttattc     1980
aaaaaccatt tattaagtgc ccttgcaata tcaatcgctg tgccaggcat tgaatctaca     2040
gatgtgagca agacaaagta cctgtcctca aggagctcat agtataatga ggagattaac     2100
aagaaaatgt attattacaa tttagtccag tgtcatagca taaggatgat gcgagggaa     2160 aacccgagca gtgttgccaa gaggaggaaa taggccaatg tggtctggga cggttggata     2220
tacttaaaca tcttaataat cagagtaatt ttcatttaca aagagaggtc ggtacttaaa     2280
ataaccctga aaaataacac tggaattcct tttctagcat tatatttatt cctgatttgc     2340
ctttgccata taatctaatg cttgtttata tagtgtctgg tattgtttaa cagttctgtc     2400
ttttctattt aaatgccact aaattttaaa ttcataccttt tccatgattc aaaattcaaa     2460
agatcccatg ggagatggtt ggaaaatctc cacttcatcc tccaagccat tcaagtttcc     2520
tttccagaag caactgctac tgcctttcat tcatatgttc ttctaaagat agtctacatt     2580
tggaaatgta tgttaaaagc acgtattttt aaaattttt tcctaaatag taacacattg     2640
```

```
tatgtctgct gtgtactttg ctattttat ttattttagt gttttcttata tagcagatgg    2700 aatgaatttg aagttcccag ggctgaggat ccatgccttc tttgtttcta agttatcttt    2760
cccatagctt ttcattatct ttcatatgat ccagtatatg ttaaatatgt cctacatata    2820
catttagaca accaccattt gttaagtatt tgctctagga cagagtttgg atttgtttat    2880
gtttgctcaa aaggagaccc atgggctctc cagggtgcac tgagtcaatc tagtcctaaa    2940
aagcaatctt attattaact ctgtatgaca gaatcatgtc tggaactttt gttttctgct    3000
ttctgtcaag tataaacttc actttgatgc tgtacttgca aaatcacatt ttctttctgg    3060
aaattccggc agtgtacctt gactgctagc taccctgtgc cagaaaagcc tcattcgttg    3120
tgcttgaacc cttgaatgcc accagctgtc atcactacac agccctccta agaggcttcc    3180
tggaggtttc gagattcaga tgccctggga gatcccagag tttcctttcc ctcttggcca    3240
tattctggtg tcaatgacaa ggagtacctt ggctttgcca catgtcaagg ctgaagaaac    3300
agtgtctcca acagagctcc ttgtgttatc tgtttgtaca tgtgcatttg tacagtaatt    3360
ggtgtgacag tgttctttgt gtgaattaca ggcaagaatt gtggctgagc aaggcacata    3420
gtctactcag tctattccta agtcctaact cctccttgtg gtgttggatt tgtaaggcac    3480
tttatccctt ttgtctcatg tttcatcgta aatggcatag gcagagatga tacctaattc    3540
tgcatttgat tgtcactttt tgtacctgca ttaatttaat aaaatattct tatttatttt    3600
gttacttggt acaccagcat gtccattttc ttgtttattt tgtgtttaat aaaatgttca    3660
gtttaacatc ccagtggaga aagttaaaaa a                                   3691
```

<210> SEQ ID NO 4
<211> LENGTH: 290
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 5
<211> LENGTH: 3656
<212> TYPE: DNA
<213> ORGANISM: Artificial Sequence
<220> FEATURE:
<223> OTHER INFORMATION: Polynucleotide (humanized CD274 mRNA)

<400> SEQUENCE: 5
gaaatcgtgg tccccaagcc tcatgccagg ctgcacttgc acgtcgcggg ccagtctcct    60
cgcctgcaga tagttcccaa acatgaggga tatttgctgg cattatattc acagcctgct   120
gtcacttgct acgggcattt actgtcacgg ttcccaagga cctatatgtg gtagagtatg   180
gtagcaatat gacaattgaa tgcaaattcc cagtagaaaa acaattagac ctggctgcac   240
taattgtcta ttgggaaatg gaggataaga acattattca atttgtgcat ggagaggaag   300
acctgaaggt tcagcatagt agctacagac agagggcccg gctgttgaag gaccagctct   360
ccctgggaaa tgctgcactt cagatcacag atgtgaaatt gcaggatgca ggggtgtacc   420
gctgcatgat cagctatggt ggtgccgact acaagcgaat tactgtgaaa gtcaatgccc   480
catacaacaa aatcaaccaa agaattttgg ttgtggatcc agtcacctct gaacatgaac   540
tgacatgtca ggctgagggc taccccaagg ccgaagtcat ctggacaagc agtgaccatc   600
aagtcctgag tggtaagacc accaccacca ttccaagag agaggagaag cttttcaatg   660
tgaccagcac actgagaatc aacacaacaa ctaatgagat tttctactgc acttttagga   720
gattagatcc tgaggaaaac catacagctg aattggtcat cccagaacta cctctggcac   780
atcctccaaa tgaaaggact cactgggtgc ttctgggatc catcctgttg ttcctcattg   840
tagtgtccac ggtcctcctc ttcttgagaa acaagtgag aatgctagat gtggagaaat   900
gtggcgttga agatacaagc tcaaaaaacc gaaatgatac acaattcgag agacgtaag   960 cagtgttgaa ccctctgatc gtcgattggc agcttgtggt ctgtgaaaga aagggcccat  1020
gggacatgag tccaaagact caagatgaaa cctgagggag agaaccaaga agtgttggg  1080 agaggagcct ggaacaacgg acatttttc cagggagaca ctgctaagca agttgcccat  1140
cagtcgtctt gggaaatgga ttgagggttc ctggcttagc agctggtcct tgcacagtga  1200
ccttttcctc tgctcagtgc cgggatgaga gatggagtca tgagtgttga agaataagtg  1260
ccttctattt attttgagtc tgtgtgttct cactttgggc atgtaattat gactggtgaa  1320

```
ttctgacgac atgatagatc ttaagatgta gtcaccaaac tcaactgctg cttagcatcc      1380
tccgtaacta ctgatacaag cagggaacac agaggtcacc tgcttggttt gacaggctct      1440
tgctgtctga ctcaaataat ctttattttt cagtcctcaa ggctcttcga tagcagttgt      1500
tctgtatcag ccttataggt gtcaggtata gcactcaaca tctcatctca ttacaatagc      1560
aaccctcatc accatagcaa cagctaacct ctgttatcct cacttcatag ccaggaagct      1620
gagcgactaa gtcacttgcc cacagagtat cagctctcag atttctgttc ttcagccact      1680
gtcctttcag gatagaattt gtcgttaaga aattaattta aaaactgatt attgagtagc      1740
attgtatatc aatcacaaca tgccttgtgc actgtgctgg cctctgagca taaagatgta      1800
cgccggagta ccggtcggac atgtttatgt gtgttaaata ctcagagaaa tgttcattaa      1860
caaggagctt gcattttaga gacactggaa agtaactcca gttcattgtc tagcattaca      1920
tttacctcat ttgctatcct tgccatacag tctcttgttc tccatgaagt gtcatgaatc      1980
ttgttgaata gttcttttat ttttaaatg tttctattta aatgatattg acatctgagg       2040
cgatagctca gttggtaaaa ccctttcctc acaagtgtga aaccctgagt cttatcccta      2100
gaacccacat aaaaaacagt tgcgtatgtt tgtgcatgct tttgatccca gcactaggga      2160
ggcagaggca ggcagatcct gagctctcat tgaccaccca gcctagccta catggttagc      2220
tccaggccta caggagctgg cagagcctga aaaacgatgc ctagacacac acacacacac      2280
acacacacac acacacacac acacacacca tgtactcata gacctaagtg caccctccta      2340
cacatgcaca cacatacaat tcaaacacaa atcaacaggg aattgtctca gaatggtccc      2400
caagacaaag aagaagaaaa acaccaaacc agctctattc cctcagccta tcctctctac      2460
tccttcctag aagcaactac tattgttttt gtatataaat ttacccaacg acagttaata      2520
tgtagaatat atattaaagt gtctgtcaat atatattatc tctttctttc tttcttcctt      2580
tctttctttc tttctttctt tctttctttc tttctttctt tctttcttcc ttccttcctt      2640
ccttccttcc ttccttcctt cctttctttc tttctttctt tttttctgtc tatctgtacc      2700
taaatggttg ctcactatgc attttctgtg ctcttcgccc ttttatttta atgtatggat      2760
atttatgctg cttccagaat ggatctaaag ctctttgttt ctaggttttc tcccccatcc      2820
ttctaggcat ctctcacact gtctaggcca gacaccatgt ctgctgcctg aatctgtaga      2880
caccatttat aaagcacgta ctcaccgagt ttgtatttgg cttgttctgt gtctgattaa      2940
agggagacca tgagtcccca gggtacactg agttacccca gtaccaaggg ggagccttgt      3000
ttgtgtctcc atggcagaag caggcctgga gccattttgg tttcttcctt gacttctctc      3060
aaacacagac gcctcacttg ctcattacag gttctccttt gggaatgtca gcattgctcc      3120
ttgactgctg gctgccctgg aaggagccca ttagctctgt gtgagccctt gacagctact      3180
gcctctcctt accacagggg cctctaagat actgttacct agaggtcttg aggatctgtg      3240
ttctctgggg ggaggaaagg aggaggaacc cagaactttc ttacagtttt ccttgttctg      3300
tcacatgtca agactgaagg aacaggctgg gctacgtagt gagatcctgt ctcaaaggaa      3360
agacgagcat agccgaaccc ccggtggaac cccctctgtt acctgttcac acaagcttat      3420
tgatgagtct catgttaatg tcttgtttgt atgaagttta agaaaatatc gggttgggca      3480
acacattcta tttattcatt ttatttgaaa tcttaatgcc atctcatggt gttggattgg      3540
tgtggcactt tattcttttg tgttgtgtat aaccataaat tttatttttgc atcagattgt      3600 caatgtattg cattaatttta ataaatattt ttatttatta aaaaaaaaa aaaaaa        3656
```

```
<210> SEQ ID NO 6
<211> LENGTH: 291
<212> TYPE: PRT
<213> ORGANISM: Artificial Sequence
<220> FEATURE:
<223> OTHER INFORMATION: Polypeptide (humanized CD274 amino acid)

<400> SEQUENCE: 6

Met Arg Ile Phe Ala Gly Ile Ile Phe Thr Ala Cys Cys His Leu Leu
1               5                   10                  15

Arg Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Trp Val Leu Leu Gly Ser Ile Leu Leu Phe Leu Ile Val Val Ser Thr
                245                 250                 255

Val Leu Leu Phe Leu Arg Lys Gln Val Arg Met Leu Asp Val Glu Lys
            260                 265                 270

Cys Gly Val Glu Asp Thr Ser Ser Lys Asn Arg Asn Asp Thr Gln Phe
        275                 280                 285

Glu Glu Thr
    290

<210> SEQ ID NO 7
<211> LENGTH: 13440
<212> TYPE: DNA
<213> ORGANISM: Artificial Sequence
<220> FEATURE:
<223> OTHER INFORMATION: Polynucleotide (humanization fragment A)

<400> SEQUENCE: 7
gtcacggttc ccaaggacct atatgtggta gagtatggta gcaatatgac aattgaatgc      60
aaattcccag tagaaaaaca attagacctg ctgcactaa ttgtctattg ggaaatggag      120
```

```
gataagaaca ttattcaatt tgtgcatgga gaggaagacc tgaaggttca gcatagtagc        180
tacagacaga gggcccggct gttgaaggac cagctctccc tgggaaatgc tgcacttcag        240
atcacagatg tgaaattgca ggatgcaggg gtgtaccgct gcatgatcag ctatggtggt        300
gccgactaca agcgaattac tgtgaaagtc aatggtaaga attattatag atgagaggcc        360
tgatctttat tgaaaacata ttccaagtgt tgaagacttt tcattcttgt aagtccatac        420
ttattttcaa acagaacagc atagtctgtt cattcattca ttcaattcat gaattcattc        480
acataattat ccaatttctt gagcacctat ttgatagtca ctggaaatcc agagacaaac        540
aacacagagc catgttctac agtatgtaca gttttccaaa aagaatttct agtctttact        600
tttttattac aaatggaata cgtatacttg caaataattc agatactgtg aagagatca        660 aatgaattgc aaaagtgtcc ctcctcccct caccactatc tcccatggca tgcagagaga        720
gtaaccatta tttgtgtgtc cctccagaaa ttttttatt caactactat tttttatt        780 tattaggtcc gtcagttttc cttttttgag cctctctata tcaaatgcaa ataaatatat        840
tcagaacaaa ccccactgta aggttcacat taaaaagac ttgaagtcac cctatgaaga        900
caaaaaataa tcacattaag tgtgaaagaa cctattcttc cagtacagga taagccatac        960
ttactgggca tatattcatc ttgaaaatct atactgatgt tgtcttgggg aattgaaaag       1020
gaactaggag tgttagttcc tcggtattga cccacagtta tgttatcagg tcacttgagt       1080
tcaaagtttt gtgttggcac tagctaagta aaggaaaaca cctctgcttt cattgttgag       1140
tttcacagaa ttgagagctg aaaggatccc aggcaggagc agctaatcca aactcccaca       1200
aagaacaaaa atcccccaga ggatcttctg ttcttatatt tcctgcaatg gcgtccctgt       1260
catatcccac aatggcctcc ctgccatttg gatatccctt ccatatcctg ttgaaattac       1320
tccctaatag taagctgaaa tctgcccctc tagttgtagt cttgggatta tttcattac       1380 atgatgacct tttaatattt gactagaatt aaatcatctc ccttggtct ttccattcct       1440 gggctaacta ccatcaatct gagggctaac aatacaagta gaaaaagtat acatttgtca       1500
ctgatcactg atcaattatt aatcaatgat cactgataac tataaactca aaaacaaaat       1560
catgtgggga ttaagagaaa tgtatcagtt ttatgttgta tttctggtcc ctgatactgg       1620
ctcaggtaat gccactattg tcaagaagat accacttgta aagtagattt aattttcatt       1680
atattttacc atatgcttct ccattcatga catctcttga gatgttgtgg tttatacttt       1740 cagttttct ccagtccatc cgcaaatatc aggcatctac tgtgttccaa gatattaaag       1800
aaatcatcat gacttagcct catcaacagc attgctagat ctgggatgga aaggaagagt       1860
ataatcctgg cagtcaggaa gaaggcagca taaagtataa gtttctgctt ccaaaaaagg       1920
tctctcatca gcctgtaggg agtgtgtagg gaagggacac ctgtccttgt agtagggaag       1980
ggttttattc aggtcgtctg ggctccataa tatcccttgt gtatctgcag tctcctttgc       2040
catggatcaa cacaatagga aatcttccgg cactgatggt ttttccaagg gggagttctt       2100
cctggagcaa agcaaatgac caaccaggtt tgaggacctg atttgtttga caattccatt       2160
ttgtattgta aattacttaa ttggcattct actcccaatc catcttgtca tttgcataca       2220
gtggttttgg gattgagttc agctatacca aaagtctgaa ccttctgcac ttagaacaag       2280
gcaaccacca agcttcactt gcactgaggc cgtgtctcca atggaaatga ggcagctggc       2340
ttgcaggagc ttcccaactc agggaagtag aactcctgag tcacctccat atgcaaatga       2400
tttcacagta atgctgttga acttcacttc ccatcacagc aaatgtgtgg taacatagct       2460
```

| | |
|---|---|
| tccccacagg agtttactca ccatggtatt ttaaaggtga acatttcaa aactgaaatt | 2520 |
| tgaaagaatt tagttttgga ttcactcaat tatcactatc acttcgggtg ttattgcacc | 2580 |
| tttcttgttt gtgagtttaa atgccagact ctcaggccac taactttcaa ttaaaagtgt | 2640 |
| ttttctttaa tcgctgaacc taacagcagg gaaaacgaaa tgttcattca gactttcaga | 2700 |
| accttcaatg agattaggca gctgaaagat caaagtgttg catagttgtc ccgataaagc | 2760 |
| tatttggatc atatggacca aatcgactgc tgtcattccc caccaacccc atctctcccc | 2820 |
| aaaattccca gccctgttta agtgttctct gtagcattta tctctatcta gtatattgtg | 2880 |
| tagcatatca tatcatactt ttctgttttg tttattgtct ctctcctcct agaatataaa | 2940 |
| ctccacaagc acaaagattt gggcctgttt tataatattg ttgcatcccc agggcctgat | 3000 |
| atacagcaga gtggtggtac gaaaagagca cacaaaaaaa tatttgttga gtcaatgaat | 3060 |
| gaatgatttc ctcaaatagg attagcctaa aattttggaa acatgaacag atttggatat | 3120 |
| gtgaaaattt atttccagac tgttcatcag gaactgttag cagcttctaa agggtacact | 3180 |
| ggagcagcag tagtaaaagg aggaagagga gcagctctgc tactgctact atcgagtact | 3240 |
| actacaatta gcacttgctt attctgtgtg ttaggccctg tactgaacac tctgtctaaa | 3300 |
| ttagttcatt tcctcctgga aatgactcta gggggtaagt gcttcatcat gtaagatgag | 3360 |
| tattttcac attttgttgt gtctgaaatc tgagtgtgtc tttcaatgat ggaatctttg | 3420 |
| attccatgat aagtggtatt attcccattt taaggatgag gaaactgagg tccaaagaaa | 3480 |
| ttaagtaatt tgcccaaatt cacccagcct agaaatgat aaagctagtt ctaaacccaa | 3540 |
| gcagattagc tctgaagtct gggcccttaa taaccacttt ttattgccta tatttgtacc | 3600 |
| tctggtgtac gtatcaagtt atatgttgac ttcaaaacta tcatgacctt ttcttggttt | 3660 |
| tgattgtcca acattagtat agtgttctgg gtctgcaaaa attttgatta ctcatctcat | 3720 |
| ctgtaaaaca ttttgaactc gtgtgtttgt gcatgcacat ttgtgtgtaa ttataaaaat | 3780 |
| tttactttct gttaatatat aagttgtatc ataagaaact gccgttttg aagagcaaaa | 3840 |
| aaaggttgaa tgttaccagt tacatctggt tcaacctaat agacatttgt acaaaaacag | 3900 |
| acattttaag aggttgaaat aaaaatttaa taaacaatat tttcagtttt tactaattgt | 3960 |
| gatgcttcac tatcattagc taatatgtca aggcataata taccttaggg tgaactttat | 4020 |
| cattaacaaa ggtggatggt gtcaataatc ttgaggtttg tgttttttta tataacactg | 4080 |
| cgaggtctaa ttaagtactt actgtttacc acctcataca gtggccgata aaaagtgtca | 4140 |
| cttctgctgt ttcctctggg ttgtgcttga attattagta ttatcttcag tcctcagttt | 4200 |
| ctttgtggga aactttttaa ttagttgttt aattttgtaa gatggttagt ttagtcaaaa | 4260 |
| ttagataaga gaatttgaaa atccgtagct accccaaagc aacctacaca taagaactat | 4320 |
| tattttgtg ttttgaaatc ataatttat tgatttccag tgtttccact ggtagtggtt | 4380 |
| tcattgatat aggagtatca aaacatcact cattatttat ttcagtttca tttgatccta | 4440 |
| gccgttttgt attaactctc tgtgaagaaa ttacctcaca aatctattgc tgtcgctagc | 4500 |
| tcgctacctt aggaccgtta tagttactag cataacttcg tatagcatac attatacgaa | 4560 |
| gttattccag acatgataag atacattgat gagtttggac aaaccacaac tagaatgcag | 4620 |
| tgaaaaaaat gctttatttg tgaaatttgt gatgctattg ctttatttgt aaccattata | 4680 |
| agctgcaata aacaagttaa caacaacaat tgcattcatt ttatgtttca ggttcagggg | 4740 |
| gaggtgtggg aggttttta aagcaagtaa aacctctaca gatgtgatat ggctgattat | 4800 |
| gatcattact tatctagagc ttagatcccc cctgcccggt tattattatt tttgacacca | 4860 |

```
gaccaactgg taatggtgcg gaggcacgct cagctggaat tggccgcaac tagggcaggt    4920
ttaacaacaa caattgcatt cattttatgt ttcaggttca gggggaggtg tgggaggttt    4980
tttaaagcaa gtaaaacctc tacagatgtg atatggctga ttatgatcat tacttatcta    5040
gatcaatcgc catcttccag caggcgcacc attgcccctg tttcactatc caggttacgg    5100
atatagttca tgacaatatt tacattggtc cagccaccag cttgcatgat ctccggtatt    5160
gaaactccag cgcgggccat atctcgcgcg gctccgacac gggcactgtg tccagaccag    5220
gccaggtatc tctgaccaga gtcatcctaa atacacaaa caattagaat cagtagttta    5280
acacattata cacttaaaaa tttttatattt accttagcgc cgtaaatcaa tcgatgagtt    5340
gcttcaaaaa tcccttccag ggcgcgagtt gatagctggc tggtggcaga tggcgcggca    5400
acaccatttt ttctgacccg gcaaaacagg tagttattcg gatcatcagc tacaccagag    5460
acggaaatcc atcgctcgac cagtttagtt accccccaggc taagtgcctt ctctacacct    5520
gcggtgctaa ccagcgtttt cgttctgcca atatggatta acattctccc accgtcagta    5580
cgtgagatat cttttaaccct gatcctggca atttcggcta tacgtaacag ggtgttataa    5640
gcaatcccca gaaatgccag attacgtata tcctggcagc gatcactatt ttccatgagt    5700
gaacgaacct ggtcgaaatc agtgcgttcg aacgctagag cctgttttgc acgttcaccg    5760
gcatcaacgt tttcttttcg gatccgccgc ataaccagtg aaacagcatt gctgtcactt    5820
ggtcgtggca gcccggaccg acgatgaagc atgtttagct ggcccaaatg ttgctggata    5880
gtttttactg ccagaccgcg cgcctgaaga tatagaagat aatcgcgaac atcttcaggt    5940
tctgcgggaa accatttccg gttattcaac ttgcaccatg ccgcccacga ccggcaaacg    6000
gacagaagca ttttccaggt atgctcagaa aacgcctggc gatccctgaa catgtccatc    6060
aggttcttgc gaacctcatc actcgttgca tcgaccggta atgcaggcaa attttggtgt    6120
acggtcagta aattggaatt taaatcggta cgcaccttcc tcttcttctt gggggtaccc    6180
atggtgctgg cttggccggg agctggctca gagcagggga caccacctgg gtcgagccag    6240
ccaacctgtg agcaggtgga attttgtggg ctgtggcctg ggagccagca ccctcttcct    6300
cttatagata ctagtggccc ctaggaatta tgaagtcaaa gaggaccagg acctcacaga    6360
ccatggccag tgaggacctg taccatgtcc aaatatgggc atgagagggg tgggcagggc    6420
tttggcatca ggagttgctt gtgtcacagt caagaagtga caaagatggc atccacttga    6480
gtgttcagtt agtcactcag cttaggtgtt aagtgccaca cacctgcttc taggctaggt    6540
cctgatagat aacccaaggc caggcaggtg ggtgaaacag ccacatggat ttgaactgtg    6600
aaaagcacac atcttcagac tgctcagaga atgctgctga gggaacttga cctttttaaga    6660 aattatccaa cgcccagtg aggcactgac agacaaatcc agagggtctc agagttgcag    6720
gggggtgggc tctagtaaaa cattgaggcc ccatcaagtg cttcaggtat aaatgggagc    6780
cacatggatg cagagcagtg tttggactga gggaggtgtt ggacattact agacagaagg    6840
tggacgtggg tgctgctact ggcgcccggg ctaggggctg caggtcgagg tctgatggaa    6900
ttagaacttg gcaaaacaat actgagaatg aagtgtatgt ggaacagagg ctgctgatct    6960
cgttcttcag gctatgaaac tgacacattt ggaaaccaca gtacttagaa ccacaaagtg    7020
ggaatcaaga gaaaaacaat gatcccacga gagatctata gatctataga tcatgagtgg    7080
gaggaatgag ctggccctta atttggtttt gcttgtttaa attatgatat ccaactatga    7140
aacattatca taaagcaata gtaaagagcc ttcagtaaag agcaggcatt tatctaatcc    7200
```

-continued

```
caccccaccc ccaccccgt agctccaatc cttccattca aaatgtaggt actctgttct    7260
caccctttctt aacaaagtat gacaggaaaa acttccattt tagtggacat ctttattgtt   7320
taatagatca tcaatttctg cagacttaca gcggatcccc tcagaagaac tcgtcaagaa   7380
ggcgatagaa ggcgatgcgc tgcgaatcgg gagcggcgat accgtaaagc acgaggaagc   7440
ggtcagccca ttcgccgcca agctcttcag caatatcacg ggtagccaac gctatgtcct   7500
gatagcggtc cgccacaccc agccggccac agtcgatgaa tccagaaaag cggccatttt   7560
ccaccatgat attcggcaag caggcatcgc catgggtcac gacgagatca tcgccgtcgg   7620
gcatgcgcgc cttgagcctg gcgaacagtt cggctggcgc gagcccctga tgctcttcgt   7680
ccagatcatc ctgatcgaca agaccggctt ccatccgagt acgtgctcgc tcgatgcgat   7740
gtttcgcttg gtggtcgaat gggcaggtag ccggatcaag cgtatgcagc cgccgcattg   7800
catcagccat gatggatact ttctcggcag gagcaaggtg agatgacagg agatcctgcc   7860
ccggcacttc gcccaatagc agccagtccc ttcccgcttc agtgacaacg tcgagcacag   7920
ctgcgcaagg aacgcccgtc gtggccagcc acgatagccg cgctgcctcg tcctgcagtt   7980
cattcagggc accggacagg tcggtcttga caaaaagaac cgggcgcccc tgcgctgaca   8040
gccgaacac ggcggcatca gagcagccga ttgtctgttg tgcccagtca tagccgaata   8100
gcctctccac ccaagcggcc ggagaacctg cgtgcaatcc atcttgttca atggccgatc   8160
ccatggttta gttcctcacc ttgtcgtatt atactatgcc gatatactat gccgatgatt   8220
aattgtcaac acgtctaaca aaaagccaa aacggccag aatttagcgg acaatttact    8280
agtctaacac tgaaaattac atattgaccc aaatgattac atttcaaaag gtgcctaaaa   8340
aacttcacaa aacacactcg ccaaccccga gcgcatagtt caaaaccgga gcttcagcta   8400
cttaagaaga taggtacata aaaccgacca aagaaactga cgcctcactt atccctcccc   8460
tcaccagagg tccggcgcct gtcgattcag gagagcctac cctaggcccg aaccctgcgt   8520
cctgcgacga gaaaaagcct accgcacacc taccggcagg tggcccccacc ctgcattata   8580
agccaacaga acgggtgacg tcacgacacg acgagggcgc gcgctcccaa aggtacgggt   8640
gcactgccca acggcaccgc cataactgcc gccccgcaa cagacgacaa accgagttct    8700
ccagtcagtg acaaacttca cgtcagggtc cccagatggt gccccagccc atctcacccg   8760
aataagagct ttcccgcatt agcgaaggcc tcaagacctt gggttcttgc cgcccaccat   8820
gccccccacc ttgtttcaac gacctcacag cccgcctcac aagcgtcttc cattcaagac   8880
tcgggaacag ccgccatttt gctgcgctcc ccccaacccc cagttcaggg caaccttgct   8940
cgcggaccca gactacagcc cttggcggtc tctccacacg cttccgtccc accgagcggc   9000
ccggcggcca cgaaagcccc ggccagccca gcagcccgct actcaccaag tgacgatcac   9060
agcgatccac aaacaagaac cgcgacccaa atcccggctg cgacggaact agctgtgcca    9120
cacccggcgc gtccttatat aatcatcggc gttcaccgcc ccacggagat ccctccgcag   9180
aatcgccgag aagggactac ttttcctcgc ctgttccgct ctctggaaag aaaaccagtg   9240
ccctagagtc acccaagtcc cgtcctaaaa tgtccttctg ctgatactgg ggttctaagg   9300
ccgagtctta tgagcagcgg gccgctgtcc tgagcgtccg gcggaagga tcaggacgct   9360
cgctgcgccc ttcgtctgac gtggcagcgc tcgccgtgag gaggggggcg cccgcgggag   9420
gcgccaaaac ccggcgcgga ggccatgcat ataacttcgt atagcataca ttatacgaag    9480
ttatctcgag cttggtaaag gaatggagaa ttaaggctct agatcattag tggttacact   9540
atagtattag aagtaaaaaa aagattatac caacaaaata agaacatgtt aatgtacttg   9600
```

```
taatgaataa acatgaataa agctcttatg ctatataggt gcactaaaca atctactaga    9660
attgtcagca aactacgtat cttaatcctg aaagggtccc aaaccaatga tctaaaattg    9720
aatcaaactt tcttccttga gcataattac ttaaatgatt tattaaaata gccagcattt    9780
aaaagcttaa aatgtaaata tcataatgtg gtatcctaga tagcatccca gaacagaaaa    9840
aggatattag ggaaaaactg gaggaatgga ataaattatg cagtttagtt attaataatg    9900
tactaacgtc cttagttatg acgattgtac catggtaatg taagatacta acaatagagg    9960
aaaccgggta aggagtatac agtaactcta tactatcttt gcaactttt tgtaaattta     10020 aaacttctaa aataaagaac aaatttaaac attaaaaagt atcaccagga acatatatca    10080
ctgtttacag atgaaatact atgtattttc atatctaatt tctgatcatt gacttcaaat    10140
cagaaaagtg aatgacacct caaaatcagg ttttctgttt actgaagtct aagaaaagaa    10200
agcataccag ctggagagat tcatgtttat aaagacagat ttataacaac aaaaataaaa    10260
tatccaagaa taaatttaag aagaagcact ttactgagaa acatatgaaa acctgaacaa    10320
atggagaggg atattttgta tttgaataga aagacttctg gtttaaagat aattctcttt    10380
aaattatttt ttgtagaaat ttaaggggta caagagcagt gttgtcacat ggatatatta    10440
catagtggtg aagtctgggg ttttagtgta aattaatctt tacattttgt ttgagcccaa    10500
taaatgtacc aacatgattt ttatagaaag atagtcattc ctattaatcc aaacttgtcc    10560
caactttgaa ttgaattgag gcagagctag caggtgttcc ccacggctga ggcatctgaa    10620
cattaagcat atccctctga gaaccagcct gcattgatac tctttctaat gtggacagca    10680
tcaagctatg tacgtagttc tgtgctcagc aaaagccctg acttcttttt gtttatgtcc    10740
tagccccata caacaaaatc aaccaaagaa ttttggttgt ggatccagtc acctctgaac    10800
atgaactgac atgtcaggct gagggctacc ccaaggccga agtcatctgg acaagcagtg    10860
accatcaagt cctgagtggt aagaccacca ccaccaattc caagagagag gagaagcttt    10920
tcaatgtgac cagcacactg agaatcaaca caacaactaa tgagattttc tactgcactt    10980
ttaggagatt agatcctgag gaaaaccata cagctgaatt ggtcatccca ggtaatattc    11040
tgaatgtgtc cattaaaata tgtctaacac tgtcccctag cacctagcat gatgtctgcc    11100
tatcatagtc attcagtgat tgttgaataa atgaatgaat gaataacact atgtttacaa    11160
aatatatcct aattcctcac ctccattcat ccaaaccata ttgttactta ataaacattc    11220
agcagatatt tatggaatat acctttgtt ccatgcattg tagtactcat tggatacaca    11280
tagaataata agactcagtt cacactcttc aggaaaacaga taaaaaacta agaaacaaac    11340
aaaaaacagg caatccaaca ccatgtggga aatgctttca tagccgggaa acctggggaa    11400
tacctgagag gaatactcaa ttcaggcctt gtttcaggaa tccaaatcct ggcacatcag    11460
agctgcttcc ctcttttccag ggtggcagga aataaatgga acatatttt ctatcttatg     11520 ccaaacatga gggacccttt ctccccggtg cctctcccaa ggtagtctac aatatttcaa    11580
ctctagcagt ctgcttagtg catagaacat gaggctgtgt gtccctgggc aaattactag    11640
acttctgtgt gcttcacttt ccctgtagga ttataatcta ctgagcaagc ttattgtaag    11700
ggtcagatta gcaacagtgt atgaaaatga tttgagacca ttgcctgcac aaattcaact    11760
attttttttt atctcactac tctacagaag taggtagggt gggagacaga gtctgatgag    11820
aggctcagaa tgtgaaagaa agtgaggcga gtgagcatga tatttaatat aaacacaaag    11880
atattctgag aagagctgct cactgccccc tcccccaata catgttgata ggaaaatgcc    11940
```

| | |
|---|---:|
| acgtacttca gcaaaaacaa ctgaaaaatt agatagaaaa gtcaatcaat aggaaaagat | 12000 |
| aatccaggac ggtgttgtga acagaaagag ggggaaaaaa ctttagaaaa tgatggggat | 12060 |
| gctcttactg gggtacgagt cctcaggtat tgaactggct ttcagtaaaa gctagattag | 12120 |
| tgggttcctg ccatttacaa gctgttttat gacaacttac ttgttgggtg gcctacagta | 12180 |
| actcacctaa ctgcactgag tctgtttcct catctgtaaa ttggggattt ttttttaaat | 12240 |
| acctggcatg cctaactcat aaagttgttc tgaaactgaa ataaaacata cgtgaacagg | 12300 |
| cattgtaaac tgtaagttac ggaaaaagct ggctgttgtt gtgtctttaa agtttcacct | 12360 |
| gggtagtcaa agatggatca tgggtctcag tggagagctg agccaggcag gagctgacta | 12420 |
| agggtgagag gtgggagtta gcagcctctg aacatctgtg taccatggga ccccctttcc | 12480 |
| tcctgcatgg taccccagac aaggagccta gtaagagata ctaatggctt gttgtccaga | 12540 |
| gatgttcaaa ctgcagagaa agataagaca acaagcattg gcctccaatc atgatgacag | 12600 |
| ataggaggag gtgggagctc cttagcagtg ctggttggcc ttccatgttc tactgtgggc | 12660 |
| catctctgcc atgtactgta ggctactagc ttctatatta aagaatgcaa gaggggccag | 12720 |
| gagcggaggc tcatgcctgt aatctcagca ctttgggagg ccaaggtggg cagatcactt | 12780 |
| gaggtcagga gtttgtgacc agcctggcca acatggtgaa actctgcctt tactaaaaat | 12840 |
| ataaaaatta gctgggtgtg gtggtgtgca cctgtaatcc cagctactcg ggagactgag | 12900 |
| gcacaagaat tgcttgaacc tgggaggcgg aagttgcagt gagcccagat tgcgccactg | 12960 |
| cactccaccc tgggcaacag agaaagactc tgcctcaaaa aaaaaaaaaa aaagcaagag | 13020 |
| gaagtgaaat aatcaaggcc gccatttaat agtgagcagc cactccatgt ggtactgtgc | 13080 |
| aagcacatta taaatattag cctcacaaga aatgtattag catttgtatt ttgtacactg | 13140 |
| gttaagtatc ttgcccaaga cctcaaaact ggttaagggc agcagaattt agccccagca | 13200 |
| ccacctttc aaagcctggg cttctcacac ttctccatgc tgttcccatt ttaacacagg | 13260 |
| tatctcgcca ttccagccac tcaaactttg gcatttaaga aaattatcct aaagctaaac | 13320 |
| taaacttcaa ggatgaccat tctcctgacc ccttcccatc aaaattttat ctttagtcag | 13380 |
| tttgttttcg ttttgttttg tttttcagaa ctacctctgg cacatcctcc aaatgaaagg | 13440 |

<210> SEQ ID NO 8
<211> LENGTH: 8521
<212> TYPE: DNA
<213> ORGANISM: Artificial Sequence
<220> FEATURE:
<223> OTHER INFORMATION: Polynucleotide (humanization fragment B)

<400> SEQUENCE: 8

| | |
|---|---:|
| gtcacggttc ccaaggacct atatgtggta gagtatggta gcaatatgac aattgaatgc | 60 |
| aaattcccag tagaaaaaca attagacctg gctgcactaa ttgtctattg ggaaatggag | 120 |
| gataagaaca ttattcaatt tgtgcatgga gaggaagacc tgaaggttca gcatagtagc | 180 |
| tacagacaga gggcccggct gttgaaggac cagctctccc tgggaaatgc tgcacttcag | 240 |
| atcacagatg tgaaattgca ggatgcaggg gtgtaccgct gcatgatcag ctatggtggt | 300 |
| gccgactaca agcgaattac tgtgaaagtc aatggtaaga attattatag atgagaggcc | 360 |
| tgatctttat tgaaaacata ttccaagtgt tgaagacttt tcattcttgt aagtccatac | 420 |
| ttattttcaa acagaacagc atagtctgtt cattcattca ttcaattcat gaattcattc | 480 |
| acataattat ccaatttctt gagcacctat ttgatagtca ctggaaatcc agagacaaac | 540 |
| aacacagagc catgttctac agtatgtaca gttttccaaa aagaatttct agtctttact | 600 |

```
tttttattac aaatggaata cgtatacttg caaataattc agatactgtg aagagatca      660 aatgaattgc aaaagtgtcc ctcctccctt caccactatc tcccatggca tgcagagaga     720
gtaaccatta tttgtgtgtc cctccagaaa tttttttatt caactactat tttttttatt    780
tattaggtcc gtcagttttc cttttttgag cctctctata tcaaatgcaa ataaatatat    840
tcagaacaaa ccccactgta aggttcacat taaaaagac ttgaagtcac cctatgaaga     900 caaaaataa tcacattaag tgtgaaagaa cctattcttc cagtacagga taagccatac     960
ttactgggca tatattcatc ttgaaaatct atactgatgt tgtcttgggg aattgaaaag   1020
gaactaggag tgttagttcc tcggtattga cccacagtta tgttatcagg tcacttgagt   1080
tcaaagtttt gtgttggcac tagctaagta aggaaaaca cctctgcttt cattgttgag    1140
tttcacagaa ttgagagctg aaaggatccc aggcaggagc agctaatcca aactcccaca   1200
aagaacaaaa atcccccaga ggatcttctg ttcttatatt tcctgcaatg gcgtccctgt   1260
catatcccac aatggcctcc ctgccatttg gatatccctt ccatatcctg ttgaaattac   1320
tccctaatag taagctgaaa tctgcccctc tagttgtagt cttgggatta tttcatttac   1380
atgatgacct tttaatattt gactagaatt aaatcatctc cccttggtct ttccattcct   1440
gggctaacta ccatcaatct gagggctaac aatacaagta gaaaagtat acatttgtca   1500 ctgatcactg atcaattatt aatcaatgat cactgataac tataaactca aaacaaaat   1560 catgtgggga ttaagagaaa tgtatcagtt ttatgttgta tttctggtcc ctgatactgg   1620
ctcaggtaat gccactattg tcaagaagat accacttgta aagtagattt aattttcatt   1680
atattttacc atatgcttct ccattcatga catctcttga gatgttgtgg tttatacttt   1740 cagttttct ccagtccatc cgcaaatatc aggcatctac tgtgttccaa gatattaaag   1800
aaatcatcat gacttagcct catcaacagc attgctagat ctgggatgga aaggaagagt   1860
ataatcctgg cagtcaggaa gaaggcagca taaagtataa gtttctgctt ccaaaaaagg   1920
tctctcatca gcctgtaggg agtgtgtagg gaagggacag ctgtccttgt agtagggaag   1980
ggttttattc aggtcgtctg ggctccataa tatcccttgt gtatctgcag tctcctttgc   2040
catggatcaa cacaatagga aatcttccgg cactgatggt ttttccaagg gggagttctt   2100
cctggagcaa agcaaatgac caaccaggtt tgaggacctg atttgtttga caattccatt   2160
ttgtattgta aattacttaa ttggcattct actcccaatc catcttgtca tttgcataca   2220
gtggttttgg gattgagttc agctatacca aaagtctgaa ccttctgcac ttagaacaag   2280
gcaaccacca agcttcactt gcactgaggc cgtgtctcca atggaaatga ggcagctggc   2340
ttgcaggagc ttcccaactc agggaagtag aactcctgag tcacctccat atgcaaatga   2400
tttcacagta atgctgttga acttcacttc ccatcacagc aaatgtgtgg taacatagct   2460
tccccacagg agtttactca ccatggtatt ttaaaggtga acatttcaa aactgaaatt    2520 tgaaagaatt tagttttgga ttcactcaat tatcactatc acttcgggtg ttattgcacc   2580
tttcttgttt gtgagtttaa atgccagact ctcaggccac taactttcaa ttaaaagtgt   2640
ttttctttaa tcgctgaacc taacagcagg gaaaacgaaa tgttcattca gactttcaga   2700
accttcaatg agattaggca gctgaaagat caaagtgttg catagttgtc ccgataaagc   2760
tatttggatc atatggacca aatcgactgc tgtcattccc caccaacccc atctctcccc   2820
aaaattccca gccctgttta agtgttctct gtagcattta tctctatcta gtatattgtg   2880
tagcatatca tatcatactt ttctgttttg tttattgtct ctctcctcct agaatataaa   2940
```

```
ctccacaagc acaaagattt gggcctgttt tataatattg ttgcatcccc agggcctgat   3000
atacagcaga gtggtggtac gaaaagagca cacaaaaaaa tatttgttga gtcaatgaat   3060
gaatgatttc ctcaaatagg attagcctaa aattttggaa acatgaacag atttggatat   3120
gtgaaaattt atttccagac tgttcatcag gaactgttag cagcttctaa agggtacact   3180
ggagcagcag tagtaaaagg aggaagagga gcagctctgc tactgctact atcgagtact   3240
actacaatta gcacttgctt attctgtgtg ttaggccctg tactgaacac tctgtctaaa   3300
ttagttcatt tcctcctgga aatgactcta gggggtaagt gcttcatcat gtaagatgag   3360 tattttcac attttgttgt gtctgaaatc tgagtgtgtc tttcaatgat ggaatctttg    3420
attccatgat aagtggtatt attcccattt taaggatgag gaaactgagg tccaaagaaa   3480
ttaagtaatt tgcccaaatt cacccagcct agaaaatgat aaagctagtt ctaaacccaa   3540
gcagattagc tctgaagtct gggcccttaa taaccacttt ttattgccta tatttgtacc   3600
tctggtgtac gtatcaagtt atatgttgac ttcaaaacta tcatgacctt ttcttggttt   3660
tgattgtcca acattagtat agtgttctgg gtctgcaaaa attttgatta ctcatctcat   3720
ctgtaaaaca ttttgaactc gtgtgtttgt gcatgcacat ttgtgtgtaa ttataaaaat   3780
tttactttct gttaatatat aagttgtatc ataagaaact gccgttttg aagagcaaaa    3840 aaaggttgaa tgttaccagt tacatctggt tcaacctaat agacatttgt acaaaaacag   3900
acattttaag aggttgaaat aaaaatttaa taaacaatat tttcagtttt tactaattgt   3960
gatgcttcac tatcattagc taatatgtca aggcataata taccttaggg tgaactttat   4020
cattaacaaa ggtggatggt gtcaataatc ttgaggtttg tgttttttta tataacactg   4080
cgaggtctaa ttaagtactt actgtttacc acctcataca gtggccgata aaaagtgtca   4140
cttctgctgt ttcctctggg ttgtgcttga attattagta ttatcttcag tcctcagttt   4200
ctttgtggga aactttttaa ttagttgttt aattttgtaa gatggttagt ttagtcaaaa   4260
ttagataaga gaatttgaaa atccgtagct accccaaagc aacctacaca taagaactat   4320 tattttgtg ttttgaaatc ataattttat tgatttccag tgtttccact ggtagtggtt    4380
tcattgatat aggagtatca aaacatcact cattatttat ttcagtttca tttgatccta   4440
gccgttttgt attaactctc tgtgaagaaa ttacctcaca aatctattgc tgtcgctagc   4500
tcgctacctt aggaccgtta tagttactag cataacttcg tatagcatac attatacgaa   4560
gttatctcga gcttggtaaa ggaatggaga attaaggctc tagatcatta gtggttacac   4620
tatagtatta gaagtaaaaa aaagattata ccaacaaaat aagaacatgt taatgtactt   4680
gtaatgaata acatgaata aagctcttat gctatatagg tgcactaaac aatctactag     4740
aattgtcagc aaactacgta tcttaatcct gaaagggtcc caaccaatg atctaaaatt     4800 gaatcaaact ttcttccttg agcataatta cttaaatgat ttattaaaat agccagcatt   4860
taaaagctta aaatgtaaat atcataatgt ggtatcctag atagcatccc agaacagaaa   4920
aaggatatta gggaaaaact ggaggaatgg aataaattat gcagtttagt tattaataat   4980
gtactaacgt ccttagttat gacgattgta ccatggtaat gtaagatact aacaatagag   5040
gaaaccgggt aaggagtata cagtaactct atactatctt tgcaactttt ttgtaaattt   5100
aaaacttcta aaataaagaa caaatttaaa cattaaaaag tatcaccagg aacatatatc   5160
actgtttaca gatgaaatac tatgtatttt catatctaat ttctgatcat tgacttcaaa   5220
tcagaaaagt gaatgacacc tcaaaatcag gttttctgtt tactgaagtc taagaaagaa   5280
aagcatacca gctggagaga ttcatgttta taaagacaga tttataacaa caaaaataaa   5340
```

```
atatccaaga ataaatttaa gaagaagcac tttactgaga acatatgaa aacctgaaca    5400 aatggagagg gatattttgt atttgaatag aaagacttct ggtttaaaga taattctctt    5460
taaattattt tttgtagaaa tttaaggggt acaagagcag tgttgtcaca tggatatatt    5520
acatagtggt gaagtctggg gttttagtgt aaattaatct ttacattttg tttgagccca    5580
ataaatgtac caacatgatt tttatagaaa gatagtcatt cctattaatc caaacttgtc    5640
ccaactttga attgaattga ggcagagcta gcaggtgttc cccacggctg aggcatctga    5700
acattaagca tatccctctg agaaccagcc tgcattgata ctctttctaa tgtggacagc    5760
atcaagctat gtacgtagtt ctgtgctcag caaaagccct gacttctttt tgtttatgtc    5820
ctagccccat acaacaaaat caaccaaaga attttggttg tggatccagt cacctctgaa    5880
catgaactga catgtcaggc tgagggctac cccaaggccg aagtcatctg acaagcagt    5940 gaccatcaag tcctgagtgg taagaccacc accaccaatt ccaagagaga ggagaagctt    6000
ttcaatgtga ccagcacact gagaatcaac acaacaacta atgagatttt ctactgcact    6060
tttaggagat tagatcctga ggaaaaccat acagctgaat tggtcatccc aggtaatatt    6120
ctgaatgtgt ccattaaaat atgtctaaca ctgtccccta gcacctagca tgatgtctgc    6180
ctatcatagt cattcagtga ttgttgaata aatgaatgaa tgaataacac tatgtttaca    6240
aaatatatcc taattcctca cctccattca tccaaaccat attgttactt aataaacatt    6300
cagcagatat ttatggaata taccttttgt tccatgcatt gtagtactca ttggatacac    6360
atagaataat aagactcagt tcacactctt caggaaacag ataaaaaact aagaaacaaa    6420
caaaaaacag gcaatccaac accatgtggg aaatgctttc atagccggga aacctgggga    6480
atacctgaga ggaatactca attcaggcct tgtttcagga atccaaatcc tggcacatca    6540
gagctgcttc cctctttcca gggtggcagg aaataaatgg aacatatttt tctatcttat    6600
gccaaacatg agggaccctt tctccccggt gcctctccca aggtagtcta caatatttca    6660
actctagcag tctgcttagt gcatagaaca tgaggctgtg tgtccctggg caaattacta    6720
gacttctgtg tgcttcactt tccctgtagg attataatct actgagcaag cttattgtaa    6780
gggtcagatt agcaacagtg tatgaaaatg atttgagacc attgcctgca caaattcaac    6840
tatttttttt tatctcacta ctctacagaa gtaggtaggg tgggagacag agtctgatga    6900
gaggctcaga atgtgaaaga aagtgaggcg agtgagcatg atatttaata taaacacaaa    6960
gatattctga gaagagctgc tcactgcccc ctcccccaat acatgttgat aggaaaatgc    7020
cacgtacttc agcaaaaaca actgaaaaat tagatagaaa agtcaatcaa taggaaaaga    7080
taatccagga cggtgttgtg aacagaaaga gggggaaaaa actttagaaa atgatgggga    7140
tgctcttact ggggtacgag tcctcaggta ttgaactggc tttcagtaaa agctagatta    7200
gtgggttcct gccatttaca agctgtttta tgacaactta cttgttgggt ggcctacagt    7260
aactcaccta actgcactga gtctgtttcc tcatctgtaa attggggatt tttttttaaa    7320
tacctggcat gcctaactca taaagttgtt ctgaaactga aataaaacat acgtgaacag    7380
gcattgtaaa ctgtaagtta cggaaaaagc tggctgttgt tgtgtcttta agtttcacc    7440 tgggtagtca aagatggatc atgggtctca gtggagagct gagccaggca ggagctgact    7500
aagggtgaga ggtgggagtt agcagcctct gaacatctgt gtaccatggg accccctttc    7560
ctcctgcatg gtaccccaga caaggagcct agtaagagat actaatggct tgttgtccag    7620
agatgttcaa actgcagaga aagataagac aacaagcatt ggcctccaat catgatgaca    7680
```

| | |
|---|---|
| gataggagga ggtgggagct ccttagcagt gctggttggc cttccatgtt ctactgtggg | 7740 |
| ccatctctgc catgtactgt aggctactag cttctatatt aaagaatgca agagggggcca | 7800 |
| ggagcggagg ctcatgcctg taatctcagc actttgggag gccaaggtgg gcagatcact | 7860 |
| tgaggtcagg agtttgtgac cagcctggcc aacatggtga aactctgcct ttactaaaaa | 7920 |
| tataaaaatt agctgggtgt ggtggtgtgc acctgtaatc ccagctactc gggagactga | 7980 |
| ggcacaagaa ttgcttgaac ctgggaggcg aagttgcag tgagcccaga ttgcgccact | 8040 |
| gcactccacc ctgggcaaca gagaaagact ctgcctcaaa aaaaaaaaa aaaagcaaga | 8100 |
| ggaagtgaaa taatcaaggc cgccatttaa tagtgagcag ccactccatg tggtactgtg | 8160 |
| caagcacatt ataaatatta gcctcacaag aaatgtatta gcatttgtat tttgtacact | 8220 |
| ggttaagtat cttgcccaag acctcaaaac tggttaaggg cagcagaatt tagccccagc | 8280 |
| accacctttt caaagcctgg gcttctcaca cttctccatg ctgttcccat tttaacacag | 8340 |
| gtatctcgcc attccagcca ctcaaacttt ggcatttaag aaaattatcc taaagctaaa | 8400 |
| ctaaacttca aggatgacca ttctcctgac cccttcccat caaaattttta tctttagtca | 8460 |
| gtttgttttc gttttgtttt gtttttcaga actacctctg gcacatcctc caaatgaaag | 8520 |
| g | 8521 |

<210> SEQ ID NO 9
<211> LENGTH: 4494
<212> TYPE: DNA
<213> ORGANISM: Artificial Sequence
<220> FEATURE:
<223> OTHER INFORMATION: Polynucleotide (humanization fragment C)

<400> SEQUENCE: 9

| | |
|---|---|
| gtcacggttc ccaaggacct atatgtggta gagtatggta gcaatatgac aattgaatgc | 60 |
| aaattcccag tagaaaaaca attagacctg gctgcactaa ttgtctattg ggaaatggag | 120 |
| gataagaaca ttattcaatt tgtgcatgga gaggaagacc tgaaggttca gcatagtagc | 180 |
| tacagacaga gggcccggct gttgaaggac cagctctccc tgggaaatgc tgcacttcag | 240 |
| atcacagatg tgaaattgca ggatgcaggg gtgtaccgct gcatgatcag ctatggtggt | 300 |
| gccgactaca agcgaattac tgtgaaagtc aatggtaaga attattatag atgagaggcc | 360 |
| tgatctttat tgaaaacata ttccaagtgt tgaagacttt tcattcttgt aagtccatac | 420 |
| ttattttcaa acagaacagc atagtctgtt cattcattca ttcaattcat gaattcattc | 480 |
| acataattat ccaatttctt gagcaccat ttgatagtca ctggaaatcc agagacaaac | 540 |
| aacacagagc catgttctac agtatgtaca gttttccaaa aagaatttct agtctttact | 600 |
| tttttattac aaatggaata cgtatacttg caaataattc agatactgtg aagagatca | 660 |
| aatgaattgc aaaagtgtcc ctcctcctt caccactatc tcccatggca tgcagagaga | 720 |
| gtaaccatta tttgtgtgtc cctccagaaa ttttttatt caactactat ttttttattt | 780 |
| tattaggtcc gtcagttttc ctttttgag cctctctata tcaaatgcaa ataaatatat | 840 |
| tcagaacaaa ccccactgta aggttcacat taaaaagac ttgaagtcac cctatgaaga | 900 |
| caaaaaataa tcacattaag tgtgaaagaa cctattcttc cagtacagga taagccatac | 960 |
| ttactgggca tatattcatc ttgaaaatct atactgatgt tgtcttgggg aattgaaaag | 1020 |
| gaactaggag tgttagttcc tcggtattga cccacagtta tgttatcagg tcacttgagt | 1080 |
| tcaaagttttt gtgttggcac tagctaagta aggaaaaca cctctgcttt cattgttgag | 1140 |
| tttcacagaa ttgagagctg aaaggatccc aggcaggagc agctaatcca aactcccaca | 1200 |

```
aagaacaaaa atcccccaga ggatcttctg ttcttatatt tcctgcaatg gcgtccctgt    1260
catatcccac aatggcctcc ctgccatttg gatatccctt ccatatcctg ttgaaattac    1320
tccctaatag taagctgaaa tctgcccctc tagttgtagt cttgggatta tttcatttac    1380
atgatgacct tttaatattt gactagaatt aaatcatctc cccttggtct ttccattcct    1440
gggctaacta ccatcaatct gagggctaac aatacaagta gaaaaagtat acatttgtca    1500
ctgatcactg atcaattatt aatcaatgat cactgataac tataaactca aaacaaaat     1560 catgtgggga ttaagagaaa tgtatcagtt ttatgttgta tttctggtcc ctgatactgg    1620
ctcaggtaat gccactattg tcaagaagat accacttgta aagtagattt aattttcatt    1680
atattttacc atatgcttct ccattcatga catctcttga gatgttgtgg tttatacttt    1740 cagttttttct ccagtccatc cgcaaatatc aggcatctac tgtgttccaa gatattaaag   1800
aaatcatcat gacttagcct catcaacagc attgctagat ctgggatgga aaggaagagt    1860
ataatcctgg cagtcaggaa gaaggcagca taaagtataa gtttctgctt ccaaaaaagg    1920
tctctcatca gcctgtaggg agtgtgtagg gaagggacag ctgtccttgt agtagggaag    1980
ggttttattc aggtcgtctg ggctccataa tatcccttgt gtatctgcag tctcctttgc    2040
catggatcaa cacaatagga aatcttccgg cactgatggt ttttccaagg gggagttctt    2100
cctggagcaa agcaaatgac caaccaggtt tgaggacctg atttgtttga caattccatt    2160
ttgtattgta aattacttaa ttggcattct actcccaatc catcttgtca tttgcataca    2220
gtggttttgg gattgagttc agctatacca aaagtctgaa ccttctgcac ttagaacaag    2280
gcaaccacca agcttcactt gcactgaggc cgtgtctcca atggaaatga ggcagctggc    2340
ttgcaggagc ttcccaactc agggaagtag aactcctgag tcacctccat atgcaaatga    2400
tttcacagta atgctgttga acttcacttc ccatcacagc aaatgtgtgg taacatagct    2460
tccccacagg agtttactca ccatggtatt ttaaaggtga aacatttcaa aactgaaatt    2520
tgaaagaatt tagttttgga ttcactcaat tatcactatc acttcgggtg ttattgcacc    2580
tttcttgttt gtgagtttaa atgccagact ctcaggccac taactttcaa ttaaaagtgt    2640 ttttcttaa tcgctgaacc taacagcagg gaaaacgaaa tgttcattca gactttcaga    2700
accttcaatg agattaggca gctgaaagat caaagtgttg catagttgtc ccgataaagc    2760
tatttggatc atatggacca aatcgactgc tgtcattccc caccaacccc atctctcccc    2820
aaaattccca gccctgttta agtgttctct gtagcattta tctctatcta gtatattgtg    2880
tagcatatca tatcatactt ttctgttttg tttattgtct ctctcctcct agaatataaa    2940
ctccacaagc acaaagattt gggcctgttt tataatattg ttgcatcccc agggcctgat    3000
atacagcaga gtggtggtac gaaaagagca cacaaaaaaa tatttgttga gtcaatgaat    3060
gaatgatttc ctcaaatagg attagcctaa aattttggaa acatgaacag atttggatat    3120
gtgaaaattt atttccagac tgttcatcag gaactgttag cagcttctaa agggtacact    3180
ggagcagcag tagtaaaagg aggaagagga gcagctctgc tactgctact atcgagtact    3240
actacaatta gcacttgctt attctgtgtg ttaggccctg tactgaacac tctgtctaaa    3300
ttagttcatt tcctcctgga aatgactcta gggggtaagt gcttcatcat gtaagatgag    3360
tatttttcac attttgttgt gtctgaaatc tgagtgtgtc tttcaatgat ggaatctttg    3420
attccatgat aagtggtatt attcccattt taaggatgag gaaactgagg tccaaagaaa    3480
ttaagtaatt tgcccaaatt cacccagcct agaaaatgat aaagctagtt ctaaacccaa    3540
```

```
gcagattagc tctgaagtct gggcccttaa taaccacttt ttattgccta tatttgtacc   3600
tctggtgtac gtatcaagtt atatgttgac ttcaaaacta tcatgacctt ttcttggttt   3660
tgattgtcca acattagtat agtgttctgg gtctgcaaaa attttgatta ctcatctcat   3720
ctgtaaaaca ttttgaactc gtgtgtttgt gcatgcacat ttgtgtgtaa ttataaaaat   3780
tttactttct gttaatatat aagttgtatc ataagaaact gccgtttttg aagagcaaaa   3840
aaaggttgaa tgttaccagt tacatctggt tcaacctaat agacatttgt acaaaaacag   3900 acatttaag aggttgaaat aaaaatttaa taaacaatat tttcagtttt tactaattgt   3960
gatgcttcac tatcattagc taatatgtca aggcataata taccttaggg tgaacttttat  4020 cattaacaaa ggtggatggt gtcaataatc ttgaggtttg tgttttttta tataacactg   4080
cgaggtctaa ttaagtactt actgtttacc acctcataca gtggccgata aaagtgtca    4140 cttctgctgt ttcctctggg ttgtgcttga attattagta ttatcttcag tcctcagttt   4200
ctttgtggga aacttttttaa ttagttgttt aattttgtaa gatggttagt ttagtcaaaa   4260
ttagataaga gaatttgaaa atccgtagct accccaaagc aacctacaca taagaactat   4320
tatttttgtg ttttgaaatc ataatttttat tgatttccag tgtttccact ggtagtggtt   4380
tcattgatat aggagtatca aaacatcact cattatttat ttcagtttca tttgatccta   4440
gccgttttgt attaactctc tgtgaagaaa ttacctcaca aatctattgc tgtc          4494

<210> SEQ ID NO 10
<211> LENGTH: 3950
<212> TYPE: DNA
<213> ORGANISM: Artificial Sequence
<220> FEATURE:
<223> OTHER INFORMATION: Polynucleotide (humanization fragment D)

<400> SEQUENCE: 10
cttggtaaag gaatggagaa ttaaggctct agatcattag tggttacact atagtattag     60
aagtaaaaaa aagattatac caacaaaata agaacatgtt aatgtacttg taatgaataa    120
acatgaataa agctcttatg ctatataggt gcactaaaca atctactaga attgtcagca    180
aactacgtat cttaatcctg aaagggtccc aaaccaatga tctaaaattg aatcaaactt    240
tcttccttga gcataattac ttaaatgatt tattaaaata gccagcattt aaaagcttaa    300
aatgtaaata tcataatgtg gtatcctaga tagcatccca gaacagaaaa aggatattag    360
ggaaaaactg gaggaatgga ataaattatg cagtttagtt attaataatg tactaacgtc    420
cttagttatg acgattgtac catggtaatg taagatacta acaatagagg aaaccgggta    480
aggagtatac agtaactcta tactatcttt gcaactttttt tgtaaattta aaacttctaa    540
aataaagaac aaatttaaac attaaaaagt atcaccagga acatatatca ctgtttacag    600
atgaaatact atgtattttc atatctaatt tctgatcatt gacttcaaat cagaaaagtg    660
aatgacacct caaaatcagg ttttctgttt actgaagtct aagaaaagaa agcataccag    720
ctggagagat tcatgtttat aaagacagat ttataacaac aaaaataaaa tatccaagaa    780
taaatttaag aagaagcact ttactgagaa acatatgaaa acctgaacaa atggagaggg    840
atattttgta tttgaataga aagacttctg gtttaaagat aattctcttt aaattatttt    900
ttgtagaaat ttaggggta caagagcagt gttgtcacat ggatatatta catagtggtg     960
aagtctgggg tttagtgta aattaatctt tacattttgt ttgagcccaa taaatgtacc    1020
aacatgattt ttatagaaag atagtcattc ctattaatcc aaacttgtcc caactttgaa    1080
ttgaattgag gcagagctag caggtgttcc ccacggctga ggcatctgaa cattaagcat   1140
```

```
atccctctga gaaccagcct gcattgatac tctttctaat gtggacagca tcaagctatg   1200
tacgtagttc tgtgctcagc aaaagccctg acttctttt gtttatgtcc tagccccata    1260
caacaaaatc aaccaaagaa ttttggttgt ggatccagtc acctctgaac atgaactgac   1320
atgtcaggct gagggctacc ccaaggccga agtcatctgg acaagcagtg accatcaagt   1380
cctgagtggt aagaccacca ccaccaattc aagagagag gagaagcttt tcaatgtgac    1440
cagcacactg agaatcaaca caacaactaa tgagattttc tactgcactt ttaggagatt   1500
agatcctgag gaaaaccata cagctgaatt ggtcatccca ggtaatattc tgaatgtgtc   1560
cattaaaata tgtctaacac tgtcccctag cacctagcat gatgtctgcc tatcatagtc   1620
attcagtgat tgttgaataa atgaatgaat gaataacact atgtttacaa aatatatcct   1680
aattcctcac ctccattcat ccaaaccata ttgttactta ataaacattc agcagatatt   1740
tatggaatat accttttgtt ccatgcattg tagtactcat tggatacaca tagaataata   1800
agactcagtt cacactcttc aggaaacaga taaaaaacta agaaacaaac aaaaaacagg   1860
caatccaaca ccatgtggga aatgctttca tagccgggaa acctgggaa tacctgagag    1920 gaatactcaa ttcaggcctt gtttcaggaa tccaaatcct ggcacatcag agctgcttcc   1980 ctcttttccag ggtggcagga aataaatgga acatattttt ctatcttatg ccaaacatga  2040
gggacccttt ctccccggtg cctctcccaa ggtagtctac aatatttcaa ctctagcagt   2100
ctgcttagtg catagaacat gaggctgtgt gtccctgggc aaattactag acttctgtgt   2160
gcttcacttt ccctgtagga ttataatcta ctgagcaagc ttattgtaag ggtcagatta   2220
gcaacagtgt atgaaaatga tttgagacca ttgcctgcac aaattcaact attttttttt    2280
atctcactac tctacagaag taggtaggt gggagacaga gtctgatgag aggctcagaa    2340
tgtgaaagaa agtgaggcga gtgagcatga tatttaatat aaacacaaag atattctgag   2400
aagagctgct cactgccccc tcccccaata catgttgata ggaaaatgcc acgtacttca   2460
gcaaaaacaa ctgaaaaatt agatagaaaa gtcaatcaat aggaaaagat aatccaggac   2520
ggtgttgtga acagaaagag ggggaaaaaa ctttagaaaa tgatggggat gctcttactg   2580
gggtacgagt cctcaggtat tgaactggct ttcagtaaaa gctagattag tgggttcctg   2640
ccatttacaa gctgttttat gacaacttac ttgttgggtg gcctacagta actcacctaa   2700
ctgcactgag tctgttcct catctgtaaa ttggggattt ttttttaaat acctggcatg   2760
cctaactcat aaagttgttc tgaaactgaa ataaacata cgtgaacagg cattgtaaac    2820
tgtaagttac ggaaaaagct ggctgttgtt gtgtctttaa agtttcacct gggtagtcaa   2880
agatggatca tgggtctcag tggagagctg agccaggcag gagctgacta agggtgagag   2940
gtgggagtta gcagcctctg aacatctgtg taccatggga cccccttttcc tcctgcatgg  3000 taccccagac aaggagccta gtaagagata ctaatggctt gttgtccaga gatgttcaaa   3060
ctgcagagaa agataagaca acaagcattg gcctccaatc atgatgacag ataggaggag   3120
gtgggagctc cttagcagtg ctggttggcc ttccatgttc tactgtgggc catctctgcc   3180
atgtactgta ggctactagc ttctatatta aagaatgcaa gaggggccag gagcggaggc   3240
tcatgcctgt aatctcagca ctttgggagg ccaaggtggg cagatcactt gaggtcagga   3300
gtttgtgacc agcctggcca acatggtgaa actctgcctt tactaaaaat ataaaaatta   3360
gctgggtgtg gtggtgtgca cctgtaatcc cagctactcg ggagactgag gcacaagaat   3420
tgcttgaacc tgggaggcgg aagttgcagt gagcccagat tgcgccactg cactccaccc   3480
```

| | |
|---|---|
| tgggcaacag agaaagactc tgcctcaaaa aaaaaaaaaa aaagcaagag gaagtgaaat | 3540 |
| aatcaaggcc gccatttaat agtgagcagc cactccatgt ggtactgtgc aagcacatta | 3600 |
| taaatattag cctcacaaga aatgtattag catttgtatt ttgtacactg gttaagtatc | 3660 |
| ttgcccaaga cctcaaaact ggttaagggc agcagaattt agccccagca ccaccttttc | 3720 |
| aaagcctggg cttctcacac ttctccatgc tgttcccatt ttaacacagg tatctcgcca | 3780 |
| ttccagccac tcaaactttg gcatttaaga aaattatcct aaagctaaac taaacttcaa | 3840 |
| ggatgaccat tctcctgacc ccttcccatc aaaatttat ctttagtcag tttgttttcg | 3900 |
| ttttgttttg tttttcagaa ctacctctgg cacatcctcc aaatgaaagg | 3950 |

<210> SEQ ID NO 11
<211> LENGTH: 8444
<212> TYPE: DNA
<213> ORGANISM: Artificial Sequence
<220> FEATURE:
<223> OTHER INFORMATION: Polynucleotide (humanization fragment E)

<400> SEQUENCE: 11

| | |
|---|---|
| gtcacggttc ccaaggacct atatgtggta gagtatggta gcaatatgac aattgaatgc | 60 |
| aaattcccag tagaaaaaca attagacctg gctgcactaa ttgtctattg ggaaatggag | 120 |
| gataagaaca ttattcaatt tgtgcatgga gaggaagacc tgaaggttca gcatagtagc | 180 |
| tacagacaga gggcccggct gttgaaggac cagctctccc tgggaaatgc tgcacttcag | 240 |
| atcacagatg tgaaattgca ggatgcaggg gtgtaccgct gcatgatcag ctatggtggt | 300 |
| gccgactaca gcgaattac tgtgaaagtc aatggtaaga attattatag atgagaggcc | 360 |
| tgatctttat tgaaaacata ttccaagtgt tgaagacttt tcattcttgt aagtccatac | 420 |
| ttattttcaa acagaacagc atagtctgtt cattcattca ttcaattcat gaattcattc | 480 |
| acataattat ccaatttctt gagcacctat ttgatagtca ctggaaatcc agagacaaac | 540 |
| aacacagagc catgttctac agtatgtaca gttttccaaa aagaatttct agtctttact | 600 |
| tttttattac aaatggaata cgtatacttg caaataattc agatactgtg aagagatca | 660 |
| aatgaattgc aaaagtgtcc ctcctcccct caccactatc tcccatggca tgcagagaga | 720 |
| gtaaccatta tttgtgtgtc cctccagaaa tttttttatt caactactat tttttattt | 780 |
| tattaggtcc gtcagttttc cttttttgag cctctctata tcaaatgcaa ataaatatat | 840 |
| tcagaacaaa ccccactgta aggttcacat taaaaaagac ttgaagtcac cctatgaaga | 900 |
| caaaaaataa tcacattaag tgtgaaagaa cctattcttc cagtacagga taagccatac | 960 |
| ttactgggca tatattcatc ttgaaaatct atactgatgt tgtcttgggg aattgaaaag | 1020 |
| gaactaggag tgttagttcc tcggtattga cccacagtta tgttatcagg tcacttgagt | 1080 |
| tcaaagtttt gtgttggcac tagctaagta aaggaaaaca cctctgcttt cattgttgag | 1140 |
| tttcacagaa ttgagagctg aaaggatccc aggcaggagc agctaatcca aactcccaca | 1200 |
| aagaacaaaa atcccccaga ggatcttctg ttcttatatt tcctgcaatg gcgtccctgt | 1260 |
| catatcccac aatggcctcc ctgccatttg gatatccctt ccatatcctg ttgaaattac | 1320 |
| tccctaatag taagctgaaa tctgcccctc tagttgtagt cttgggatta tttcatttac | 1380 |
| atgatgacct tttaatattt gactagaatt aaatcatctc cccttggtct ttccattcct | 1440 |
| gggctaacta ccatcaatct gagggctaac aatacaagta gaaaagtat acatttgtca | 1500 |
| ctgatcactg atcaattatt aatcaatgat cactgataac tataaactca aaacaaaat | 1560 |
| catgtgggga ttaagagaaa tgtatcagtt ttatgttgta tttctggtcc ctgatactgg | 1620 |

```
ctcaggtaat gccactattg tcaagaagat accacttgta aagtagattt aattttcatt    1680
atattttacc atatgcttct ccattcatga catctcttga gatgttgtgg tttatacttt    1740
cagttttcct ccagtccatc cgcaaatatc aggcatctac tgtgttccaa gatattaaag    1800
aaatcatcat gacttagcct catcaacagc attgctagat ctgggatgga aaggaagagt    1860
ataatcctgg cagtcaggaa gaaggcagca taaagtataa gtttctgctt ccaaaaaagg    1920
tctctcatca gcctgtaggg agtgtgtagg gaagggacag ctgtccttgt agtagggaag    1980
ggttttattc aggtcgtctg ggctccataa tatcccttgt gtatctgcag tctcctttgc    2040
catggatcaa cacaatagga aatcttccgg cactgatggt ttttccaagg gggagttctt    2100
cctggagcaa agcaaatgac caaccaggtt tgaggacctg atttgtttga caattccatt    2160
ttgtattgta aattacttaa ttggcattct actcccaatc catcttgtca tttgcataca    2220
gtggttttgg gattgagttc agctatacca aaagtctgaa ccttctgcac ttagaacaag    2280
gcaaccacca agcttcactt gcactgaggc cgtgtctcca atggaaatga ggcagctggc    2340
ttgcaggagc ttcccaactc agggaagtag aactcctgag tcacctccat atgcaaatga    2400
tttcacagta atgctgttga acttcacttc ccatcacagc aaatgtgtgg taacatagct    2460
tccccacagg agtttactca ccatggtatt ttaaaggtga acatttcaa aactgaaatt     2520
tgaaagaatt tagttttgga ttcactcaat tatcactatc acttcgggtg ttattgcacc    2580
tttcttgttt gtgagtttaa atgccagact ctcaggccac taactttcaa ttaaaagtgt    2640
ttttctttaa tcgctgaacc taacagcagg gaaaacgaaa tgttcattca gactttcaga    2700
accttcaatg agattaggca gctgaaagat caaagtgttg catagttgtc ccgataaagc    2760
tatttggatc atatgaccaa atcgactgc tgtcattccc caccaacccc atctctcccc     2820
aaaattccca gccctgttta agtgttctct gtagcattta tctctatcta gtatattgtg    2880
tagcatatca tatcatactt ttctgttttg tttattgtct ctctcctcct agaatataaa    2940
ctccacaagc acaaagattt gggcctgttt tataatattg ttgcatcccc agggcctgat    3000
atacagcaga gtggtggtac gaaaagagca cacaaaaaaa tatttgttga gtcaatgaat    3060
gaatgatttc ctcaaatagg attagcctaa aatttggaa acatgaacag atttggatat     3120
gtgaaaattt atttccagac tgttcatcag gaactgttag cagcttctaa agggtacact    3180
ggagcagcag tagtaaaagg aggaagagga gcagctctgc tactgctact atcgagtact    3240
actacaatta gcacttgctt attctgtgtg ttaggccctg tactgaacac tctgtctaaa    3300
ttagttcatt tcctcctgga aatgactcta ggggtaagt gcttcatcat gtaagatgag      3360
tattttcac attttgttgt gtctgaaatc tgagtgtgtc tttcaatgat ggaatctttg      3420
attccatgat aagtggtatt attcccattt taaggatgag gaaactgagg tccaaagaaa    3480
ttaagtaatt tgcccaaatt cacccagcct agaaaatgat aaagctagtt ctaaacccaa    3540
gcagattagc tctgaagtct gggcccttaa taaccacttt ttattgccta tatttgtacc    3600
tctggtgtac gtatcaagtt atatgttgac ttcaaaacta tcatgacctt ttcttggttt    3660
tgattgtcca acattagtat agtgttctgg gtctgcaaaa attttgatta ctcatctcat    3720
ctgtaaaaca ttttgaactc gtgtgtttgt gcatgcacat ttgtgtgtaa ttataaaaat    3780
tttactttct gttaatatat aagttgtatc ataagaaact gccgttttg aagagcaaaa      3840
aaaggttgaa tgttaccagt tacatctggt tcaacctaat agacatttgt acaaaaacag    3900
acattttaag aggttgaaat aaaaatttaa taaacaatat tttcagtttt tactaattgt    3960
```

```
gatgcttcac tatcattagc taatatgtca aggcataata taccttaggg tgaactttat    4020
cattaacaaa ggtggatggt gtcaataatc ttgaggtttg tgttttttta tataacactg    4080
cgaggtctaa ttaagtactt actgtttacc acctcataca gtggccgata aaaagtgtca    4140
cttctgctgt ttcctctggg ttgtgcttga attattagta ttatcttcag tcctcagttt    4200
ctttgtggga aacttttaa ttagttgttt aattttgtaa gatggttagt ttagtcaaaa    4260
ttagataaga gaatttgaaa atccgtagct accccaaagc aacctacaca taagaactat    4320
tattttgtg ttttgaaatc ataattttat tgatttccag tgtttccact ggtagtggtt    4380
tcattgatat aggagtatca aaacatcact cattatttat ttcagtttca tttgatccta    4440
gccgttttgt attaactctc tgtgaagaaa ttacctcaca aatctattgc tgtccttggt    4500
aaaggaatgg agaattaagg ctctagatca ttagtggtta cactatagta ttagaagtaa    4560
aaaaaagatt ataccaacaa aataagaaca tgttaatgta cttgtaatga ataaacatga    4620
ataaagctct tatgctatat aggtgcacta acaatctac tagaattgtc agcaaactac    4680
gtatcttaat cctgaaaggg tcccaaacca atgatctaaa attgaatcaa actttcttcc    4740
ttgagcataa ttacttaaat gatttattaa aatagccagc atttaaaagc ttaaaatgta    4800
aatatcataa tgtggtatcc tagatagcat cccagaacag aaaaaggata ttagggaaaa    4860
actggaggaa tggaataaat tatgcagttt agttattaat aatgtactaa cgtccttagt    4920
tatgacgatt gtaccatggt aatgtaagat actaacaata gaggaaaccg ggtaaggagt    4980
atacagtaac tctatactat ctttgcaact ttttgtaaa tttaaaactt ctaaaataaa    5040
gaacaaattt aaacattaaa aagtatcacc aggaacatat atcactgttt acagatgaaa    5100
tactatgtat tttcatatct aatttctgat cattgacttc aaatcagaaa agtgaatgac    5160
acctcaaaat caggttttct gtttactgaa gtctaagaaa agaaagcata ccagctggag    5220
agattcatgt ttataaagac agatttataa caacaaaaat aaaatatcca agaataaatt    5280
taagaagaag cactttactg agaaacatat gaaaacctga acaaatggag agggatattt    5340
tgtatttgaa tagaaagact tctggtttaa agataattct ctttaaatta ttttttgtag    5400
aaatttaagg ggtacaagag cagtgttgtc acatggatat attacatagt ggtgaagtct    5460
ggggttttag tgtaaattaa tctttacatt ttgtttgagc ccaataaatg taccaacatg    5520
atttttatag aaagatagtc attcctatta atccaaactt gtcccaactt tgaattgaat    5580
tgaggcagag ctagcaggtg ttccccacgg ctgaggcatc tgaacattaa gcatatccct    5640
ctgagaacca gcctgcattg atactctttc taatgtggac agcatcaagc tatgtacgta    5700
gttctgtgct cagcaaaagc cctgacttct ttttgtttat gtcctagccc catacaacaa    5760
aatcaaccaa agaattttgg ttgtggatcc agtcacctct gaacatgaac tgacatgtca    5820
ggctgagggc taccccaagg ccgaagtcat ctggacaagc agtgaccatc aagtcctgag    5880
tggtaagacc accaccacca attccaagag agaggagaag cttttcaatg tgaccagcac    5940
actgagaatc aacacaacaa ctaatgagat tttctactgc acttttagga gattagatcc    6000
tgaggaaaac catacagctg aattggtcat cccaggtaat attctgaatg tgtccattaa    6060
aatatgtcta acactgtccc ctagcaccta gcatgatgtc tgcctatcat agtcattcag    6120
tgattgttga ataaatgaat gaatgaataa cactatgttt acaaaatata tcctaattcc    6180
tcacctccat tcatccaaac catattgtta cttaataaac attcagcaga tatttatgga    6240
atataccttt tgttccatgc attgtagtac tcattggata cacatagaat aataagactc    6300
agttcacact cttcaggaaa cagataaaaa actaagaaac aaacaaaaaa caggcaatcc    6360
```

```
aacaccatgt gggaaatgct ttcatagccg ggaaacctgg ggaatacctg agaggaatac    6420
tcaattcagg ccttgtttca ggaatccaaa tcctggcaca tcagagctgc ttccctcttt    6480
ccagggtggc aggaaataaa tggaacatat ttttctatct tatgccaaac atgagggacc    6540
ctttctcccc ggtgcctctc ccaaggtagt ctacaatatt tcaactctag cagtctgctt    6600
agtgcataga acatgaggct gtgtgtccct gggcaaatta ctagacttct gtgtgcttca    6660 cttccctgt aggattataa tctactgagc aagcttattg taagggtcag attagcaaca     6720
gtgtatgaaa atgatttgag accattgcct gcacaaattc aactattttt ttttatctca    6780
ctactctaca gaagtaggta gggtgggaga cagagtctga tgagaggctc agaatgtgaa    6840
agaaagtgag gcgagtgagc atgatattta atataaacac aaagatattc tgagaagagc    6900
tgctcactgc cccctccccc aatacatgtt gataggaaaa tgccacgtac ttcagcaaaa    6960
acaactgaaa aattagatag aaaagtcaat caataggaaa agataatcca ggacggtgtt    7020
gtgaacagaa agagggggaa aaactttag aaaatgatgg ggatgctctt actggggtac     7080
gagtcctcag gtattgaact ggctttcagt aaaagctaga ttagtgggtt cctgccattt    7140
acaagctgtt ttatgacaac ttacttgttg ggtggcctac agtaactcac ctaactgcac    7200
tgagtctgtt tcctcatctg taaattgggg atttttttt aaatacctgg catgcctaac     7260
tcataaagtt gttctgaaac tgaaataaaa catacgtgaa caggcattgt aaactgtaag    7320
ttacggaaaa agctggctgt tgttgtgtct ttaaagtttc acctgggtag tcaaagatgg    7380
atcatgggtc tcagtggaga gctgagccag gcaggagctg actaagggtg agaggtggga    7440
gttagcagcc tctgaacatc tgtgtaccat gggaccccct ttcctcctgc atggtacccc    7500
agacaaggag cctagtaaga gatactaatg gcttgttgtc cagagatgtt caaactgcag    7560
agaaagataa gacaacaagc attggcctcc aatcatgatg acagatagga ggaggtggga    7620
gctccttagc agtgctggtt ggccttccat gttctactgt gggccatctc tgccatgtac    7680
tgtaggctac tagcttctat attaaagaat gcaagagggg ccaggagcgg aggctcatgc    7740
ctgtaatctc agcactttgg gaggccaagg tgggcagatc acttgaggtc aggagtttgt    7800
gaccagcctg gccaacatgg tgaaactctg cctttactaa aaatataaaa attagctggg    7860
tgtggtggtg tgcacctgta atcccagcta ctcgggagac tgaggcacaa gaattgcttg    7920
aacctgggag gcggaagttg cagtgagccc agattgcgcc actgcactcc acctgggca     7980 acagagaaag actctgcctc aaaaaaaaaa aaaaaaagca agaggaagtg aaataatcaa    8040
ggccgccatt taatagtgag cagccactcc atgtggtact gtgcaagcac attataaata    8100
ttagcctcac aagaaatgta ttagcatttg tattttgtac actggttaag tatcttgccc    8160
aagacctcaa aactggttaa gggcagcaga atttagcccc agcaccacct tttcaaagcc    8220
tgggcttctc acacttctcc atgctgttcc cattttaaca caggtatctc gccattccag    8280
ccactcaaac tttggcattt aagaaaatta tcctaaagct aaactaaact tcaaggatga    8340
ccattctcct gaccccttcc catcaaaatt ttatctttag tcagtttgtt ttcgttttgt    8400
tttgtttttc agaactacct ctggcacatc ctccaaatga aagg                     8444
```

<210> SEQ ID NO 12
<211> LENGTH: 111
<212> TYPE: DNA
<213> ORGANISM: Artificial Sequence
<220> FEATURE:
<223> OTHER INFORMATION: Synthetic oligonucleotide

<400> SEQUENCE: 12
aactacctct ggcacatcct ccaaatgaaa ggactcactg ggtgcttctg ggatccatcc      60
tgttgttcct cattgtagtg tccacggtcc tcctcttctt gagaaaacaa g             111

<210> SEQ ID NO 13
<211> LENGTH: 159
<212> TYPE: DNA
<213> ORGANISM: Artificial Sequence
<220> FEATURE:
<223> OTHER INFORMATION: Synthetic oligonucleotide

<400> SEQUENCE: 13 taaccttta cccaggtttt cagatgtgtt tggaggagtt ttctgtcttc tgagggctgg      60
tcctctttcc ttttcagcgt ttactgtcag gttcccaagg acctatatgt ggtagagtat   120
ggtagcaata tgacaattga atgcaaattc ccagtagaa                           159

<210> SEQ ID NO 14
<211> LENGTH: 240
<212> TYPE: DNA
<213> ORGANISM: Artificial Sequence
<220> FEATURE:
<223> OTHER INFORMATION: Synthetic oligonucleotide

<400> SEQUENCE: 14
tttgtattaa ctctctgtga agaaattacc tcacaaatct attgctgtcg ctagctcgct      60
accttaggac cgttatagtt actagcataa cttcgtatag catacattat acgaagttat   120
tccagacatg ataagataca ttgatgagtt tggacaaacc acaactagaa tgcagtgaaa   180
aaaatgcttt atttgtgaaa tttgtgatgc tattgcttta tttgtaacca ttataagctg   240

<210> SEQ ID NO 15
<211> LENGTH: 240
<212> TYPE: DNA
<213> ORGANISM: Artificial Sequence
<220> FEATURE:
<223> OTHER INFORMATION: Synthetic oligonucleotide

<400> SEQUENCE: 15
gtgaggaggg gggcgcccgc gggaggcgcc aaaacccggc gcggaggcca tgcatataac      60
ttcgtatagc atacattata cgaagttatc tcgagcttgg taaaggaatg gagaattaag   120
gctctagatc attagtggtt acactatagt attagaagta aaaaaagat tataccaaca    180 aaataagaac atgttaatgt acttgtaatg aataaacatg aataaagctc ttatgctata   240

<210> SEQ ID NO 16
<211> LENGTH: 169
<212> TYPE: DNA
<213> ORGANISM: Artificial Sequence
<220> FEATURE:
<223> OTHER INFORMATION: Synthetic oligonucleotide

<400> SEQUENCE: 16
tttatcttta gtcagtttgt tttcgttttg ttttgttttt cagaactacc tctggcacat      60
cctccaaatg aaaggactca ctgggtgctt ctgggatcca tcctgttgtt cctcattgta   120
gtgtccacgg tcctcctctt cttgagaaaa caaggtattt cctccattg               169

<210> SEQ ID NO 17
<211> LENGTH: 230
<212> TYPE: DNA
<213> ORGANISM: Artificial Sequence

```
<220> FEATURE:
<223> OTHER INFORMATION: Synthetic oligonucleotide

<400> SEQUENCE: 17
tcctagccgt tttgtattaa ctctctgtga agaaattacc tcacaaatct attgctgtcg      60
ctagctcgct accttaggac cgttatagtt actagcataa cttcgtatag catacattat     120
acgaagttat ctcgagcttg gtaaaggaat ggagaattaa ggctctagat cattagtggt     180
tacactatag tattagaagt aaaaaaaaga ttataccaac aaaataagaa                 230

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
ccggctgttg aaggaccag                                                    19

<210> SEQ ID NO 19
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 19
tctccctggg aaatgctgca cttcag                                            26

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 20
tgcatcctgc aatttcacat ctg                                               23

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
acacaggtat ctcgccattc c                                                 21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
agccactcaa actttggcat t                                                 21

<210> SEQ ID NO 23
<211> LENGTH: 25
<212> TYPE: DNA
<213> ORGANISM: Artificial Sequence
<220> FEATURE:
```

<223> OTHER INFORMATION: Synthetic oligonucleotide

<400> SEQUENCE: 23
ggtcatcctt gaagtttagt ttagc                                            25

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
caggacgcag gcgtttac                                                    18

<210> SEQ ID NO 25
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 25
ctgcataatc agctacggtg gtgcgg                                           26

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
ttcagcgtga ttcgcttgta g                                                21

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
ctggagtgcc caagagtc                                                    18

<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 28
cagacatgga agaaacacaa cccgcac                                          27

<210> SEQ ID NO 29
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 29
ctgctaagcc gcttctgtc                                                   19

```
<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
gctctggctg gtcttcagta tg                                              22

<210> SEQ ID NO 31
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 31
agcagctctg ccctcat                                                    17

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
ttgccgtatg gttggtttga ac                                              22

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
acagcctgct gtcacttgc                                                  19

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 34
tacgggcgtt tactgtcac                                                  19

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 35
accacatata ggtccttggg aac                                             23

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 36
ttctcaatgt gaccagcagt c                                              21

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
agggtcaacg ccacagcgaa tga                                            23

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
tcctgttctg tggaggatgt g                                              21
```

GENETICALLY MODIFIED MOUSE THAT EXPRESSES HUMANIZED PD1 AND PD-L1 PROTEINS

CROSS-REFERENCE TO RELATED APPLICATIONS

This application is a continuation of U.S. patent application Ser. No. 15/883,477, filed Jan. 30, 2018, which is a continuation of U.S. patent application Ser. No. 14/963,402, filed Dec. 9, 2015, now U.S. Pat. No. 9,913,461, which claims the benefit of U.S. Provisional Application No. 62/106,525, filed Jan. 22, 2015 and U.S. Provisional Application No. 62/089,549, filed Dec. 9, 2014, the entire contents of which are incorporated herein by reference.

INCORPORATION BY REFERENCE OF SEQUENCE LISTING

The Sequence Listing in the ASCII text file, named as 31971ZY_10133US03_SequenceListing.txt of 79 KB, created on Dec. 2, 2020, and submitted to the United States Patent and Trademark Office via EFS-Web, is incorporated herein by reference.

BACKGROUND

Despite significant advancements in the treatment of autoimmunity, cancer and infectious diseases, major challenges in the global healthcare industry remain. These major challenges are due, in part, to the ability of cells to modulate the immune response via cell surface polypeptides. Through some cell surface polypeptides cells and microorganisms have usurped signaling pathways to attenuate the monitoring mechanisms of the host immune system and inhibit immune responses to them, which leads to the development of disease phenotypes. Still, development of in vivo systems to optimally determine the therapeutic potential of new targeted therapies for autoimmunity, cancer and infectious diseases that are designed to modulate the immune responses to such disease pathologies and determine the molecular aspects of how such cells manipulate immune responses is lacking. Such in vivo systems provide a source for assays for assessing the therapeutic efficacy and development of candidate agents for the treatment of autoimmunity, cancer and infectious diseases in the future.

SUMMARY

The present invention encompasses the recognition that it is desirable to engineer non-human animals to permit improved in vivo systems for identifying and developing new therapeutics and, in some embodiments, therapeutic regimens, which can be used for the treatment of autoimmunity, inflammatory diseases and cancer. The present invention also encompasses the recognition that it is desirable to engineer non-human animals to permit improved in vivo systems for identifying and developing new therapeutics and, in some embodiments, therapeutic regimens, which can be used for the treatment of infectious diseases. Further, the present invention also encompasses the recognition that non-human animals having a humanized CD274 gene and/or otherwise expressing, containing, or producing a human or humanized PD-L1 polypeptide are desirable, for example for use in identifying and developing therapeutics that up-regulate anti-tumor and/or anti-microbial immunity. In some embodiments, non-human animals of the present invention provide improved in vivo systems for the identification and development of combination therapies that include targeting PD-L1 or indirectly targeting a PD-L1 binding partner (e.g., PD-1, B7-1).

In some embodiments, the present invention provides a non-human animal having a genome comprising a CD274 gene that includes genetic material from two different species (e.g., a human and a non-human). In some embodiments, the CD274 gene of a non-human animal as described herein encodes a PD-L1 polypeptide that contains human and non-human portions, wherein the human and non-human portions are linked together and form a functional PD-L1 polypeptide. In some embodiments, a non-human portion includes an endogenous portion. In some embodiments, a CD274 gene of a non-human animal as described herein encodes a PD-L1 polypeptide that contains an extracellular domain, in whole or in part, of a human PD-L1 polypeptide.

In some embodiments, the present invention provides a non-human animal that expresses a PD-L1 polypeptide, which PD-L1 polypeptide comprises a human portion and an endogenous portion. In some embodiments, a PD-L1 polypeptide of the present invention is translated in a cell of the non-human animal with a non-human signal peptide; in some certain embodiments, a rodent signal peptide.

In some embodiments, an endogenous portion comprises an intracellular portion of an endogenous PD-L1 polypeptide. In some embodiments, an endogenous portion further comprises a transmembrane portion of an endogenous PD-L1 polypeptide. In some embodiments, an endogenous portion has an amino acid sequence that is at least 50%, at least 60%, at least 70%, at least 80%, at least 90%, at least 95%, or at least 98% identical to a corresponding amino acid sequence of a mouse PD-L1 polypeptide that appears in FIG. 6. In some embodiments, an endogenous portion has an amino acid sequence that is substantially identical to a corresponding amino acid sequence of a mouse PD-L1 polypeptide that appears in FIG. 6. In some embodiments, an endogenous portion has an amino acid sequence that is identical to a corresponding amino acid sequence of a mouse PD-L1 polypeptide that appears in FIG. 6.

In some embodiments, a human portion comprises amino acids 19-238 of a human PD-L1 polypeptide. In some embodiments, a human portion comprises amino acids 19-277 of a human PD-L1 polypeptide. In some embodiments, a human portion comprises amino acids 19-131 of a human PD-L1 polypeptide. In some embodiments, a human portion comprises an amino acid sequence that is at least 50%, at least 60%, at least 70%, at least 80%, at least 90%, at least 95%, or at least 98% identical to a corresponding amino acid sequence of a human PD-L1 polypeptide that appears in FIG. 6. In some embodiments, a human portion comprises an amino acid sequence that is substantially identical to a corresponding amino acid sequence of a human PD-L1 polypeptide that appears in FIG. 6. In some embodiments, a human portion comprises an amino acid sequence that is identical to a corresponding amino acid sequence of a human PD-L1 polypeptide that appears in FIG. 6.

In some embodiments, a PD-L1 polypeptide of the present invention is encoded by a CD274 gene that includes an endogenous non-human CD274 sequence and a human CD274 sequence. In some certain embodiments, a CD274 gene comprises endogenous CD274 exons 1, 2, 6 and 7. In some certain embodiments, a CD274 gene further comprises an endogenous CD274 exon 5 in whole or in part. In some embodiments a CD274 gene that includes an endogenous non-human CD274 sequence and a human CD274 sequence is located at an endogenous CD274 locus.

In some embodiments, a CD274 gene of the present invention comprises a sequence that is at least 50%, at least 60%, at least 70%, at least 80%, at least 90%, at least 95%, or at least 98% identical to SEQ ID NO:12, SEQ ID NO:13 or SEQ ID NO:16. In some embodiments, a CD274 gene of the present invention comprises a sequence that is substantially identical to SEQ ID NO:12, SEQ ID NO:13 or SEQ ID NO:16. In some embodiments, a CD274 gene of the present invention comprises a sequence that is identical to SEQ ID NO:12, SEQ ID NO:13 or SEQ ID NO:16.

In some embodiments, a CD274 gene of the present invention comprises SEQ ID NO: 13, SEQ ID NO: 14, SEQ ID NO: 15 and SEQ ID NO: 16. In some embodiments, a CD274 gene of the present invention comprises SEQ ID NO: 13 and SEQ ID NO: 16. In some embodiments, a CD274 gene of the present invention comprises SEQ ID NO: 12 and SEQ ID NO: 13. In some embodiments, a CD274 gene of the present invention comprises SEQ ID NO: 12, SEQ ID NO: 13 and SEQ ID NO: 17. In some embodiments, a CD274 gene of the present invention comprises SEQ ID NO: 13, SEQ ID NO: 16 and SEQ ID NO: 17.

In some embodiments, the present invention provides a humanized CD274 locus. In some embodiments, a humanized CD274 locus is an endogenous non-human CD274 locus that has been genetically modified to include a human CD274 sequence. In some embodiments, the present invention provides a humanized CD274 locus comprising one or more exons of a non-human CD274 gene operably linked to one or more exons, in whole or in part, of a human CD274 gene. In some embodiments, a humanized CD274 locus further comprises 5' and 3' non-human CD274 untranslated regions (UTRs) flanking the one or more exons of a human CD274 gene. In some embodiments, a humanized CD274 locus is under the control of a rodent promoter; in some certain embodiments, an endogenous rodent promoter.

In some embodiments, a humanized CD274 locus comprises non-human CD274 exons 1, 2, 6 and 7 operably linked to human CD274 exons 3 and 4. In some embodiments, a humanized CD274 locus comprises non-human CD274 exons 1, 2, 6 and 7, human CD274 exons 3 and 4, and further comprises a CD274 exon 5, which CD274 exon 5 comprises a human portion and a non-human portion, and wherein said non-human and human exons are operably linked. In some embodiments, a human portion of a CD274 exon 5 includes nucleotides that encode amino acid residues that are a part of the extracellular domain of a human PD-L1 polypeptide. In some embodiments, a human portion of a CD274 exon 5 includes nucleotides that encode amino acid residues 229-238 of a human PD-L1 polypeptide. In some embodiments, a human portion of a CD274 exon 5 includes about 32 bp of a human CD274 exon 5. In some embodiments, a non-human portion of a CD274 exon 5 includes nucleotides that encode a transmembrane sequence. In some embodiments, a non-human portion of a CD274 exon 5 includes about 69 bp of a rodent CD274 exon 5. In some certain embodiments, a humanized CD274 locus comprises a CD274 exon 5 having a sequence set forth in SEQ ID NO:12. In some certain embodiments, a humanized CD274 locus comprises a CD274 exon 5 that encodes amino acids corresponding to L229-R238 of a human PD-L1 polypeptide and amino acids corresponding to T238-Q263 of a rodent PD-L1 polypeptide.

In some embodiments, the present invention provides a non-human animal comprising a CD274 gene that comprises an endogenous portion and a human portion, wherein the endogenous and human portions are operably linked to a non-human CD274 promoter. In some embodiments, a non-human CD274 promoter is a rodent CD274 promoter. In some certain embodiments, a rodent CD274 promoter is an endogenous rodent CD274 promoter.

In some embodiments, an endogenous portion comprises endogenous CD274 exons 1, 2, 6 and 7. In some embodiments, an endogenous portion further comprises an endogenous CD274 exon 5 in whole or in part. In some embodiments, endogenous CD274 exons 1, 2, 5 in whole or in part, 6 and 7 of the endogenous CD274 gene are at least 50%, at least 60%, at least 70%, at least 80%, at least 90%, at least 95%, or at least 98% identical to the corresponding exons 1, 2, 5 in whole or in part, 6 and 7 of a mouse Cd274 gene that appears in FIG. 6. In some embodiments, endogenous CD274 exons 1, 2, 5 in whole or in part, 6 and 7 of the endogenous CD274 gene are substantially identical to the corresponding exons 1, 2, 5 in whole or in part, 6 and 7 of a mouse Cd274 gene that appears in FIG. 6. In some embodiments, endogenous CD274 exons 1, 2, 5 in whole or in part, 6 and 7 of the endogenous CD274 gene are identical to the corresponding exons 1, 2, 5 in whole or in part, 6 and 7 of a mouse Cd274 gene that appears in FIG. 6.

In some embodiments, a human portion encodes amino acids 19-131, 19-227 or 19-238 of a human PD-L1 polypeptide.

In some embodiments, a human portion comprises exons 3 and 4 of a human CD274 gene. In some embodiments, a human portion further comprises a human CD274 exon 5 in whole or in part. In some embodiments, human CD274 exons 3, 4, and 5 in whole or in part, are at least 50%, at least 60%, at least 70%, at least 80%, at least 90%, at least 95%, or at least 98% identical to the corresponding exons 3, 4 and 5, in whole or in part, of a human CD274 gene that appears in FIG. 6. In some embodiments, human CD274 exons 3, 4, and 5 in whole or in part, are substantially identical to the corresponding exons 3, 4, and 5 in whole or in part, of a human CD274 gene that appears in FIG. 6. In some embodiments, human CD274 exons 3, 4, and 5 in whole or in part, are identical to the corresponding exons 3, 4, and 5 in whole or in part, of a human CD274 gene that appears in FIG. 6. In some embodiments, a human portion comprises a sequence that is codon-optimized for expression in a non-human animal; in some embodiments, expression in a rodent; in some certain embodiments, expression in a mouse or rat.

In some embodiments, a human portion includes a sequence that is at least 50%, at least 60%, at least 70%, at least 80%, at least 90%, or at least 95% identical to SEQ ID NO: 9, SEQ ID NO:10, SEQ ID NO:11 or SEQ ID NO:12. In some embodiments, a human portion includes a sequence that is substantially identical to SEQ ID NO: 9, SEQ ID NO:10, SEQ ID NO:11 or SEQ ID NO:12. In some embodiments, a human portion includes a sequence that is identical to SEQ ID NO: 9, SEQ ID NO:10, SEQ ID NO:11 or SEQ ID NO:12. In some embodiments, a human portion comprises SEQ ID NO: 9, SEQ ID NO:10, SEQ ID NO:11 or SEQ ID NO:12. In some embodiments, a human portion comprises a sequence that is identical to or substantially identical to SEQ ID NO: 7, SEQ ID NO:8 or SEQ ID NO:11. In some embodiments, a human portion comprises SEQ ID NO: 7, SEQ ID NO:8 or SEQ ID NO:11.

In some embodiments, a non-human animal of the present invention has a genome comprising a CD274 gene that comprises SEQ ID NO:8, SEQ ID NO:9, SEQ ID NO:10, SEQ ID NO:11, SEQ ID NO:12, SEQ ID NO:13, SEQ ID NO:16, SEQ ID NO:17 or a combination thereof.

In some embodiments, the present invention provides a PD-L1 polypeptide produced, expressed, or generated from a non-human animal as described herein. In some certain embodiments, a PD-L1 polypeptide produced, expressed, or generated from a non-human animal as described herein comprises an amino acid sequence that is at least 50%, at least 60%, at least 70%, at least 80%, at least 90%, at least 95%, or at least 98% identical to a humanized PD-L1 polypeptide that appears in FIG. 6. In some certain embodiments, a PD-L1 polypeptide produced, expressed, or generated from a non-human animal as described herein comprises an amino acid sequence that is substantially identical to a humanized PD-L1 polypeptide that appears in FIG. 6. In some certain embodiments, a PD-L1 polypeptide produced, expressed, or generated from a non-human animal as described herein comprises an amino acid sequence that is identical to a humanized PD-L1 polypeptide that appears in FIG. 6.

In some embodiments, the present invention provides an isolated cell or tissue from a non-human animal as described herein. In some embodiments, an isolated cell or tissue comprises a CD274 gene as described herein. In some embodiments, a cell is from a lymphoid lineage. In some embodiments, a cell is from a myeloid lineage. In some embodiments, a cell is selected from a B cell, dendritic cell, macrophage, monocyte, and a T cell. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a non-human embryonic stem cell whose genome comprises a CD274 gene as described herein. In some embodiments, a non-human embryonic stem cell is a rodent embryonic stem cell. In some certain embodiments, a rodent embryonic stem cell is a mouse embryonic stem cell and is from a 129 strain, C57BL strain, or a mixture thereof. In some certain embodiments, a rodent embryonic stem cell is a mouse embryonic stem cell and is a mixture of 129 and C57BL strains.

In some embodiments, a non-human embryonic stem cell of the present invention has a genome comprising a CD274 gene that comprises SEQ ID NO:13, SEQ ID NO:14, SEQ ID NO:15, SEQ ID NO:16 or a combination thereof.

In some embodiments, the present invention provides the use of a non-human embryonic stem cell as described herein to make a non-human animal. In some certain embodiments, a non-human embryonic stem cell is a mouse embryonic stem cell and is used to make a mouse comprising a CD274 gene as described herein. In some certain embodiments, a non-human embryonic stem cell is a rat embryonic stem cell and is used to make a rat comprising a CD274 gene as described herein.

In some embodiments, the present invention provides a non-human embryo comprising, made from, obtained from, or generated from a non-human embryonic stem cell comprising a CD274 gene as described herein. In some certain embodiments, a non-human embryo is a rodent embryo; in some embodiments, a mouse embryo; in some embodiments, a rat embryo.

In some embodiments, the present invention provides the use of a non-human embryo as described herein to make a non-human animal. In some certain embodiments, a non-human embryo is a mouse embryo and is used to make a mouse comprising a CD274 gene as described herein. In some certain embodiments, a non-human embryo is a rat embryo and is used to make a rat comprising a CD274 gene as described herein.

In some embodiments, the present invention provides a targeting vector or nucleic acid construct as described herein. In some embodiments, the present invention provides a targeting vector or nucleic acid construct that comprises a humanized CD274 gene as described herein. In some embodiments, the present invention provides a targeting vector (or nucleic acid construct) that comprises a CD274 gene that encodes a PD-L1 polypeptide that comprises a human extracellular domain in whole or in part; in some certain embodiments a PD-L1 polypeptide that comprises amino acids 19-131, 19-227 or 19-238 of a human PD-L1 polypeptide.

In some embodiments, a targeting vector or nucleic acid construct of the present invention comprises one or more exons, in whole or in part, of a non-human CD274 gene operably linked to one or more exons, in whole or in part, of a human CD274 gene. In some embodiments, a targeting vector or nucleic acid construct comprises 5' and 3' non-human CD274 untranslated regions (UTRs) flanking the one or more exons of a human CD274 gene. In some embodiments, a targeting vector or nucleic acid construct comprises one or more selection markers. In some embodiments, a targeting vector or nucleic acid construct comprises one or more site-specific recombination sites. In some embodiments, a targeting vector or nucleic acid construct comprises human CD274 exons 3 and 4. In some embodiments, a targeting vector or nucleic acid construct comprises human CD274 exons 3 and 4 and a human CD274 exon 5 in whole or in part.

In some embodiments, a targeting vector or nucleic acid construct comprises SEQ ID NO:7. In some certain embodiments, a targeting vector or nucleic acid construct comprises a sequence that is identical or substantially identical to any one of SEQ ID NO:9, SEQ ID NO:10 and SEQ ID NO:11.

In some embodiments, the present invention provides use of a targeting vector or nucleic acid construct as described herein to make a modified non-human embryonic stem cell. In some embodiments, the present invention provides use of a targeting vector or nucleic acid construct as described herein to make a modified non-human cell. In some embodiments, the present invention provides use of a targeting vector or nucleic acid construct as described herein to make a modified non-human embryo. In some embodiments, the present invention provides use of a targeting vector or nucleic acid construct as described herein to make a non-human animal.

In some embodiments, the present invention provides a method of making a non-human animal that expresses a PD-L1 polypeptide from an endogenous CD274 gene, wherein the PD-L1 polypeptide comprises a human sequence, the method comprising (a) inserting a genomic fragment into an endogenous CD274 gene in a non-human embryonic stem cell, said genomic fragment comprising a nucleotide sequence that encodes a human PD-L1 polypeptide in whole or in part; (b) obtaining the non-human embryonic stem cell generated in (a); and, (c) creating a non-human animal using the rodent embryonic stem cell of (b).

In some embodiments, a human sequence comprises amino acids 19-131, 19-227 or 19-238 of a human PD-L1 polypeptide.

In some embodiments, a nucleotide sequence comprises human CD274 exons 3 and 4. In some embodiments, a nucleotide sequence further comprises human CD274 exon 5 in whole or in part. In some embodiments, a nucleotide sequence comprises one or more selection markers. In some embodiments, a nucleotide sequence comprises one or more site-specific recombination sites.

In some embodiments, the present invention provides a method of making a non-human animal whose genome comprises a CD274 gene that encodes a PD-L polypeptide having a human portion and an endogenous portion, which portions are operably linked to a non-human CD274 promoter, the method comprising modifying the genome of a non-human animal so that it comprises a CD274 gene that encodes a PD-L1 polypeptide having a human portion and an endogenous portion, which portions are operably linked to a non-human CD274 promoter, thereby making said non-human animal. In some embodiments, a non-human CD274 promoter is a rodent CD274 promoter. In some certain embodiments, a rodent CD274 promoter is an endogenous rodent CD274 promoter.

In some embodiments, a human portion comprises amino acids 19-131, 19-227 or 19-238 of a human PD-L polypeptide.

In some embodiments, a CD274 gene is modified to include human CD274 exons 3 and 4. In some embodiments, a CD274 gene is modified to include human CD274 exons 3, 4, and 5 in whole or in part.

In some embodiments, modifying the genome of a non-human animal is performed in a non-human embryonic stem cell followed by generating a non-human animal with said non-human embryonic stem cell. In some certain embodiments, the non-human embryonic stem cell is a rodent embryonic stem cell; in some embodiments, a mouse embryonic stem cell; in some embodiments, a rat embryonic stem cell.

In some embodiments, the present invention provides a non-human animal obtainable by, generated from, or produced from a method as described herein.

In some embodiments, the present invention provides a method of reducing, preventing or eliminating tumor growth in a non-human animal, the method comprising the steps of administering a drug targeting human PD-L1 to a non-human animal whose genome comprises a CD274 gene that encodes a PD-L1 polypeptide having a human portion and an endogenous portion, which portions are operably linked to a non-human animal CD274 promoter; the administering being performed under conditions and for a time sufficient that tumor growth is reduced, prevented or eliminated in the non-human animal.

In some embodiments, the present invention provides a method of killing tumor cells in a non-human animal, the method comprising the steps of administering a drug targeting human PD-L1 to a non-human animal whose genome comprises a CD274 gene that encodes a PD-L1 polypeptide having a human portion and an endogenous portion, which portions are operably linked to a non-human animal CD274 promoter; the administering being performed under conditions and for a time sufficient that the drug mediates killing of the tumor cells in the non-human animal.

In some embodiments, the present invention provides a method of assessing the pharmacokinetic properties of a drug targeting human PD-L1, the method comprising the steps of administering a drug targeting human PD-L1 to a non-human animal whose genome comprises a CD274 gene that encodes a PD-L1 polypeptide having a human portion and an endogenous portion, which portions are operably linked to a non-human animal CD274 promoter; and performing an assay to determine one or more pharmacokinetic properties of the drug targeting human PD-L1.

In some embodiments, the present invention provides a method of assessing the efficacy of a drug targeting human PD-L1, the method comprising the steps of administering a drug targeting human PD-L1 to a non-human animal whose genome comprises a CD274 gene that encodes a PD-L1 polypeptide having a human portion and an endogenous portion, which portions are operably linked to a non-human animal CD274 promoter; and performing an assay to determine the efficacy of the drug targeting human PD-L1.

In various embodiments, a non-human animal as described herein is a rodent whose genome includes a CD274 gene that encodes a PD-L1 polypeptide having a human portion and an endogenous portion, which portions are operably linked to a rodent CD274 promoter. In various embodiments, a rodent CD274 promoter is an endogenous rodent CD274 promoter. In various embodiments, a human portion comprises amino acids 19-131, 19-227 or 19-238 of a human PD-L1 polypeptide.

In some embodiments, a drug targeting human PD-L1 is a PD-L1 antagonist. In some embodiments, a drug targeting human PD-L1 is a PD-L1 agonist. In some embodiments, a drug targeting human PD-L1 is an anti-PD-L1 antibody. In some embodiments, a drug targeting human PD-L1 is administered to a non-human animal intravenously, intraperitoneally, intramuscularly, or subcutaneously.

In some embodiments, the present invention provides a method for identification or validation of a drug or vaccine, the method comprising the steps of delivering a drug or vaccine to a non-human animal whose genome includes a CD274 gene as described herein, and monitoring one or more of the immune response to the drug or vaccine, the safety profile of the drug or vaccine, or the effect on a disease, disorder or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases. In some embodiments, the disease, disorder or condition is induced in the non-human animal. In some embodiments, the disease, disorder or condition induced in the non-human animal is associated with a disease, disorder or condition suffered by one or more human patients in need of treatment. In some certain embodiments, the drug is an antibody.

In some embodiments, the present invention provides use of a non-human animal as described herein in the development of a drug or vaccine for use in medicine, such as use as a medicament.

In some embodiments, the present invention provides use of a non-human animal as described herein in the manufacture of a medicament for the treatment of cancer or a neoplasm.

In some embodiments, the present invention provides use of a non-human animal as described herein in the manufacture of a medicament of the treatment of an infectious disease.

In some embodiments, the present invention provides use of a non-human animal as described herein in the manufacture of a medicament of the treatment of an inflammatory disease, disorder or condition.

In some embodiments, the present invention provides use of a non-human animal as described herein in the manufacture of a medicament of the treatment of an autoimmune disease, disorder or condition.

In various embodiments, a CD274 gene of the present invention includes a CD274 gene as described herein. In various embodiments, a CD274 gene of the present invention encodes a PD-L1 polypeptide having a human portion and an endogenous portion, which portions are operably linked to a rodent CD274 promoter. In various embodiments, a rodent promoter is an endogenous rodent promoter. In various embodiments, a human portion comprises human CD274 exons 3 and 4. In various embodiments, a human portion comprises human CD274 exons 3 and 4 and a human CD274 exon 5 in whole or in part.

In various embodiments, a PD-L1 polypeptide of the present invention includes a PD-L1 polypeptide as described herein.

In various embodiments, a non-human animal of the present invention does not detectably express a full-length endogenous non-human PD-L1 polypeptide. In various embodiments, a non-human animal of the present invention does not detectably express an extracellular portion of an endogenous PD-L1 polypeptide. In various embodiments, a non-human animal of the present invention does not detectably express an immunoglobulin V domain and, in some embodiments, an immunoglobulin C domain of an endogenous PD-L1 polypeptide.

In various embodiments, a non-human animal of the present invention is a rodent; in some embodiments, a mouse; in some embodiments, a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description of certain embodiments that follows. It should be understood, however, that the detailed description, while indicating certain embodiments of the present invention, is given by way of illustration only, not limitation. Various changes and modifications within the scope of the invention will become apparent to those skilled in the art from the detailed description.

BRIEF DESCRIPTION OF THE DRAWING

The Drawing included herein, which is composed of the following Figures, is for illustration purposes only and not for limitation.

FIG. 6 shows exemplary mouse, human and humanized CD274 and PD-L1 sequences, as well as exemplary human nucleic acid sequences for humanization of a non-human CD274 gene. For mRNA sequences, bold font indicates coding sequence and consecutive exons, where indicated, are separated by alternating underlined text; for humanized mRNA sequences, human sequences are contained within parentheses. For protein sequences, signal peptides are underlined, extracellular sequences are bold font, immunoglobulin V (IgV) domain sequences are within parentheses, and intracellular sequences are italicized; for humanized protein sequences, non-human sequences are indicated in regular font, human sequences are indicated in bold font. Humanization fragment A: human 4,494 bp-neomycin cassette-human 3,950 bp (SEQ ID NO:7); humanization fragment B: human 4,494 bp-loxP-human 3,950 bp (SEQ ID NO:8); humanization fragment C: human 4,494 bp fragment (SEQ ID NO:9); humanization fragment D: human 3,950 bp fragment (SEQ ID NO:10).

DEFINITIONS

Figure 1:
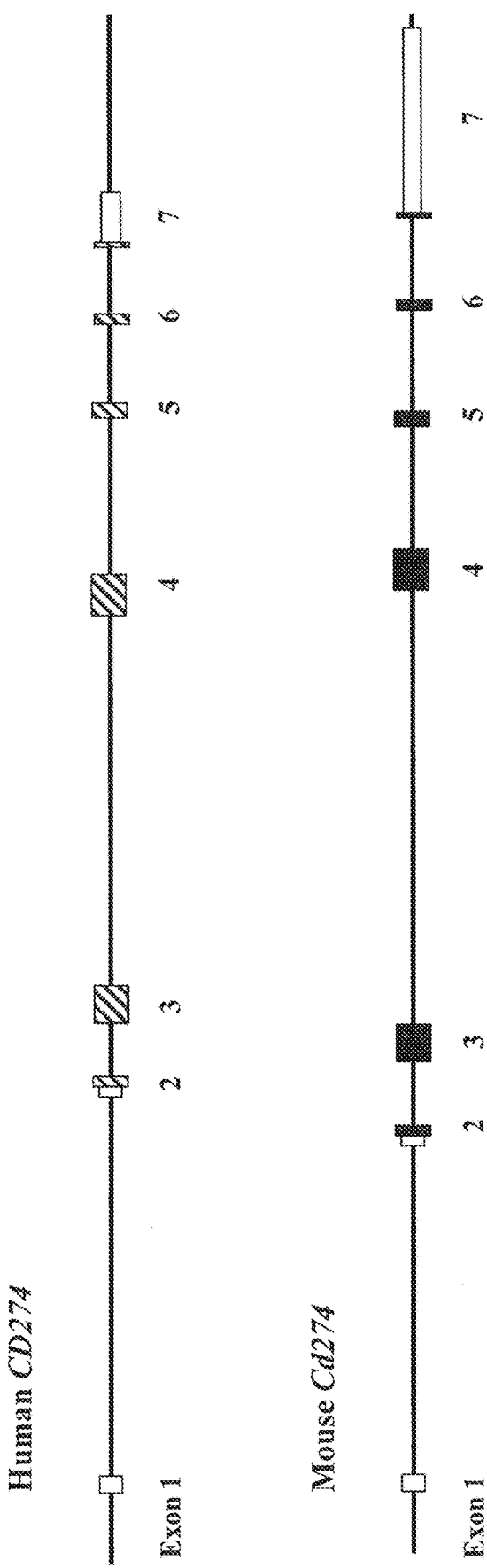
FIG. 1 shows a diagram, not to scale, of the genomic organization of a non-human (e.g., mouse) and human cluster of differentiation 274 (CD274) genes. Exons are numbered beneath each exon. Untranslated regions (UTRs) are indicated by open rectangles.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned herein are hereby incorporated by reference.

The term "approximately", as applied herein to one or more values of interest, includes a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active", as used herein, includes a characteristic of any agent that has activity in a biological system, in vitro or in vivo (e.g., in an organism). For instance, an agent that, when present in an organism, has a biological effect within that organism is considered to be biologically active. In particular embodiments, where a protein or polypeptide is biologically active, a portion of that protein or polypeptide that shares at least one biological activity of the protein or polypeptide is typically referred to as a "biologically active" portion.

The phrase "cluster of differentiation 274 protein", "CD274 protein", "B7-H1 protein", or "PD-L1 protein" as used herein, includes a transmembrane protein that belongs to the B7 family of cell-surface protein ligands and has extracellular immunoglobulin V (IgV) and immunoglobulin constant-like (IgC) domains, which are related to immunoglobulin variable and constant domains, and transmembrane and cytoplasmic (or intracellular) domains. PD-L1 is expressed in both lymphoid (e.g., B cell, T cell, dendritic cell, macrophages, monocytes, etc.) and non-lymphoid lineages (heart, lung, liver, pancreas, etc.) and is involved in interactions between membrane surface proteins such as, for example, Programmed cell death 1 (PD-1) to regulate immune function. Expression of PD-L1 is regulated by cytokines (e.g., interferon-γ) and has been reported to be up-regulated in many human cancers, which may allow such cancers to evade surveillance by the immune system. PD-L1 has been shown to be involved in several cellular processes such as, for example, intracellular infection, peripheral tolerance, T cell receptor signaling and T cell proliferation. Alternatively spliced CD274 isoforms have been identified between mouse and man. By way of illustration, nucleotide and amino acid sequences of murine and human CD274 genes are provided in FIG. 6. Persons of skill upon reading this disclosure will recognize that one or more endogenous CD274 genes in a genome (or all) can be replaced, modified, altered, deleted, disrupted, etc. by one or more heterologous CD274 genes (e.g., polymorphic variants, subtypes or mutants, genes from another species, humanized forms, etc.).

A "CD274-expressing cell", "B7-H1-expressing cell", or "PD-L1-expressing cell" as used herein, includes a cell that expresses a PD-L1 transmembrane polypeptide. In some embodiments, a PD-L1-expressing cell expresses PD-L1 transmembrane polypeptides on its surface. In some embodiments, PD-L1 polypeptides are expressed on the surface of the cell in an amount sufficient to mediate cell-to-cell interactions (e.g., through interactions with PD-1 receptor polypeptides). Exemplary PD-L-expressing cells include B cells, dendritic cells, macrophages, monocytes and T cells. PD-L-expressing cells modulate activation or inhibition of lymphoid cells to augment or attenuate immune responses. In some embodiments, non-human animals of the present invention demonstrate regulation of various cellular processes (as described herein) via humanized PD-L1 polypeptides expressed on the surface of one more cells of the non-human animal.

The term "comparable", as used herein, includes two or more agents, entities, situations, sets of conditions, etc. that may not be identical to one another but that are sufficiently similar to permit comparison between them so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative", as used herein to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, hereby incorporated by reference. In some embodiments, a substitution is a moderately conservative substitution wherein the substitution has a nonnegative value in the PAM250 log-likelihood matrix.

The term "control", as used herein, includes the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may refer to a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

The term "disruption", as used herein, includes the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The terms "determining", "measuring", "evaluating", "assessing", "assaying" and "analyzing" are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

The phrase "endogenous locus" or "endogenous gene", as used herein, includes a genetic locus found in a parent or reference organism prior to introduction of a disruption, deletion, replacement, alteration, or modification as described herein. In some embodiments, the endogenous locus has a sequence found in nature. In some embodiments, the endogenous locus is a wild type locus. In some embodiments, the reference organism is a wild-type organism. In some embodiments, the reference organism is an engineered organism. In some embodiments, the reference organism is a laboratory-bred organism (whether wild-type or engineered).

The phrase "endogenous promoter" includes a promoter that is naturally associated, e.g., in a wild-type organism, with an endogenous gene.

The term "heterologous", as used herein, includes an agent or entity from a different source. For example, when used in reference to a polypeptide, gene, or gene product present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell", as used herein, includes a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6® cell). In some embodiments, a host cell is or comprises an isolated cell. In some embodiments, a host cell is part of a tissue. In some embodiments, a host cell is part of an organism.

The term "humanized", is used herein in accordance with its art-understood meaning to refer to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion having an amino acid sequence as that of a human extracellular portion and the remaining sequence as that of a non-human (e.g., mouse) polypeptide. In some embodiments, a humanized gene comprises at least a portion of a DNA sequence of a human gene. In some embodiment, a humanized gene comprises an entire DNA sequence of a human gene. In some embodiments, a humanized protein comprises a sequence having a portion that appears in a human protein. In some embodiments, a humanized protein comprises an entire sequence of a human protein and is expressed from an endogenous locus of a non-human animal that corresponds to the homolog or ortholog of the human gene.

The term "identity", as used herein in connection with a comparison of sequences, includes identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

"Improve," "increase," "eliminate," or "reduce," as used herein or grammatical equivalents thereof, indicate values that are relative to a baseline measurement, such as a measurement in the same individual (or animal) prior to initiation of a treatment described herein, or a measurement in a control individual (or animal) or multiple control individuals (or animals) in the absence of the treatment described herein.

The term "isolated", as used herein, includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

The phrase "non-human anima", as used herein, includes any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid", as used herein, in its broadest sense, includes any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" includes individual nucleic acid residues (e.g., nucleotides and/or nucleosides); in some embodiments, "nucleic acid" includes an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" includes one or more exons. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

The phrase "operably linked", as used herein, includes a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence", as used herein, includes polynucleotide sequences, which are necessary to effect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence): sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes; typically, such control sequences include promoters and transcription termination sequence. The term "control sequences" is intended to include components whose presence is essential for expression and processing, and can also include additional components whose presence is advantageous, for example, leader sequences and fusion partner sequences.

The term "polypeptide", as used herein, includes any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

"Prevent" or "prevention", as used herein when used in connection with the occurrence of a disease, disorder, and/or condition, includes reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

The term "recombinant", as used herein, is intended to refer to polypeptides (e.g., PD-L1 polypeptides as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997 TIB Tech. 15:62-70; Hoogenboom H., and Chames P., 2000, Immunology Today 21:371-378; Azzazy H., and Highsmith W. E., 2002, Clin. Biochem. 35:425-445, Gavilondo J. V., and Larrick J. W., 2002, BioTechniques 29:128-145), antibodies isolated from an animal (e.g., a mouse) that is transgenic for human immunoglobulin genes (see e.g., Taylor, L. D., et al., 1992, Nucl. Acids Res. 20:6287-6295; Little M. et al., 2000, Immunology Today 21:364-370; Kellermann S. A. and Green L. L., 2002, Current Opinion in Biotechnology 13:593-597; Murphy, A. J., et al., 2014, Proc. Nat. Acad. Sci. U.S.A. 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide comprises sequences found in the genome of a source organism of interest (e.g., human, mouse, etc.). In some embodiments, a recombinant polypeptide comprises sequences that occur in nature separately from one another (i.e., from two or more different organisms, for example, human and non-human portions) in two different organisms (e.g., a human and a non-human organism). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a PD-L1 protein, and the DNA fragment encodes one or more human PD-L1 proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The term "reference" is used herein to describe a standard or control agent, animal, cohort, individual, population, sample, sequence or value against which an agent, animal, cohort, individual, population, sample, sequence or value of interest is compared. In some embodiments, a reference agent, animal, cohort, individual, population, sample, sequence or value is tested and/or determined substantially simultaneously with the testing or determination of the agent, animal, cohort, individual, population, sample, sequence or value of interest. In some embodiments, a reference agent, animal, cohort, individual, population, sample, sequence or value is a historical reference, optionally embodied in a tangible medium. In some embodiments, a reference may refer to a control. As used herein, a "reference" may include a "reference animal". A "reference animal" may have a modification as described herein, a modification that is different as described herein or no modification (i.e., a wild-type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

The term "substantially", as used herein, includes the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology", as used herein, includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "nonpolar" side chains. Substitution of one amino acid for another of the same type may often be considered a "homologous" substitution. Typical amino acid categorizations are summarized in Tables 1 and 2.

TABLE 1

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |

TABLE 1-continued

| Tyrosine | Tyr | Y | Polar | Neutral | −1.3 |
|---|---|---|---|---|---|
| Valine | Val | V | Nonpolar | Neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410: Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence, for example, noncontiguous residues brought together by the folded conformation of a polypeptide or a portion thereof. In some embodiments, the relevant stretch is at least 10, 15, 20, 25, 30, 35, 40, 45, 50, or more residues.

The phrase "substantial identity", as used herein, includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct", as used herein, includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein, in whole or in part, that has a similar function as a protein encoded by an endogenous sequence. In some embodiments, a targeting construct of the present invention further comprises a humanized gene of interest, in whole or in part, wherein the humanized gene of interest encodes a protein, in whole or in part, that has a similar function as a protein encoded by the endogenous sequence.

The term "variant", as used herein, includes an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a "variant" has 10, 9, 8, 7, 6, 5, 4, 3, 2, or 1 substituted residue as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, has its art-understood meaning that includes an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding a Programmed death-ligand 1 (PD-L1) polypeptide for determining the therapeutic efficacy of PD-L1 modulators (e.g., an anti-PD-L1 antibody) for the treatment of cancer, autoimmune diseases and infectious pathogens, as well as assays in immune cell responses and function. It is contemplated that such non-human animals provide an improvement in determining the therapeutic efficacy of PD-L1 modulators and their potential for PD-1:PD-L1 (or PD-L1:B7-1) blockade. Therefore, the present invention is particularly useful for the development of anti-PD-L1 and, in some embodiments, anti-PD-1 therapies, for the treatment of various cancers, autoimmune diseases as well as for augmenting immune responses to treat and/or ameliorate infectious etiologies. In particular, the present invention encompasses the humanization of a rodent CD274 gene resulting in expression of a humanized PD-L1 polypeptide on the surface of cells of the non-human animal. Such humanized PD-L1 non-human animals have the capacity to provide a source of human PD-L1$^+$ cells for determining the efficacy of anti-PD-L1 therapeutics to promote anti-tumor immune responses. Such humanized PD-L1 non-human animals also have the capacity to provide a source of human PD-LF cells for determining the efficacy of anti-PD-L1 therapeutics to ameliorate an autoimmune disease, disorder, or condition. Further, such humanized PD-L1 non-human animals provide an in vivo system for the screening and development of anti-PD-L1 therapies for the treatment of various cancers, autoimmune diseases and infectious diseases. In some embodiments, treatment efficacy may be demonstrated in non-human animals of the present invention by a decrease in or disappearance of signs and/or symptoms of the disease, disorder, or condition; in some embodiments, a decrease in or disappearance of some, but not all, signs and symptoms of the disease, disorder, or condition; in some embodiments, a decrease in or disappearance of all signs and symptoms of the disease, disorder, or condition, although the disease, disorder, or condition still may be in the body of the non-human animal. In various embodiments, the disease, disorder or condition is associated with a cancer. In various embodiments, the disease, disorder or condition is associated with an autoimmune disease, disorder or condition. In various embodiments, the disease, disorder or condition is associated with an infectious pathogen (e.g., a bacterium).

In some embodiments, non-human animals of the present invention demonstrate modulated immune responses via blockade of PD-1:PD-L1 signaling through the humanized PD-L1 polypeptide expressed on the surface of cells of the non-human animal. In some embodiments, humanized PD-L1 polypeptides have a sequence corresponding to the immunoglobulin V and C domains, in whole or in part, of a human PD-L1 polypeptide. In some embodiments, humanized PD-L1 polypeptides have a sequence corresponding to substantially all of the extracellular domain of a human PD-L1 polypeptide. In some embodiments, humanized PD-L1 polypeptides have a sequence corresponding to the cytoplasmic domain of a rodent PD-L1 polypeptide; in some embodiments, a sequence corresponding to the transmembrane and cytoplasmic domains of a rodent PD-L1 polypeptide. In some embodiments, humanized PD-L1 polypeptides have a sequence corresponding to amino acid residues 19-238 (or 19-227, or 19-131) of a human PD-L1 polypeptide. In some embodiments, non-human animals of the present invention comprise a CD274 gene that contains genetic material from the non-human animal and a heterologous species (e.g., a human). In some embodiments, non-human animals of the present invention comprise a humanized CD274 gene, wherein the humanized CD274 gene comprises exon 3, exon 4, and exon 5 in whole or in part, of a human CD274 gene. In some certain embodiments, non-human animals of the present invention comprise a humanized CD274 gene, wherein the humanized CD274 gene comprises about 4,494 bp of a human CD274 gene corresponding to exon 3 and about 4,160 bp of human genomic sequence 3' of exon 3. In some certain embodiments, non-human animals of the present invention comprise a humanized CD274 gene, wherein the humanized CD274 gene comprises about 3,950 bp of a human CD274 gene corresponding to about 1,253 bp of human genomic sequence 5' of exon 4, exon 4, intron 4 and the first 32 bp of exon 5 of a human CD274 gene. In some certain embodiments, non-human animals of the present invention comprise a humanized CD274 gene, wherein the humanized CD274 gene comprises about 4,494 bp and about 3,950 bp of a human CD274 gene juxtaposed with a site-specific recombination site (e.g., a loxP site), which 4,494 bp and 3,950 bp correspond to exon 3, exon 4 and the first 32 bp of exon 5 of a human CD274 gene. In some certain embodiments, non-human animals of the present invention comprise a humanized CD274 gene, wherein the humanized CD274 gene comprises about 8,444 bp of a human CD274 gene corresponding to exon 3, exon 4 and the first 32 bp of exon 5 of a human CD274 gene. In some embodiments, non-human animals (e.g., rodents such as mice or rats) of the present invention comprise a humanized CD274 gene, wherein the humanized CD274 gene comprises exon 3, exon 4 and a portion of exon 5 of a human CD274 gene, operably linked to exons 1, 2, a portion of exon 5, exon 6 and 7 of a non-human Cd274 gene (e.g., an endogenous non-human Cd274 gene); and in specific embodiments, the humanized CD274 gene encodes a humanized PD-L1 polypeptide that includes all or substantially all of the extracellular domain of a human PD-L1 polypeptide, and all or substantially all of the transmembrane and cytoplasmic domains of a non-human PD-L1 polypeptide. In some certain embodiments, non-human animals of the present invention comprise a humanized CD274 gene depicted in FIG. 2.

Various aspects of the invention are described in detail in the following sections. The use of sections is not meant to limit the invention. Each section can apply to any aspect of the invention. Throughout this application, the use of "or" means "and/or" unless stated otherwise.

Cluster of Differentiation 274 (CD274) Gene

CD274, which encodes a polypeptide termed Programmed cell death ligand 1 (PD-L1, also referred to as B7-H1), was discovered by searching the human expressed sequence tag (EST) database using B7 family members B7-1 and B7-2 (Dong, H. et al., 1999, Nature Med. 5(12):1365-1369; Freeman, G. J. et al., 2000, J. Exp. Med. 192(7):1027-1034). The CD274 gene consists of seven exons that each encode distinct portions of the PD-L1 polypeptide; exon 1: non-coding and contains 5'UTR; exon 2: signal sequence; exon 3: immunoglobulin V (IgV) domain; exon 4: immunoglobulin C (IgC) domain; exon 5: C-terminal part of the extracellular domain and transmembrane domain; exon 6: intracellular domain; and exon 7: ~6 amino acid residues of the intracellular domain and the 3'UTR. The PD-L1 polypeptide shares a common structural organization with other B7 family members (B7-1 and B7-2) despite a low percent sequence identity (20%). In contrast, the PD-L1 polypeptide sequences of mouse and man share about 70% sequence identity (Freeman, G. J. et al., supra). PD-L1 is strongly expressed in heart, skeletal muscle, placenta, and lung, weakly expressed in thymus, spleen, kidney and liver, and not expressed in brain, colon or small intestine (Dong, H. et al., supra). Further, PD-L1 is constitutively expressed on T cells, B cells, myeloid cells (e.g., dendritic cells, macrophages, mast cells, etc.) and keratinocytes in mouse, whereas expression in the same cells in humans has been reported after activation (e.g., reviewed in Keir, M. E., et al., 2008, Annu. Rev. Immunol. 26:677-704). Indeed, the CD274 promoter for both mouse and human genes has been reported to contain binding sites for interferon regulatory factor 1 (IRF-1), which has been suggested as being responsible for PD-L1 upregulation in human cancer cells (Lee, S. J. et al., 2006, FEBS Lett. 580(3):755-762). PD-L1 splice variants have been reported (see, e.g., below and He, X. H. et al., 2005, Acta Pharmacol Sin. 26(4):462-468), however, no causative relationship with any disease has yet been discovered. PD-L1 binds PD-1 exclusively without any interactions with other proteins structurally similar to PD-1 (CTLA4, CD28, ICOS; see Dong. Dong, H. et al. and Freeman, G. J. et al., supra). PD-L1 engagement with PD-1 leads to a variety of stimulatory or inhibitory functions in immune cells, some of which include cell proliferation, cytokine production, and T cell receptor and B cell receptor signaling. PD-L1 (as well as PD-L2) has also been suggested to be involved in bidirectional signaling (e.g., see Dong, H. et al., 2003, J. Clin. Invest. 111:363-370; Kuipers, H. et al., 2006, Eur. J. Immunol. 36:2472-2782). Interestingly, PD-L1 has been shown to bind B7-1 (CD80), a ligand for CD28, although no interaction with CD28 itself has been reported (Butte, M. J. et al., 2007, Immunity 27:111-122). This unique interaction with B7-1 has been particularly important for its implications in the regulation of T cell responses and tolerance. Indeed, due to multiple functional outcomes provided by its costimulatory and coinhibitory functions, PD-L1 has attracted much interest as a potential target for treatment of autoimmune and inflammatory diseases as well as the treatment of cancer. In fact, anti-PD-L1 therapy is currently being tested in human clinical trials (see e.g., Pedoeem, A. et al., 2014, Clin. Immunol. 153:145-152; and Philips, G. K. and Atkins, M., 2014, Intern. Immunol. 8 pages).

A more thorough and detailed understanding of PD-L1-mediated functions across many of the cell types in which it is expressed (e.g., non-lymphoid cells) and the unique interactions with other B7 family members is needed to develop practical targeted therapies for treatment of cancer and autoimmunity in the future.

CD274 and PD-L1 (B7-H) Sequences

Exemplary murine, human and humanized CD274 and PD-L1 sequences are set forth in FIG. 6. Exemplary human nucleic acid sequences for humanization of a non-human CD274 gene are also set forth in FIG. 6. For mRNA sequences, bold font indicates coding sequence and consecutive exons, where indicated, are separated by alternating underlined text; for humanized mRNA sequences, human sequences are contained within parentheses. For protein sequences, signal peptides are underlined, extracellular sequences are bold font, immunoglobulin V (IgV) domain sequences are within parentheses, and intracellular sequences are italicized; for humanized protein sequences, non-human sequences are indicated in regular font, human sequences are indicated in bold font.

CD274 transcript variants are known in the art. One transcript variant lacks an in-frame exon in the 5' coding region as compared to the canonical sequence (see FIG. 6) and results in a deletion of residues 17-130 (i.e., the IgV domain plus ~5 amino acid residues). The mRNA and protein sequences of this variant can be found at Genbank accession numbers NM_001267706.1 and NP_001254635.1, respectively, hereby incorporated by reference. Another variant encodes a soluble protein having a K178D substitution and a deletion of residues 179-290. The mRNA and protein sequences of this variant can be found at Genbank accession numbers XM_006716759.1 and XP_006716822.1, respectively, hereby incorporated by reference. A third variant has been described (NR_052005.1) to lack an alternate internal segment as compared to the canonical sequence and, therefore, is represented as a non-coding variant because the use of the 5'-most supported translation start codon renders the transcript a candidate for nonsense-mediated mRNA decay (NMD). Other isoforms are described in WO 2014/197369, which is hereby incorporated by reference.

Humanized CD274 Non-Human Animals

Non-human animals are provided that express humanized PD-L1 polypeptides on the surface of cells of the non-human animals resulting from a genetic modification of an endogenous locus (e.g., a CD274 locus) of the non-human animal that encodes a PD-L1 polypeptide. Suitable examples described herein include rodents, in some embodiments, mice.

A humanized CD274 gene, in some embodiments, comprises genetic material from a heterologous species (e.g., humans), wherein the humanized CD274 gene encodes a PD-L1 polypeptide that comprises the encoded portion of the genetic material from the heterologous species. In some embodiments, a humanized CD274 gene of the present invention comprises genomic DNA of a heterologous species that encodes the extracellular portion of a PD-L1 polypeptide that is expressed on the plasma membrane of a cell. Non-human animals, embryos, cells and targeting constructs for making non-human animals, non-human embryos, and cells containing said humanized CD274 gene are also provided.

In some embodiments, an endogenous CD274 gene is deleted. In some embodiments, an endogenous CD274 gene is altered, wherein a portion of the endogenous CD274 gene is replaced with a heterologous sequence (e.g., a human CD274 sequence, in whole or in part). In some embodiments, all or substantially all of an endogenous CD274 gene is replaced with a heterologous gene (e.g., a human CD274 gene). In some embodiments, a portion of a heterologous CD274 gene is inserted into an endogenous non-human CD274 gene at an endogenous CD274 locus. In some embodiments, the heterologous gene is a human gene. In some embodiments, the modification or humanization is made to one of the two copies of the endogenous CD274 gene, giving rise to a non-human animal that is heterozygous with respect to the humanized CD274 gene. In other embodiments, a non-human animal is provided that is homozygous for a humanized CD274 gene.

In various aspects, a non-human animal contains a human CD274 gene, in whole or in part, at an endogenous non-human CD274 locus. In some embodiments, a non-human animal contains a human CD274 gene, at a location outside of an endogenous non-human CD274 locus. Thus, such non-human animals can be described as having a heterologous CD274 gene. The replaced, inserted, modified or altered CD274 gene at the endogenous CD274 locus (or outside the endogenous CD274 locus) or a polypeptide expressed from such gene (or expressed from elsewhere in the genome of the non-human animal) can be detected using a variety of methods including, for example, PCR, Western blot, Southern blot, restriction fragment length polymorphism (RFLP), or a gain or loss of allele assay. In some embodiments, the non-human animal is heterozygous with respect to the humanized CD274 gene.

In various embodiments, a humanized CD274 gene according to the present invention includes a CD274 gene that has a third exon having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a third exon that appears in a human CD274 mRNA sequence of FIG. 6.

In various embodiments, a humanized CD274 gene according to the present invention includes a CD274 gene that has a third exon having a sequence that is substantially identical to a third exon that appears in a human CD274 mRNA sequence of FIG. 6.

In various embodiments, a humanized CD274 gene according to the present invention includes a CD274 gene that has a third exon having a sequence that is identical to a third exon that appears in a human CD274 mRNA sequence of FIG. 6.

In various embodiments, a humanized CD274 gene according to the present invention includes a CD274 gene that has a fourth exon having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a fourth exon that appears in a human CD274 mRNA sequence of FIG. 6.

In various embodiments, a humanized CD274 gene according to the present invention includes a CD274 gene that has a fourth exon having a sequence that is substantially identical to a fourth exon that appears in a human CD274 mRNA sequence of FIG. 6.

In various embodiments, a humanized CD274 gene according to the present invention includes a CD274 gene that has a fourth exon having a sequence that is identical to a fourth exon that appears in a human CD274 mRNA sequence of FIG. 6.

In various embodiments, a humanized CD274 gene according to the present invention includes a CD274 gene that has a fifth exon having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a fifth exon that appears in a humanized CD274 mRNA sequence of FIG. 6.

In various embodiments, a humanized CD274 gene according to the present invention includes a CD274 gene that has a fifth exon having a sequence that is substantially identical to a fifth exon that appears in a humanized CD274 mRNA sequence of FIG. 6.

In various embodiments, a humanized CD274 gene according to the present invention includes a CD274 gene that has a fifth exon having a sequence that is identical to a fifth exon that appears in a humanized CD274 mRNA sequence of FIG. 6.

In various embodiments, a humanized CD274 gene according to the present invention includes a CD274 gene that has a third, fourth and fifth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a third, fourth and fifth exon that appear in a humanized CD274 mRNA sequence of FIG. 6.

In various embodiments, a humanized CD274 gene according to the present invention includes a CD274 gene that has a third, fourth and fifth exon each having a sequence that is substantially identical to a third, fourth and fifth exon that appear in a humanized CD274 mRNA sequence of FIG. 6.

In various embodiments, a humanized CD274 gene according to the present invention includes a CD274 gene that has a third, fourth and fifth exon each having a sequence that is identical to a third, fourth and fifth exon that appear in a humanized CD274 mRNA sequence of FIG. 6.

In various embodiments, a humanized CD274 gene according to the present invention includes a CD274 gene that has a first, second, sixth and seventh exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a first, second, sixth and seventh exon that appear in a mouse Cd274 mRNA sequence of FIG. 6.

In various embodiments, a humanized CD274 gene according to the present invention includes a CD274 gene that has a first, second, sixth and seventh exon each having a sequence that is substantially identical to a first, second, sixth and seventh exon that appear in a mouse Cd274 mRNA sequence of FIG. 6.

In various embodiments, a humanized CD274 gene according to the present invention includes a CD274 gene that has a first, second, sixth and seventh exon each having a sequence that is identical to a first, second, sixth and seventh exon that appear in a mouse Cd274 mRNA sequence of FIG. 6.

In various embodiments, a humanized CD274 gene according to the present invention includes a CD274 gene that comprises a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:12.

In various embodiments, a humanized CD274 gene according to the present invention includes a CD274 gene that comprises a sequence that is substantially identical to SEQ ID NO:12.

In various embodiments, a humanized CD274 gene according to the present invention includes a CD274 gene that comprises a sequence that is identical to SEQ ID NO:12.

In various embodiments, a humanized CD274 gene according to the present invention includes a CD274 gene that comprises a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:13 or SEQ ID NO:16.

In various embodiments, a humanized CD274 gene according to the present invention includes a CD274 gene that comprises a sequence that is substantially identical to SEQ ID NO:13 or SEQ ID NO:16.

In various embodiments, a humanized CD274 gene according to the present invention includes a CD274 gene that comprises a sequence that is identical to SEQ ID NO:13 or SEQ ID NO:16.

In various embodiments, a humanized CD274 gene according to the present invention includes a CD274 gene that comprises a first sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:13 and a second sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:16.

In various embodiments, a humanized CD274 gene according to the present invention includes a CD274 gene that comprises a first sequence that is substantially identical to SEQ ID NO:13 and a second sequence that is substantially identical to SEQ ID NO:16.

In various embodiments, a humanized CD274 gene according to the present invention includes a CD274 gene that comprises a first sequence that is identical to SEQ ID NO:13 and a second sequence that is identical to SEQ ID NO:16.

In various embodiments, a humanized CD274 gene according to the present invention comprises SEQ ID NO: 13, SEQ ID NO:16 and a site-specific recombinase recognition site, wherein said site-specific recombinase recognition site is located within an intron of said humanized CD274 gene.

In various embodiments, a humanized CD274 gene according to the present invention comprises SEQ ID NO: 13, SEQ ID NO:16 and a loxP site, wherein said loxP site is located within an intron of said humanized CD274 gene.

In various embodiments, a humanized CD274 gene according to the present invention includes a CD274 gene that comprises an intron between a CD274 exon 3 and a CD274 exon 4, wherein said intron comprises a sequence that is substantially identical to SEQ ID NO:17.

In various embodiments, a humanized CD274 gene according to the present invention includes a CD274 gene that comprises an intron between a CD274 exon 3 and a CD274 exon 4, wherein said intron comprises a sequence that is identical to SEQ ID NO:17.

In various embodiments, a humanized CD274 gene according to the present invention includes a CD274 gene that comprises SEQ ID NO: 12, SEQ ID NO:13, SEQ ID NO:16 and SEQ ID NO:17.

In various embodiments, a humanized CD274 gene according to the present invention includes a CD274 gene that comprises SEQ ID NO: 12, SEQ ID NO:13, SEQ ID NO:14, SEQ ID NO:15 and SEQ ID NO:16.

In various embodiments, a humanized CD274 gene according to the present invention includes a CD274 gene that has a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to a nucleotide coding sequence that appears in a humanized CD274 nucleotide coding sequence of FIG. 6.

In various embodiments, a humanized CD274 gene according to the present invention includes a CD274 gene that has a nucleotide coding sequence (e.g., a cDNA sequence) that is substantially identical to a nucleotide coding sequence that appears in a humanized CD274 nucleotide coding sequence of FIG. 6.

In various embodiments, a humanized CD274 gene according to the present invention includes a CD274 gene that has a nucleotide coding sequence (e.g., a cDNA sequence) that is identical to a nucleotide coding sequence that appears in a humanized CD274 nucleotide coding sequence of FIG. 6.

In various embodiments, a humanized CD274 mRNA sequence according to the present invention comprises a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a humanized CD274 mRNA sequence of FIG. 6.

In various embodiments, a humanized CD274 mRNA sequence according to the present invention comprises a sequence that is substantially identical to a humanized CD274 mRNA sequence of FIG. 6.

In various embodiments, a humanized CD274 mRNA sequence according to the present invention comprises a sequence that is identical to a humanized CD274 mRNA sequence of FIG. 6.

In various embodiments, a humanized CD274 gene according to the present invention encodes a PD-L1 polypeptide having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a PD-L1 polypeptide sequence of FIG. 6.

In various embodiments, a humanized CD274 gene according to the present invention encodes a PD-L1 polypeptide having an amino acid sequence that is substantially identical to a PD-L1 polypeptide sequence of FIG. 6.

In various embodiments, a humanized CD274 gene according to the present invention encodes a PD-L1 polypeptide having an amino acid sequence that is identical to a PD-L1 polypeptide sequence of FIG. 6.

In various embodiments, a PD-L1 polypeptide produced by a non-human animal of the present invention has an extracellular portion having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human PD-L1 polypeptide that appears in FIG. 6.

In various embodiments, a PD-L1 polypeptide produced by a non-human animal of the present invention has an extracellular portion having an amino acid sequence that is substantially identical to an extracellular portion of a human PD-L1 polypeptide that appears in FIG. 6.

In various embodiments, a PD-L1 polypeptide produced by a non-human animal of the present invention has an extracellular portion having an amino acid sequence that is identical to an extracellular portion of a human PD-L1 polypeptide that appears in FIG. 6.

In various embodiments, a PD-L1 polypeptide produced by a non-human animal of the present invention comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 19-131 that appears in a human or humanized PD-L1 polypeptide of FIG. 6.

In various embodiments, a PD-L1 polypeptide produced by a non-human animal of the present invention comprises an amino acid sequence that is substantially identical to amino acid residues 19-131 that appears in a human or humanized PD-L1 polypeptide of FIG. 6.

In various embodiments, a PD-L1 polypeptide produced by a non-human animal of the present invention comprises an amino acid sequence that is identical to amino acid residues 19-131 that appears in a human or humanized PD-L1 polypeptide of FIG. 6.

In various embodiments, a PD-L1 polypeptide produced by a non-human animal of the present invention comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 19-227 that appears in a human or humanized PD-L1 polypeptide of FIG. 6.

In various embodiments, a PD-L1 polypeptide produced by a non-human animal of the present invention comprises an amino acid sequence that is substantially identical to amino acid residues 19-227 that appears in a human or humanized PD-L1 polypeptide of FIG. 6.

In various embodiments, a PD-L1 polypeptide produced by a non-human animal of the present invention comprises an amino acid sequence that is identical to amino acid residues 19-227 that appears in a human or humanized PD-L1 polypeptide of FIG. 6.

In various embodiments, a PD-L1 polypeptide produced by a non-human animal of the present invention comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 19-238 that appears in a human or humanized PD-L1 polypeptide of FIG. 6.

In various embodiments, a PD-L1 polypeptide produced by a non-human animal of the present invention comprises an amino acid sequence that is substantially identical to amino acid residues 19-238 that appears in a human or humanized PD-L1 polypeptide of FIG. 6.

In various embodiments, a PD-L1 polypeptide produced by a non-human animal of the present invention comprises an amino acid sequence that is identical to amino acid residues 19-238 that appears in a human or humanized PD-L1 polypeptide of FIG. 6.

In various embodiments, a PD-L1 polypeptide produced by a non-human animal of the present invention has an immunoglobulin V (IgV) domain having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an IgV domain of a human PD-L1 polypeptide that appears in FIG. 6.

In various embodiments, a PD-L1 polypeptide produced by a non-human animal of the present invention has an immunoglobulin V (IgV) domain having an amino acid sequence that is substantially identical to an IgV domain of a human PD-L1 polypeptide that appears in FIG. 6.

In various embodiments, a PD-L1 polypeptide produced by a non-human animal of the present invention has an immunoglobulin V (IgV) domain having an amino acid sequence that is identical to an IgV domain of a human PD-L polypeptide that appears in FIG. 6.

In various embodiments, a PD-L1 polypeptide produced by a non-human animal of the present invention has an immunoglobulin V (IgV) domain and an immunoglobulin C (IgC) domain each having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an IgV domain and an IgC domain of a human PD-L polypeptide that appears in FIG. 6.

In various embodiments, a PD-L1 polypeptide produced by a non-human animal of the present invention has an immunoglobulin V (IgV) domain and an immunoglobulin C (IgC) domain each having an amino acid sequence that is substantially identical to an IgV domain and an IgC domain of a human PD-L1 polypeptide that appears in FIG. 6.

In various embodiments, a PD-L1 polypeptide produced by a non-human animal of the present invention has an immunoglobulin V (IgV) domain and an immunoglobulin C (IgC) domain each having an amino acid sequence that is identical to an IgV domain and an IgC domain of a human PD-L1 polypeptide that appears in FIG. 6.

In various embodiments, a PD-L1 polypeptide produced by a non-human animal of the present invention has a transmembrane domain and an intracellular domain each having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a transmembrane domain and an intracellular domain of a mouse PD-L1 polypeptide that appears in FIG. 6.

In various embodiments, a PD-L1 polypeptide produced by a non-human animal of the present invention has a transmembrane domain and an intracellular domain each having an amino acid sequence that is substantially identical to a transmembrane domain and an intracellular domain of a mouse PD-L1 polypeptide that appears in FIG. 6.

In various embodiments, a PD-L1 polypeptide produced by a non-human animal of the present invention has a transmembrane domain and an intracellular domain each having an amino acid sequence that is identical to a transmembrane domain and an intracellular domain of a mouse PD-L1 polypeptide that appears in FIG. 6.

In various embodiments, a PD-L1 polypeptide produced by a non-human animal of the present invention has an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized PD-L1 polypeptide that appears in FIG. 6.

In various embodiments, a PD-L1 polypeptide produced by a non-human animal of the present invention has an amino acid sequence that is substantially identical to an amino acid sequence of a humanized PD-L1 polypeptide that appears in FIG. 6.

In various embodiments, a PD-L1 polypeptide produced by a non-human animal of the present invention has an amino acid sequence that is identical to an amino acid sequence of a humanized PD-L1 polypeptide that appears in FIG. 6.

Compositions and methods for making non-human animals that express a humanized PD-L1 polypeptide, including specific polymorphic forms, allelic variants (e.g., single amino acid differences) or alternatively spliced isoforms, are provided, including compositions and methods for making non-human animals that express such polypeptides from a human promoter and a human regulatory sequence(s). In some embodiments, compositions and methods for making non-human animals that express such polypeptides from an endogenous promoter and an endogenous regulatory sequence(s) are also provided; in some embodiments, from an endogenous rodent promoter and an endogenous rodent regulatory sequence(s). The methods include inserting the genetic material encoding a human PD-L1 polypeptide (e.g., a human CD274 DNA sequence) in whole or in part at a precise location in the genome of a non-human animal that corresponds to an endogenous CD274 gene thereby creating a humanized CD274 gene that expresses a PD-L1 polypeptide that is human in whole or in part. Alternatively, insertion of the genetic material encoding a human PD-L1 polypeptide in whole or in part may be made at a random location in the genome of a non-human animal, i.e., outside of an endogenous CD274 gene. In some embodiments, the methods include inserting genomic DNA corresponding to exons 3-5 (or exons 3, 4 and a portion of exon 5) of a human CD274 gene into an endogenous CD274 gene of the non-human animal thereby creating a humanized gene that encodes a PD-L1 polypeptide that contains a human portion containing amino acids encoded by the inserted exons. In some embodiments, the methods include randomly inserting genomic DNA corresponding to a full-length (or cDNA) human CD274 gene into the genome of the non-human animal thereby creating a human CD274 transgene that encodes a full-length human PD-L1 polypeptide.

Where appropriate, the coding region of the genetic material or polynucleotide sequence(s) encoding a human PD-L1 polypeptide in whole or in part may be modified to include codons that are optimized for expression in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a human PD-L1 polypeptide, in whole or in part, may include an altered sequence to optimize codon usage for a particular cell type (e.g., a rodent cell). For example, the codons of the genomic DNA corresponding to exons 3-5 (or exons 3, 4 and a portion of exon 5) of a human CD274 gene to be inserted into an endogenous CD274 gene of a non-human animal (e.g., a rodent) may be optimized for expression in a cell of the non-human animal. Such a sequence may be described as a codon-optimized sequence.

A humanized CD274 gene approach employs a relatively minimal modification of the endogenous gene and results in natural CD274-mediated (i.e., PD-L1-mediated) signal transduction in the non-human animal, because, e.g., the genomic sequence of the CD274 gene is modified in a single fragment and therefore retains normal functionality by including necessary regulatory sequences and, in some embodiments, intron sequences. Thus, in such embodiments, the CD274 gene modification does not affect other surrounding genes or other endogenous CD274-interacting genes (e.g., Pdcd1, etc.). Further, in various embodiments, the modification does not affect the assembly of a functional PD-L1 transmembrane polypeptide on the plasma membrane and maintains normal effector functions via binding and subsequent signal transduction through the cytoplasmic portion of the polypeptide which is unaffected by the modification.

A schematic illustration (not to scale) of the genomic organization of a rodent (e.g., mouse) Cd274 gene and a human CD274 gene is set forth in FIG. 1. Exemplary constructs for humanizing an endogenous rodent (e.g., mouse) Cd274 gene using a genomic fragment containing exons 3, 4 and a portion of exon 5 of a human CD274 gene are set forth in FIG. 2. As illustrated, genomic DNA containing exons 3, 4 and a portion of exon 5 of a human CD274 gene is inserted into an endogenous rodent (e.g., mouse) Cd274 gene locus by a targeting construct. This genomic DNA includes the portion of the gene that encodes an extracellular portion (e.g., amino acid residues 19-238) of a human PD-L1 polypeptide. If so desired, genomic DNA containing exons 3 and 4 of a human CD274 gene may be inserted into an endogenous rodent (e.g., mouse) Cd274 gene locus by a targeting construct so to include the portion of the gene that encodes the immunoglobulin V and C domains (e.g., amino acid residues 19-227) of a human PD-L1 polypeptide. Alternatively, genomic DNA containing only exon 3 of a human CD274 gene may be inserted into an endogenous rodent (e.g., mouse) Cd274 gene locus by a targeting construct so to include only the portion of the gene that encodes the immunoglobulin V domain (e.g., amino acid residues 19-131) of a human PD-L1 polypeptide. Persons of skill upon reading this disclosure will understand that various amounts of genetic material of a human CD274 gene may be inserted into the genome of a non-human animal following the methodology described herein depending on the encoded PD-L1 polypeptide that is desired.

Figure 2:
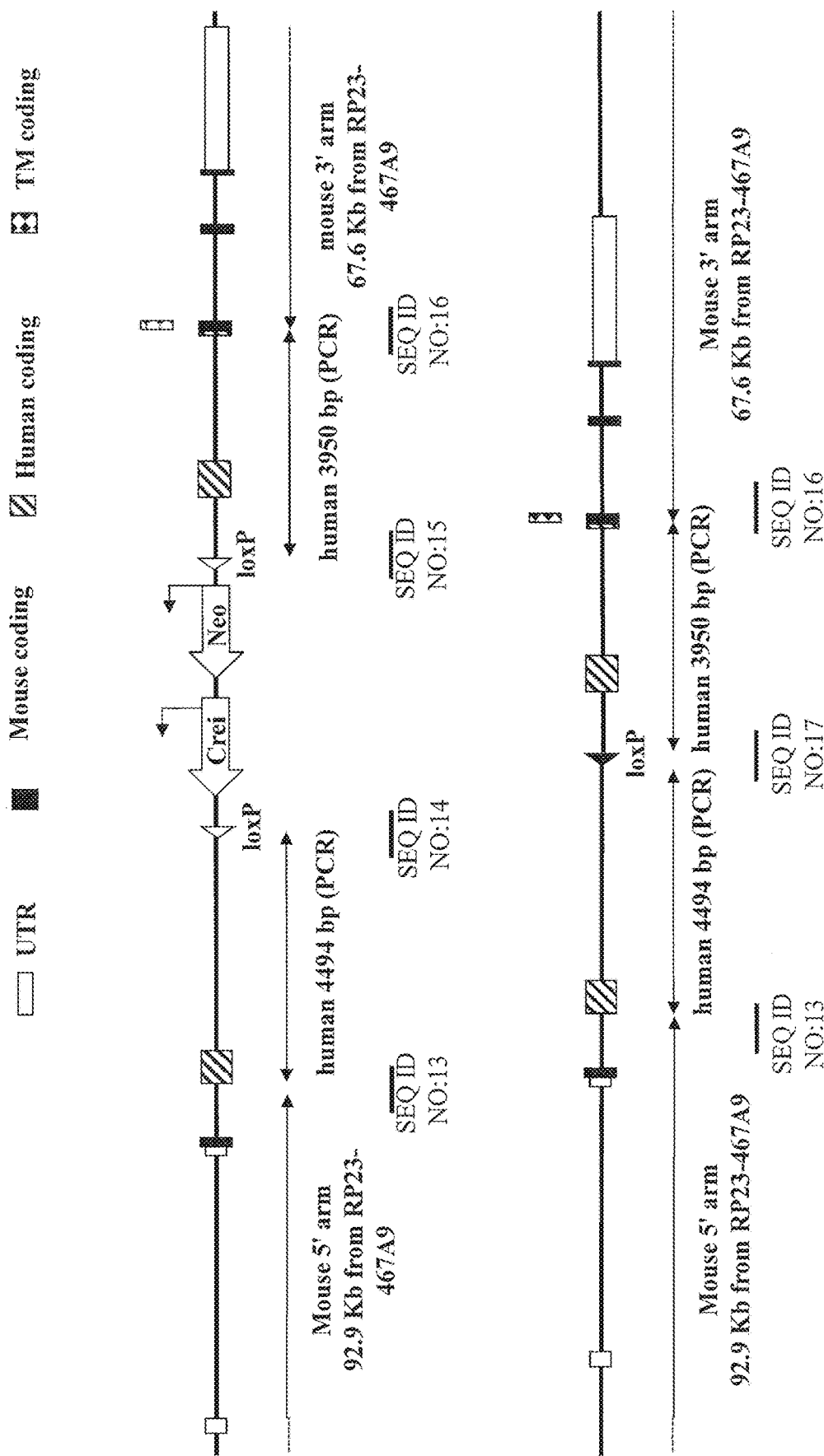
FIG. 2 shows an illustration, not to scale, of an exemplary constructs used in humanization of a non-human cluster of differentiation 274 (CD274) gene. Top diagram represents a humanized targeting vector with a neomycin cassette, while the bottom diagram represents a humanized targeting vector with the cassette deleted. Selected nucleotide junction locations are marked with a line below each junction accompanied by the corresponding SEQ ID NOs. Exemplary humanization fragments are set forth in FIG. 6 and are illustrated as follows: humanization fragment A: human 4,494 bp-neomycin cassette-human 3,950 bp (SEQ ID NO:7); humanization fragment B: human 4,494 bp-loxP-human 3,950 bp (SEQ ID NO:8); humanization fragment C: human 4,494 bp fragment (SEQ ID NO:9); humanization fragment D: human 3,950 bp fragment (SEQ ID NO:10).

A non-human animal (e.g., a mouse) having a humanized CD274 gene at the endogenous CD274 locus can be made by any method known in the art. For example, a targeting vector can be made that introduces a human CD274 gene in whole or in part with a selectable marker gene. FIG. 2 illustrates an endogenous Cd274 locus of a mouse genome comprising an insertion of exons 3, 4 and a portion of exon 5 (about 32 bp) of a human CD274 gene. As illustrated, the targeting construct contains a 5' homology arm containing sequence upstream of exon 3 of an endogenous murine Cd274 gene (~92.9 Kb), followed by a genomic DNA fragment containing exon 3 of a human CD274 gene (~4494 bp), a drug selection cassette (e.g., a neomycin resistance gene flanked on both sides by loxP sequences; ~5 Kb) in opposite transcriptional direction relative to the endogenous murine Cd274 gene, a genomic DNA fragment containing exons 4 and a portion of exon 5 of a human CD274 gene (~3950 bp), and a 3' homology arm containing a portion of exon 5 of an endogenous murine Cd274 gene and genomic sequence downstream including exons 6 and 7 (~67.6 Kb). The targeting construct contains a self-deleting drug selection cassette (e.g., a neomycin resistance gene flanked by loxP sequences; see U.S. Pat. Nos. 8,697,851, 8,518,392 and 8,354,389, all of which are hereby incorporated by reference). Upon homologous recombination, exons 3, 4 and a portion of exon 5 of an endogenous murine Cd274 gene are replaced by the sequence contained in the targeting vector (i.e., exons 3, 4 and a portion of exon 5 of a human CD274 gene) resulting in a deletion of about 8,964 bp. A humanized CD274 gene is created resulting in a cell or non-human animal that expresses a humanized PD-L1 polypeptide that contains amino acids encoded by the inserted genomic DNA of a human CD274 gene. The drug selection cassette is removed in a development-dependent manner, i.e., progeny derived from mice whose germ line cells containing the humanized CD274 gene described above will shed the selectable marker from differentiated cells during development.

Although embodiments employing a humanized CD274 gene in a mouse (i.e., a mouse with a CD274 gene that encodes a PD-L1 polypeptide that includes a human portion and a mouse portion) are extensively discussed herein, other non-human animals that comprise a humanized CD274 gene are also provided. In some embodiments, such non-human animals comprise a humanized CD274 gene operably linked to an endogenous CD274 promoter. In some certain embodiments, an endogenous CD274 promoter is an endogenous rodent promoter. In some embodiments, such non-human animals express a humanized PD-L1 polypeptide from an endogenous locus, wherein the humanized PD-L1 polypeptide comprises amino acid residues 19-238 (or 19-227 or 19-131) of a human PD-L1 polypeptide. Such non-human animals include any of those which can be genetically modified to express a PD-L1 polypeptide as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. Exemplary sequences of non-human CD274 orthologs include, e.g., chicken PD-L1 (XM_424811.3 and XP_424811.3), chimpanzee (XM_001140705.2 and XP_001140705.1), cow PD-L1 (NM_001163412.1 and NP_001156884.1), and dog PD-L1 (XM 0.541302.3 and XP_541302.3), monkey (NM_001083889.1 and NP_001077358.1), and rat (NM_001191954.1 and NP_001178883.1), which are hereby incorporated by reference. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo (see, e.g., Wilmut, I. et al., 1997, Nature 385:810-813; International Patent Application Publication Nos. WO 97/07668 and WO 97/07669).

Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a humanized CD274 gene.

A non-human animal harboring a humanized CD274 gene as described herein may also be created by randomly introducing a CD274 nucleic acid sequence into the genome of a non-human animal as a transgene. Depending upon context, cDNA or genomic human CD274 sequences may be employed. For example, intronic sequences and polyadenylation signals can be included in the transgene to increase the efficiency and level of expression of the transgene. A tissue-specific regulatory sequence(s) can be operably linked to a CD274 transgene to direct expression of a PD-L1 polypeptide to particular cell types. A constitutive promoter may be operably linked to the CD274 nucleic acid sequence so that the encoded PD-L1 polypeptide is overexpressed (i.e., expressed at a higher level and/or in tissues not observed in a wild-type non-human animal).

A transgenic founder non-human animal can be identified based upon the presence of a CD274 transgene in its genome and/or expression of PD-L1 mRNA in tissues or cells of the non-human animal. A transgenic founder non-human animal can then be used to breed additional non-human animals carrying the CD274 transgene. Moreover, transgenic non-human animals carrying a transgene encoding a human PD-L1 polypeptide, in whole or in part, can further be bred to other transgenic non-human animals carrying other transgenes (e.g., a Pdcd1, or CD80 transgene).

Transgenic non-human animals may also be produced to contain selected systems that allow for regulated or directed expression of the transgene. Exemplary systems include the Cre/loxP recombinase system of bacteriophage P1 (see, e.g., Lakso, M. et al., 1992, Proc. Natl. Acad. Sci. USA 89:6232-6236) and the FLP/Frt recombinase system of S. cerevisiae (O'Gorman, S. et al, 1991, Science 251:1351-1355). Such animals can be provided through the construction of "double" transgenic animals, e.g., by mating two transgenic animals, one containing a transgene encoding a selected polypeptide (e.g., a CD274 transgene) and the other containing a transgene encoding a recombinase (e.g., a Cre recombinase).

The non-human animals of the present invention may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired. In some embodiments, non-human animals of the present invention are prepared to further comprise one or more human or humanized genes selected from the B7 family of ligands and/or the CD28 family of receptors (e.g., Pdcd1 (PD-1), etc.). In some embodiments, non-human animals of the present invention may be prepared by introducing a targeting vector, as described herein, into a cell from a modified strain. In some embodiments, non-human animals of the present invention are prepared to further comprise a human or humanized Programmed cell death 1 (Pdcd1) gene. In some embodiments, non-human animals of the present invention comprise a humanized CD274 gene, as described herein, and genetic material from a heterologous species (e.g., humans), wherein the genetic material encodes, in whole or in part, one or more heterologous polypeptides selected from the B-7 family of ligands or the CD28 family of receptors. In some certain embodiments, non-human animals of the present invention comprise a humanized CD274 gene as described herein and genetic material from a heterologous species (e.g., humans), wherein the genetic material encodes, in whole or in part, a heterologous (e.g., human) PD-1 polypeptide. In some certain embodiments, non-human animals of the present invention further comprise a Pdcd1 gene that comprises an endogenous portion and a human portion, wherein the human portion encodes the extracellular domain of a human PD-1 polypeptide and the endogenous portion encodes the intracellular domain of an endogenous PD-1 polypeptide; in some embodiments, the human and endogenous portions are operably linked to an endogenous Pdcd1 promoter; in some embodiments, an endogenous rodent Pdcd1 promoter.

For example, as described herein, non-human animals comprising a humanized CD274 gene may further comprise (e.g., via cross-breeding or multiple gene targeting strategies) one or more modifications as described in U.S. patent application Ser. No. 14/744,592, filed Jun. 19, 2015, hereby incorporated by reference. In certain embodiments, a rodent comprising a humanized CD274 gene (i.e., exon 3, 4 and a 5' portion of exon 5 of a human CD274 gene operably linked to exon 1, 2, a 3' portion of exon 5, 6 and 7 of an endogenous rodent Cd274 gene so that the humanized CD274 gene encodes a PD-L1 polypeptide having an extracellular portion from a human PD-L1 polypeptide and an intracellular portion from a rodent PD-L1 polypeptide) is crossed to a rodent comprising a humanized Pdcd1 gene (e.g., exon 2 and a 5' portion of exon 3 of a human PDCD1 gene operably linked to exon 1, a 3' portion of exon 3, 4 and 5 of an endogenous rodent Pdcd1 gene so that the humanized Pdcd1 gene encodes a PD-1 polypeptide having an extracellular portion from a human PD-1 polypeptide and an intracellular portion from a rodent PD-1 polypeptide; see, e.g., U.S. patent application Ser. No. 14/744,592, filed Jun. 19, 2015, published as US 2015/0366174 A1, hereby incorporated by reference). In some embodiments, a humanized Pdcd1 gene comprises non-human (e.g., rodent) Pdcd1 exons 1, 4 and 5, a human Pdcd1 exon 2 and a Pdcd1 exon 3, which Pdcd1 exon 3 comprises a human portion and a non-human portion, and wherein said non-human and human exons are operably linked. In some embodiments, a human portion of a Pdcd1 exon 3 includes nucleotides that encode a PD-1 stalk sequence. In some embodiments, a human portion of a Pdcd1 exon 3 includes about 71 bp of a human Pdcd1 exon 3. In some embodiments, a non-human portion of a Pdcd1 exon 3 includes nucleotides that encode a transmembrane sequence. In some embodiments, a non-human portion of a Pdcd1 exon 3 includes about 91 bp of a rodent Pdcd1 exon 3. In specific embodiments, a humanized Pdcd1 gene encodes a humanized PD-1 polypeptide that includes an extracellular portion (e.g., substantially the entire extracellular domain) from a human PD-1 polypeptide, a transmembrane portion (e.g., substantially the entire transmembrane domain), and an intracellular portion (e.g., (e.g., substantially the entire intracellular domain) from a rodent PD-1 polypeptide.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rates, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, a non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 12955, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized CD274 Genes

CD274 mutant and transgenic non-human animals (e.g., mice) and cells have been reported (Iwai, Y. et al., 2002, Proc. Nat. Acad. Sci. 99(19):12293-12297; Latchman, Y. E. et al., 2004, Proc. Nat. Acad. Sci. 101(29):10691-10696; Subudhi, S. K. et al., 2004, J. Clin. Invest. 113(5):694-700; Guleria, I. et al., 2005, J. Exp. Med. 202(2):231-237; Keir, M. E. et al., 2006, J. Exp. Med. 203(4):883-895; Tanaka, K. et al., 2007, J. Immunol. 179:5204-5210; Wang, C. et al., 2008, Diabetes 57:1861-1869; Wen, X. et al., 2008, Transplant. 86(11):1596-1602; Plege, A. et al., 2009, Transpl. 87(7):975-982; Cao, Y. et al., 2010, Cancer Res. 71(4):1235-1243; Plege, A. et al., 2010, Eur. Soc. Organ Transplant. 23:1293-1300; Ritprajak, P. et al., 2010, J. Immunol. 184: 4918-4925; Yantha, J. et al., 2010, Diabetes 59:2588-2596; Ding, Q. et al., 2011, J. Leukocyte Biol. 90:77-86; Tang, L. et al., 2011, Xi Bao Yu Fen Zi Mian Yi Xue Za Zhi 27(4):357-359; Ghazizadeh, S. et al., 2012, 20(1):196-203). Such mutant and transgenic animals have been useful in determining the molecular aspects of PD-L1 expression and function, and the role of the PD-1:PD-L1 pathway in regulating immune responses, in particular, T cell responses. However, they have come with limitations that are based, in part, on the demonstrated variability in the results obtained. Many transgenic PD-L1 animals have employed the use of transgenes designed to overexpress endogenous PD-L1 (see, e.g., Ghazizadeh et al., supra), while others have focused on linking transgenic PD-L1 expression to tissue-specific promoters (see, e.g., Ritprajak et al., supra). Some of these animals have displayed expression patterns of transgenic PD-L1 that do not correlate wild-type transcription profiles (see, e.g., Wang et al. and Yantha et al., supra). Further, due to the use of the same source genetic material (e.g., mouse PD-L1 transgene in a mouse), PD-L1 overexpression may have corresponded to endogenous PD-L1 rather than transgenic PD-L1 due to possible position effects of the transgene. In some cases, such animals have demonstrated an accelerated development of disease and, therefore, raise concern that the transgene may have possibly created or modified one or more phenotypes, thereby complicating analysis of PD-L1 function. These results may reasonably be attributed to construct design. In the context of human PD-L1, pig intestinal endothelial cells engineered to stably express a CMV-driven human PD-L1 have been employed in a miniature swine skin transplantation model and provided important insights in ectopic human PD-L1 expression in an allograft model (Ding et al., supra). Existing PD-L1 transgenic non-human animals have proved useful in elucidating some biological function of PD-L1 and of the PD-1:PD-L1 pathway, however, as demonstrated above, current in vivo systems exploiting PD-L1-mediated biology are incomplete. The molecular aspects of the PD-1:PD-L1 pathway and its role in the regulation of immune responses in the context of cancer and autoimmunity have not been exploited in transgenic animals (e.g., mice) to its fullest potential.

Non-human animals of the present invention provide an improved in vivo system and source of biological materials (e.g., cells) expressing human (or humanized) PD-L1 that are useful for a variety of assays. In various embodiments, non-human animals of the present invention are used to develop therapeutics that target PD-L1 and/or modulate PD-1:PD-L1 signaling (e.g., interfering with interactions with PD-1) and/or modulate PD-L1 interactions with other binding partners (e.g., B7-1). Such animals are particularly useful as they are fully immunocompetent in contrast to many other animal models used for in vivo studies; thus, analysis of effect of therapies is not complicated by compromised immune status. In various embodiments, non-human animals of the present invention are used to identify, screen and/or develop candidate therapeutics (e.g., antibodies) that bind human PD-L1. In various embodiments, non-human animals of the present invention are used to screen and develop candidate therapeutics (e.g., antibodies) that block interaction of human PD-L1 with human PD-1 and/or human B7-1. In various embodiments, non-human animals of the present invention are used to determine the binding profile of antagonists and/or agonists of a humanized PD-L1 polypeptide on the surface of a cell of a non-human animal as described herein; in some embodiments, non-human animals of the present invention are used to determine the epitope or epitopes of one or more candidate therapeutic antibodies that bind human PD-L1.

In various embodiments, non-human animals of the present invention are used to determine the pharmacokinetic profiles of anti-PD-L1 antibodies. In various embodiments, one or more non-human animals of the present invention and one or more control or reference non-human animals are each exposed to one or more candidate therapeutic anti-PD-L1 antibodies at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebro ventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals of the present invention are used to measure the therapeutic effect of blocking or modulating PD-L1 signaling (or PD-1:PD-L1 signaling, or PD-L1:B7-1 mediated interactions) and the effect on gene expression as a result of cellular changes. In various embodiments, a non-human animal of the present invention or cells isolated therefrom are exposed to a candidate therapeutic that binds a humanized PD-L1 polypeptide (or a human portion of a PD-L1 polypeptide) on the surface of a cell of the non-human animal and, after a subsequent period of time, analyzed for effects on PD-L1-dependent processes (or interactions), for example, adhesion, apoptosis, cytokine production, inflammation, proliferation, self-tolerance and viral infection (or responses).

Non-human animals of the present invention express humanized PD-L1 polypeptide, thus cells, cell lines, and cell cultures can be generated to serve as a source of humanized PD-L1 for use in binding and functional assays, e.g., to assay for binding or function of a PD-L1 antagonist or agonist, particularly where the antagonist or agonist is specific for a human PD-L1 sequence or epitope or, alternatively, specific for a human PD-L1 sequence or epitope that associates with PD-1 and/or B7-1. In various embodiments, PD-L1 epitopes bound by candidate therapeutic antibodies can be determined using cells isolated from non-human animals of the present invention.

In various embodiments, a humanized PD-L1 polypeptide expressed by a non-human animal as described herein may comprise a variant amino acid sequence. Exemplary human PD-L1 polypeptide variants include those listed in the SNP GeneView webpage from NCBI and are summarized in Table 3. In various embodiments, non-human animals of the present invention express a humanized PD-L1 polypeptide variant. In various embodiments, the variant is polymorphic at an amino acid position associated with ligand binding. In various embodiments, non-human animals of the present invention are used to determine the effect of ligand binding through interaction with a polymorphic polypeptide variant of human PD-L1. In some certain embodiments, non-human animals of the present invention express a human PD-L1 polypeptide variant that appears in Table 3.

TABLE 3

| Chromosome position | mRNA position | Variant ID No. | Allele | Amino Acid | Codon position | Amino acid position |
|---|---|---|---|---|---|---|
| 5456116 | 111 | rs111401207 | A | I | 3 | 1 |
|  |  |  | G | M | 3 | 1 |
| 5456126 | 121 | rs139709512 | C | P | 1 | 5 |
|  |  |  | G | A | 1 | 5 |
| 5456128 | 123 | rs577786663 | C | A | 3 | 5 |
|  |  |  | T | A | 3 | 5 |
| 5456131 | 126 | rs545701711 | G | V | 3 | 6 |
|  |  |  | C | V | 3 | 6 |
| 5462841 | 168 | rs561746087 | T | Y | 3 | 20 |
|  |  |  | C | Y | 3 | 20 |
| 5462844 | 171 | rs138119378 | T | N | 3 | 21 |
|  |  |  | C | N | 3 | 21 |
| 5462876 | 203 | rs17718883 | G | R | 2 | 32 |
|  |  |  | C | P | 2 | 32 |
| 5462881 | 208 | rs140045210 | T | S | 1 | 34 |
|  |  |  | A | T | 1 | 34 |
| 5462893 | 220 | rs367921713 | A | K | 1 | 38 |
|  |  |  | G | E | 1 | 38 |
| 5462919 | 246 | rs565831052 | T | Y | 3 | 46 |
|  |  |  | C | V | 3 | 46 |
| 5462929 | 256 | rs146495642 | A | K | 1 | 50 |
|  |  |  | G | E | 1 | 50 |
| 5462931 | 258 | rs.181557130 | G | E | 3 | 50 |
|  |  |  | A | E | 3 | 50 |
| 5462952 | 279 | rs201730760 | T | D | 3 | 57 |
|  |  |  | C | D | 3 | 57 |
| 5462964 | 291 | rs569746752 | A | L | 3 | 61 |
|  |  |  | G | L | 3 | 61 |
| 5462979 | 306 | rs200229222 | T | T | 3 | 66 |
|  |  |  | C | T | 3 | 66 |
| 5462984 | 311 | rs555485716 | T | I | 2 | 68 |
|  |  |  | C | T | 2 | 68 |
| 5462988 | 315 | rs199878088 | C | N | 3 | 69 |
|  |  |  | T | N | 3 | 69 |
| 5462997 | 324 | rs41280721 | C | S | 3 | 72 |

TABLE 3-continued

| Chromosome position | mRNA position | Variant ID No. | Allele | Amino Acid | Codon position | Amino acid position |
|---|---|---|---|---|---|---|
| | | | A | R | 3 | 72 |
| 5463108 | 435 | rs376339401 | G | E | 3 | 109 |
| | | | A | E | 3 | 109 |
| 5465514 | 464 | rs61752860 | T | L | 2 | 119 |
| | | | A | H | 2 | 119 |
| 5465530 | 480 | rs372727420 | A | R | 3 | 124 |
| | | | G | R | 3 | 124 |
| 5465594 | 544 | rs568608390 | T | C | 1 | 146 |
| | | | C | R | 1 | 146 |
| 5465595 | 545 | rs148141792 | A | H | 2 | 146 |
| | | | G | R | 2 | 146 |
| 5466785 | 572 | rs141978642 | A | E | 2 | 155 |
| | | | T | V | 7 | 155 |
| 5467847 | 624 | rs150697452 | C | H | 3 | 172 |
| | | | T | H | 3 | 172 |
| 5467858 | 635 | rs369350813 | T | M | 2 | 176 |
| | | | C | T | 2 | 176 |
| 5467859 | 636 | rs373167098 | A | T | 3 | 176 |
| | | | G | T | 3 | 176 |

Cells from non-human animals of the present invention can be isolated and used on an ad hoc basis, or can be maintained in culture for many generations. In various embodiments, cells from a non-human animal of the present invention are immortalized (e.g., via use of a virus) and maintained in culture indefinitely (e.g., in serial cultures).

In various embodiments, cells and/or non-human animals of the present invention are used in various immunization regimens to determine the PD-L1-mediated functions in the immune response to an antigen (e.g., a T cell response). In some embodiments, candidate therapeutics that bind, or block one or more functions of, human (or humanized) PD-L1 are characterized in a non-human animal of the present invention. Suitable measurements include various cellular assays, proliferation assays, serum immunoglobulin analysis (e.g., antibody titer), cytotoxicity assays, characterization of ligand-receptor interactions (e.g., immunoprecipitation assays) and characterization of ligand-ligand interactions. In some embodiments, non-human animals of the present invention are used to characterize the PD-L1-mediated functions regulating an immune response to an antigen. In some embodiments, the antigen is associated with an autoimmune disease, disorder or condition. In some embodiments, the antigen is associated with an inflammatory disease, disorder or condition. In some embodiments, that antigen is associated with a neoplasm. In some embodiments, the antigen is associated with an infectious agent (e.g., a bacterium). In some embodiments, the antigen is a test antigen (e.g., ovalbumin or OVA). In some embodiments, the antigen is a target associated with a disease or condition suffered by one or more human patients in need of treatment.

In various embodiments, non-human animals of the present invention are used in serum assays for determining titers of autoantibody production for testing the pharmaco-toxicological aspects of candidate therapeutics that target human PD-L1. In some embodiments, autoantibody production in non-human animals of the present invention results from one or more autoimmune diseases, disorders or conditions induced in the non-human animal.

In various embodiments, non-human animals of the present invention are used for challenge with one or more antigens to determine the therapeutic potential of compounds or biological agents to modulate PD-L1-dependent regulation of an immune response, including but not limited to, the specific T cell-dependent and B cell-dependent responses to a given antigen.

In various embodiments, cells and/or non-human animals of the present invention are used in a survival and/or proliferation assay (e.g., employing B or T cells) to screen and develop candidate therapeutics that modulate human PD-L1 signaling. Activation or inhibition of PD-L1 plays an important role in the regulation of T cell responses, and regulation of self-tolerance by PD-L1 may result from the activation of specific epitopes of the extracellular domain of PD-L1, therefore, candidate PD-L1 modulators (e.g., antagonists or agonists) may be identified, characterized and developed using cells of non-human animals of the present invention and/or a non-human animal as described herein. In some embodiments, cells and/or non-human animals of the present invention are used in survival or death assay(s) to determine the effect on proliferation or apoptosis of a specific cell(s) (e.g., cancer cells) in the presence and absence of PD-L1.

In various embodiments, cells and/or non-human animals of the present invention are used in xenotransplantation of heterologous (e.g., human) cells or tissue to determine the PD-L1-mediated functions in the physiological (e.g., immune) response to the transplanted human cells or tissue. In some embodiments, candidate therapeutics that bind, or block one or more functions of, human PD-L1 are characterized in a non-human animal of the present invention. Suitable measurements include various cellular assays, proliferation assays, serum immunoglobulin analysis (e.g., antibody titer), cytotoxicity assays, and characterization of ligand-receptor interactions (immunoprecipitation assays).

In some embodiments, non-human animals of the present invention are used to characterize the PD-L1-mediated functions regulating an immune response to an antigen. In some embodiments, the antigen is associated with a neoplasm. In some embodiments, the antigen is associated with an autoimmune disease, disorder or condition. In some embodiments, the antigen is associated with an inflammatory disease, disorder or condition. In some embodiments, the antigen is a target associated with a disease or condition suffered by one or more human patients in need of treatment.

In various embodiments, non-human animals of the present invention are used in transplantation or adoptive transfer experiments to determine the therapeutic potential of compounds or biological agents to modulate PD-L1-dependent regulation of xenogenic lymphocytes and their immune function. In various embodiments, non-human animals of the present invention are transplanted with human T cells; in some embodiments, naïve T cells; in some embodiments, activated T cells.

In various embodiments, cells of non-human animals of the present invention are used in T cell assays to determine the therapeutic potential of compounds or biological agents to modulate PD-L1-dependent regulation of T cell-dependent response and function. Exemplary T cell assays include, but are not limited to, ELISpot, intracellular cytokine staining, major histocompatibility complex (MHC) restriction, viral suppression assays, cytotoxicity assays, proliferation assays and regulatory T cell suppression assays.

In various embodiments, cells of non-human animals of the present invention are used in cell transmigration assays to screen and develop candidate therapeutics that modulate human PD-L1. Cell transmigration involves the migration of cells across the endothelium and transmigration assays permit the measurement of interactions with, and transmigration of, the endothelium by leukocytes or tumor cells.

In various embodiments, cells of non-human animals of the present invention are used in tumor cell growth (or proliferation) assays to determine the therapeutic potential of compounds or biological agents to modulate PD-L1-dependent regulation and/or apoptosis of tumor cells.

In various embodiments, cells of non-human animals of the present invention are used in cytokine production assays to determine the therapeutic potential of compounds or biological agents to modulate PD-L1-dependent regulation of cytokine release from T cells (e.g., interferon-γ, interleukin-10). In some embodiments, cells of non-human animals of the present invention are used for detection (and/or measurement) of intracellular cytokine release resulting from interaction of humanized PD-L1 with a drug targeting human PD-L1 or a PD-L1 binding partner (e.g., PD-1, B7-1, or a soluble version thereof).

In various embodiments, an autoimmune disease, disorder or condition is induced in one or more non-human animals of the present invention to provide an in vivo system for determining the therapeutic potential of compounds or biological agents to modulate PD-L1-dependent regulation of one or more functions (or aspects) of the autoimmune disease, disorder or condition. Exemplary autoimmune diseases, disorders or conditions that may be induced in one or more non-human animals of the present invention include diabetes, experimental autoimmune encephalomyelitis (e.g., a model for multiple sclerosis), rheumatoid arthritis, and systemic lupus erythematosus.

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition and/or one or more symptoms of a disease or condition. In some embodiments, the vaccine targets a virus such as, for example, human immunodeficiency virus or hepatitis virus (e.g. HCV). Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals of the present invention provide improved in vivo system for elucidating mechanisms of human cell-to-cell interaction through adoptive transfer. In various embodiments, non-human animals of the present invention may by implanted with a tumor xenograft, followed by a second implantation of tumor infiltrating lymphocytes which could be implanted in the non-human animals by adoptive transfer to determine the effectiveness in eradication of solid tumors or other malignancies. Such experiments may be done with human cells due to the exclusive presence of human PD-L1 without competition with endogenous PD-L1 of the non-human animal. Further, therapies and pharmaceuticals for use in xenotransplantation can be improved and/or developed in such non-human animals.

Non-human animals of the present invention provide an in vivo system for assessing the pharmacokinetic properties of a drug targeting human PD-L1. In various embodiments, a drug targeting human PD-L1 may be delivered or administered to one or more non-human animals of the present invention, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, but not limited to, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs (e.g., PD-L1 modulators) are monitored in or through the use of non-human animals of the present invention.

Non-human animals of the present invention provide an in vivo system for assessing the on-target toxicity of a drug targeting human PD-L1. In various embodiments, a drug targeting human PD-L1 may be delivered or administered to one or more non-human animals of the present invention, followed by monitoring of or performing one or more assays on the non-human animals (or cells isolated therefrom) to determine the on-target toxic effect of the drug on the non-human animal. Typically, drugs are intended to modulate one or more functions of their targets. To give but one example, a PD-L1 modulator is intended to modulate PD-L1-mediated functions (e.g., PD-L1 signaling and/or PD-L1 interactions) through interacting in some way with the PD-L1 molecule on the surface of one or more cells and, in some embodiments, blocking interactions with one or more PD-L1 binding partners. In some embodiments, such a modulator may have an adverse effect that is an exaggeration of the desired pharmacologic action(s) of the modulator. Such effects are termed on-target effects. Exemplary on-target effects include too high of a dose, chronic activation/inactivation, and correct action in an incorrect tissue. In some embodiments, on-target effects of a drug targeting PD-L1 identified in or through the use of non-human animals of the present invention are used to determine a previously unknown function(s) of PD-L1.

Non-human animals of the present invention provide an in vivo system for assessing the off-target toxicity of a drug targeting human PD-L. In various embodiments, a drug targeting human PD-L1 may be delivered or administered to one or more non-human animals of the present invention, followed by monitoring of or performing one or more assays on the non-human animals (or cells isolated therefrom) to determine the off-target toxic effect of the drug on the non-human animal. Off-target effects can occur when a drug interacts with an unintended target (e.g., cross-reactivity to a common epitope). Such interactions can occur in an intended or unintended tissue. To give but one example, mirror image isomers (enantiomers) of a drug can lead to off-target toxic effects. Further, a drug can inappropriately interact with and unintentionally activate different receptor subtypes. Exemplary off-target effects include incorrect activation/inhibition of an incorrect target regardless of the tissue in which the incorrect target is found. In some embodiments, off-target effects of a drug targeting human PD-L1 are determined by comparing the effects of administering the drug to non-human animals of the present invention to one or more reference non-human animals.

In some embodiments, performing an assay includes determining the effect on the phenotype and/or genotype of the non-human animal to which the drug is administered. In some embodiments, performing an assay includes determining lot-to-lot variability for a PD-L1 modulator (e.g., an antagonist or an agonist) or a drug targeting PD-L1. In some embodiments, performing an assay includes determining the differences between the effects of a drug targeting PD-L1 administered to a non-human animal of the present invention and a reference non-human animal. In various embodiments, reference non-human animals may have a modification as described herein, a modification that is different as described herein (e.g., one that has a altered, disrupted, deleted, inserted, modified, etc. or otherwise non-functional CD274 gene) or no modification (i.e., a wild-type non-human animal).

Exemplary parameters that may be measured in non-human animals (or in and/or using cells isolated therefrom) for assessing the pharmacokinetic properties, on-target toxicity, and/or off-target toxicity of a drug targeting human PD-L1 include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity and the like. In various embodiments, non-human animals of the present invention are used to determine a pharmaceutically effective dose of a PD-L1 modulator (e.g., a drug targeting PD-L1).

Non-human animals of the present invention provide an improved in vivo system for development and characterization of candidate therapeutics for use in cancer. In various embodiments, non-human animals of the present invention may be implanted with a tumor (or tumor cells), followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of two or more mono-specific antibodies dosed sequentially or simultaneously. The tumor may be allowed sufficient time to be established in one or more locations within the non-human animal prior to administration of one or more candidate therapeutics. Tumor cell proliferation, growth, survival, etc. may be measured both before and after administration with the candidate therapeutic(s). Cytoxicity of candidate therapeutics may also be measured in the non-human animal as desired.

Non-human animals of the present invention provide an improved in vivo system for development and characterization of candidate therapeutics for use in infectious diseases. In various embodiments, non-human animals of the present invention may be infected by injection with a virus (e.g., MHV, HIV, HCV, etc.) or pathogen (e.g., bacteria), followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of two or more mono-specific antibodies dosed sequentially or simultaneously; in some embodiments, candidate therapeutics may include a vaccine. The virus or pathogen may be allowed sufficient time to be established in one or more locations or cells within the non-human animal so that one or more symptoms associated with infection of the virus or pathogen develop in the non-human animal. T cell proliferation and growth may be measured both before and after administration with the candidate therapeutic(s). Further, survival, serum and/or intracellular cytokine analysis, liver and/or spleen histopathology may be measured in non-human animals infected with the virus or pathogen. In some embodiments, non-human animals of the present invention are used to determine the extent of organ damage associated with viral infection. In some embodiments, non-human animals of the present invention are used to determine the cytokine expression profile and/or gene expression profile in various organs of non-human animals infected with a particular virus.

Non-human animals of the present invention can be employed to assess the efficacy of a therapeutic drug targeting human cells. In various embodiments, one or more non-human animals of the present invention is transplanted with human cells, and a drug candidate targeting such human cells is administered to such non-human animal. The therapeutic efficacy of the drug is then determined by monitoring the human cells in the non-human animal after the administration of the drug. Drugs that can be tested in the non-human animals include both small molecule compounds, i.e., compounds of molecular weights of less than 1500 kD, 1200 kD, 1000 kD, or 800 daltons, and large molecular compounds (such as proteins, e.g., antibodies), which have intended therapeutic effects for the treatment of human diseases and conditions by targeting (e.g., binding to and/or acting on) human cells.

In some embodiments, the drug is an anti-cancer drug, and the human cells are cancer cells, which can be cells of a primary cancer or cells of cell lines established from a primary cancer. In some embodiments, a non-human animal of the present invention is transplanted with human cancer cells, and an anti-cancer drug is given to the non-human animal. Drug efficacy can be determined by assessing whether growth or metastasis of the human cancer cells in the non-human animal is inhibited as a result of the administration of the drug.

In specific embodiments, the anti-cancer drug is an antibody molecule, which binds an antigen on human cancer cells. In particular embodiments, the anti-cancer drug is a bi-specific antibody that binds to an antigen on human cancer cells, and to an antigen on other human cells, for example, cells of the human immune system (or "human immune cells") such as B cells and T cells.

EXAMPLES

The following examples are provided so as to describe to those of ordinary skill in the art how to make and use

Example 1. Humanization of an Endogenous Cluster of Differentiation 274 (CD274) Gene This example illustrates exemplary methods of humanizing an endogenous CD274 gene encoding Programmed cell death-ligand 1 (PD-L1) in a non-human animal such as a rodent (e.g., a mouse). The methods described in this example can be employed to humanize an endogenous CD274 gene of a non-human animal using any human sequence, or combination of sequences (or sequence fragments) as desired. In this example, an ~8,444 bp human DNA fragment containing exon 3, 4 and 5 (in part) of a human CD274 gene that appears in Genbank accession NM_014143.3 (SEQ ID NO:11) is employed for humanizing an endogenous Cd274 gene of a mouse. A targeting vector for humanization of the genetic material encoding the extracellular domain, which includes an N-terminal IgV domain and an IgC2-type domain, of an endogenous Cd274 gene was constructed using VELOCIGENE® technology (see, e.g., U.S. Pat. No. 6,586,251 and Valenzuela et al., 2003, Nature Biotech. 21(6):652-659; herein incorporated by reference).

Briefly, mouse bacterial artificial chromosome (BAC) clone RP23-467A9 (Invitrogen) was modified to delete the coding sequences of exons 3, 4 and 5 (in part) of an endogenous mouse Cd274 gene (~8942 bp) and insert exons 3, 4 and 5 (in part) of a human CD274 gene using an ~8444 bp human DNA fragment, which encodes amino acids 19-238 of a human PD-L1 polypeptide. Endogenous DNA containing exon 1, exon 2, exon 6 and exon 7 as well as the untranslated regions (UTRs) were retained. Sequence analysis of the ~8,444 bp human DNA fragment confirmed that all human CD274 exons (i.e., exons 3, 4 and 5 in part) and splicing signals. Sequence analysis revealed that the sequence matched the human CD274 transcript NM014143.3. First, the ~8,444 bp human DNA fragment was amplified in two portions (FIG. 2, top). A 5' portion (~4,494 bp) containing a human CD274 exon 2 and part of intron 3 was amplified by PCR using a 3' primer that contained an NheI restriction site and a 5' primer containing a mouse homology box to facilitate bacterial homologous recombination. A 3' portion (~3,950 bp) containing part of intron 3, exon 4, intron 4 and part of exon 5 (~32 bp) was amplified by PCR using a 5' primer that contained an XhoI restriction site and a 3' primer containing a mouse homology box to facilitate bacterial homologous recombination. The PCR products were gel purified and separately digested with the corresponding restriction endonucleases. The NheI-XhoI restriction sites were employed to ligate the ~4,494 bp and ~3,950 bp DNA fragments to the 5' and 3' ends of a ~4,996 bp self-deleting neomycin cassette (loxP-hUb1-em7-Neo-pA-mPrm1-Crei-loxP; see U.S. Pat. Nos. 8,697,851, 8,518,392 and 8,354,389, all of which are hereby incorporated by reference) in reverse orientation to the DNA fragments containing human CD274 coding sequence. Subsequent selection employed neomycin. By design, the junction between the portion of human CD274 exon 5 (i.e., initial 32 bp) and endogenous Cd274 exon 5 preserved the open reading frame in exon 5 (FIG. 2) and created a unique CD274 exon 5 (AACTACCTCTGGCACATCCTCCAAAT-GAAA GGACTCACTG GGTGCTTCTG GGATCCATCC TGTTGTTCCT CATTGTAGTG TCCACGGTCC TCCTCTTCTT GAGAAAACAA G; SEQ ID NO:12). The resulting targeting vector contained, from 5' to 3', a 5' homology arm containing ~92.9 kb of mouse genomic DNA from BAC clone RP23-467A9, a ~4,494 bp human DNA fragment containing exon 3 and part of intron 3 of a human CD274 gene, a self-deleting neomycin cassette flanked by loxP sites, a ~3950 bp human DNA fragment containing part of intron 3, exon 4, intron 4 and the first 32 bp of exon 5 of a human CD274 gene, and ~67.6 kb of mouse genomic DNA from BAC clone RP23-467A9.

Figure 3:
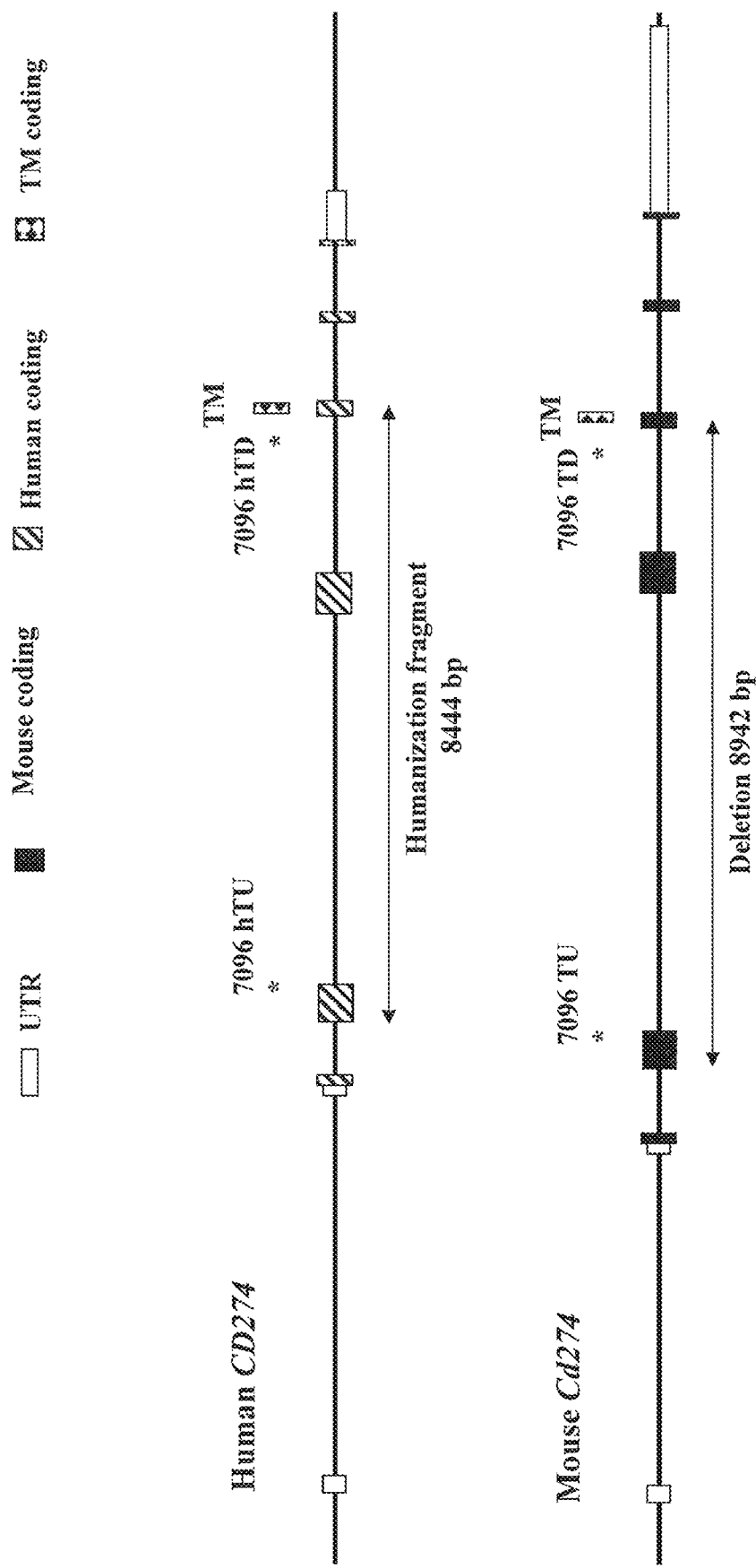
FIG. 3 shows a diagram, not to scale, of the genomic organization of a non-human (e.g., mouse) and human cluster of differentiation 274 (CD274) genes indicating the approximate locations of probes used in an assay described in Example 1. Also illustrated are an exemplary humanization fragment (humanization fragment E; SEQ ID NO:11) within a human CD274 gene and an exemplary deletion of a portion of a mouse Cd274 gene.

The modified RP23-467A9 clone described above was used to electroporate mouse embryonic stem (ES) cells to create modified ES cells comprising an endogenous CD274 gene that is humanized from exon 3 through to part of exon 5 (i.e., a deletion of ~8,964 of the endogenous Cd274 gene and insertion of ~8,444 bp of human CD274 sequence). Positively targeted ES cells containing a humanized CD274 gene were identified by an assay (Valenzuela et al., supra) that detected the presence of human CD274 sequences (e.g., exon 3, 4 and part of exon 5) and confirmed the deletion and/or retention of mouse Cd274 sequences (e.g., exon 3, 4 and part of 5 and/or exon 1, 2, 6 and 7). Table 4 sets forth exemplary sequences of primers and probes that were used to confirm humanization of an endogenous mouse Cd274 gene as described above (illustrated in FIG. 3).

Nucleotide sequences across various junctions are depicted in the diagrams in FIG. 2. The nucleotide sequence across the upstream insertion point included the following, which indicates endogenous mouse Cd274 sequence (contained within the parentheses below) contiguous with human CD274 sequence downstream of the insertion point: (TAACCTTTTA CCCAGGTTTT CAGATGTGTT TGGAGGAGTT TTCTGTCTTC TGAGGGCTGG TCCTCTTTCCT TTTCAGCGTT TACT) GTCAGGTTCC CAAGGACCTA TATGTGGTAG AGTATGGTAG CAATATGACA ATTGAATGCA AATTCCCAGTAGAA (SEQ ID NO:13).

The nucleotide sequence across the 5' end of the self-deleting Neomycin cassette included the following, which indicates human CD274 sequence contiguous with cassette sequence (contained within the parentheses below with an NheI restriction site italicized and a loxP sequence in bold font) downstream of the insertion point: TTTGTATTAA CTCTCTGTGA AGAAATTACC TCACAAATCT ATTGCTGTC (GC*IAGCTCGC*TACCTT AGGACCGTTA TAGTTACTAG C ATAACTTCGTATAGCATACAT-TATACGAAGTTATCCAGACATG ATAAGATACA TTGATGAGTT TGGACAAACC ACAACTAGAA TGCAGTGAAA AAAATGCTTT ATTTGTGAAA TTTGT-GATGC TATTGCTTTA TTTGTAACCA TTATAAGCTG) (SEQ ID NO:14).

The nucleotide sequence across the 3' end of the self-deleting Neomycin cassette included the following, which indicates cassette sequence (contained within the parentheses below with loxP sequence in bold font and an XhoI restriction site italicized) contiguous with human CD274 sequence downstream of the insertion point: (GTGAG-GAGGG GGGCGCCCGC GGGAGGCGCC AAAACCCGGC GCGGAGGCCA TGCAT ATAACTTCGT ATAGCATACA TTATACGAAG TTATCTCGAG) CTTGGTAAAG GAATGGAGAA TTAAGGCTCT AGATCATTAG TGGTTACACT ATAGT-ATTAG AAGTAAAAAA AAGATTATAC CAACAAAATA AGAACATGTT AATGTACTTG TAATGAATAA ACAT-GAATAA AGCTCTTATG CTATA (SEQ ID NO:15).

The nucleotide sequence across the 3' end of the human CD274 sequence included the following, which indicates human CD274 sequence contiguous with mouse Cd274 sequence (contained within the parentheses below): TTTATCTTTA GTCAGTTTGT TTTCGTTTTGT TTTGTTTTTC AGAACTACCT CTGGCACATC CTCCAAATGA AAGG (ACTCACTGGG TGCTTCTGGG ATCCATCCTG TTGTTCCTCA TTGTAGTGTC CACGGTCCTC CTCTTCTTGA GAAAACAAGG TATTTCCTCCATTG)(SEQ ID NO:16).

The nucleotide sequence across the insertion point after deletion of the neomycin cassette included the following, which indicates human genomic sequence juxtaposed with remaining cassette sequence loxP sequence (contained within the parentheses below with NheI and XhoI restriction sites italicized and loxP sequence in bold font): TCCTAGCCG TTTTGTATTA ACTCTCTGTG AAGAAATTAC CTCACAAATCT ATTGCTGTC (GCTAGCTCGCTACCTT AGGACCGTTA TAGTTACTAGCATAACTTCGT ATAGCATACATTATACGA AGTTATCTCGAG)CTTGGTAAAGGA ATGGAGAATT AAGGCTCTAGATCATTAGTGGTTACACTATAGTATTAGAAGTAAAAAAAAGATT ATACCA ACAAAATAAGAA (SEQ ID NO:17).

Positive ES cell clones were then used to implant female mice using the VELOCIMOUSE® method (see, e.g., U.S. Pat. No. 7,294,754 and Poueymirou et al., 2007, Nature Biotech. 25(1):91-99) to generate a litter of pups containing an insertion of human CD274 exon 3, 4 and part of human CD274 exon 5 into an endogenous mouse Cd274 gene. Mice bearing the humanization of exon 3, 4 and 5 in part (i.e., the ~8,444 bp human DNA fragment) of an endogenous Cd274 gene were again confirmed and identified by genotyping of DNA isolated from tail snips using an assay (Valenzuela et al., supra) that detected the presence of the human CD274 gene sequences. Pups are genotyped and cohorts of animals heterozygous for the humanized Pdcd1 gene construct are selected for characterization. Mice are also bred to homozygosity.

TABLE 4

| Name | Description | Sequence (5'-3') |
|---|---|---|
| 7096 hTU | Forward primer | CCGGCTGTTGAAGGACCAG SEQ D NO: 18 |
| | Probe | TCTCCCTGGGAAATGCTGCACTTCAG SEQ ID NO: 19 |
| | Reverse primer | TGCATCCTGCAATTTCACATCTG SEQ ID NO: 20 |
| 7096 hTD | Forward primer | ACACAGGTATCTCGCCATTCC SEQ ID NO: 21 |
| | Probe | AGCCACTCAAACTTTGGCATT SEQ ID NO: 22 |
| | Reverse primer | GGTCATCCTTGAAGTTTAGTTTAGC SEQ ID NO: 23 |
| 7096 TU | Forward primer | CAGGACGCAGGCGTTTAC SEQ ID NO: 24 |
| | Probe | CTGCATAATCAGCTACGGTGGTGCGG SEQ ID NO: 25 |
| | Reverse primer | TTCAGCGTGATTCGCTTGTAG SEQ ID NO: 26 |
| 7096 TD | Forward primer | CTGGAGTGCCCAAGAGTC SEQ ID NO: 27 |
| | Probe | CAGACATGGAAGAAACACAACCCGCAC SEQ ID NO: 28 |
| | Reverse primer | CTGCTAAGCCGCTTCTGTC SEQ ID NO: 29 |

Example 2. Expression of Humanized PD-L1 on Activated T Cells

This Example demonstrates that non-human animals (e.g., rodents) modified to contain a humanized CD274 gene according to Example 1 express a humanized PD-L1 polypeptide on the surface of activated lymphocytes. In this Example, activated T cells from wild-type mice and mice whose genome contained a humanized CD274 gene as described in Example 1 were stained with commercial anti-PD-L1 antibodies to determine the expression of PD-L1 in stimulated and unstimulated T cells.

Briefly, spleens were harvested and processed from a wild-type mouse and a mouse homozygous for an endogenous CD274 gene as described in Example 1 into single cell suspensions by mechanical dissociation. Cells were washed in media (RPMI supplemented with 10% FBS) and re-suspended at $1\times10^6$/mL and 200 µL (200,000 cells) were plated in 96-well plates. Cells in selected wells were stimulated with anti-CD3 and anti-CD28 antibodies (both at 1 µg/mL) for 72 hours. Cells were stained for FACS according to manufacturer's specifications with antibodies recognizing CD3, CD4, CD8 and human (clone MIH1, BD Biosciences) or mouse (clone 10F.9G2, eBioscience) PD-L1. Stained cells were run on LSRII flow cytometer and data was analyzed using FLOWJO™ software. $CD8^+$ T ($CD3^+CD8^+$) and $CD4^+$ T ($CD3^+CD4^+$) cells were gated and analyzed for expression of human and mouse PD-L1. Exemplary mean fluorescence intensity values are set forth in Table 5.

As shown in Table 5, mice bearing a humanized CD274 gene as described in Example 1 express a PD-L1 polypeptide that comprises a human portion and an endogenous portion on activated T cells. The human portion is detectably expressed via recognition by an antibody that is reactive to a fully human PD-L polypeptide, which antibody does not recognize a mouse PD-L1 polypeptide in wild-type mice. In contrast, the anti-mouse PD-L1 antibody clone 10F.9G2 demonstrated a high level of staining for mouse PD-L1 in wild-type mice after anti-CD3/anti-CD28 stimulation, and a marginal level of staining in humanized PD-L1 mice. This is most likely due to partial cross-reactivity to human PD-L1.

TABLE 5

| | | Mean Fluorescence Intensity | | | |
|---|---|---|---|---|---|
| | | $CD8^+$ T cells | | $CD4^+$ T cells | |
| Genotype | Sample | α-hPD-L1 | α-mPD-L1 | α-hPD-L1 | α-mPD-L1 |
| humanized CD274 | Isotype control | 78 | 84 | −55 | −52 |
| | Unstimulated | 271 | 160 | 114 | 61 |
| | Stimulated | 384 | 276 | 457 | 155 |
| wild-type | Isotype control | 64 | 64 | −58 | −39 |
| | Unstimulated | 62 | 712 | −45 | 538 |
| | Stimulated | 113 | 3174 | 22 | 2805 |

α-hPD-L1: anti-human PD-L1
α-mPD-L1: anti-mouse PD-L1

Example 3. In Vivo Efficacy of PD-L1 Modulators

This Example demonstrates that non-human animals (e.g., rodents) modified to contain a humanized CD274 gene according to Example 1 can be used in an in vivo assay to screen PD-L1 modulators (e.g., anti-PD-L1 antibodies) and determine various characteristics such as, for example, reducing tumor growth and/or killing of tumor cells. In this Example, several anti-PD-L1 antibodies are screened in mice homozygous for humanization of an endogenous CD274 gene (as described in Example 1) subcutaneously injected with MC38.ova tumor cells to determine the optimal antibody dose that promotes tumor regression and the extent to which anti-PD-L1 antibodies mediate killing of tumor cells.

Briefly, mice were divided evenly according to body weight into five treatment or control groups for Study 1 (n=5 to 8 mice per group) or randomized into seven treatment groups for Study 2 (n=5 to 6 mice). Study 1 animals were anesthetized by isoflurane inhalation and then injected subcutaneously into the right flank with $1\times10^6$ MC38.ova cells in suspension of 100 μL of DMEM (day 0). MC38.Ova (mouse colon adenocarcinoma) cells were engineered to express chicken ovalbumin in order to increase tumor immunogenicity and to allow monitoring of the T-cell immune responses to well-defined antigenic ovalbumin peptides. MC38.ova cells were also transduced with a lentiviral vector expressing full-length human PD-L1 under control of an SFFV viral promoter, and sorted for positive expression of human PD-L1 (MC38.ova/hPD-L1) by flow cytometry using an antibody specific for human PD-L1 (clone MIH1, BD Biosciences). MC38.ova cells also express a low level of endogenous mouse PD-L1. Study 1 treatment groups were intraperitoneally injected with 500 μg of either one of three anti-PD-L1 antibodies or one of two isotype control antibodies not specific for PD-L1 on days 3, 7, 10, 14, and 17. A single group of animals was left untreated. Study 2 animals were also subcutaneously implanted with $1\times10^6$ MC38.Ova/hPD-L1 cells (day 0), however, study 2 treatment groups were intraperitoneally administered with an anti-PD-L1 antibody (Ab A, Ab B, or Ab C) or control antibodies (i.e., not specific for PD-L1) at doses of 10 mg/kg or 5 mg/kg. Treatment groups were administered antibody on days 3, 7, 10, 14, and 17. Experimental dosing and treatment protocol for each study is set forth in Table 6.

TABLE 6

| Study 1 | | Study 2 | |
|---|---|---|---|
| Antibody | Dose (μg) | Antibody | Dose (mg/kg) |
| Ab A | 500 | Ab A | 10 |
| Ab B | 500 | Ab A | 5 |
| Ab C | 500 | Ab B | 10 |
| Control 1 | 500 | Ab B | 5 |
| Control 2 | 500 | Ab C | 10 |
| | | Ab C | 5 |
| | | Control 1 | 10 |

For each study, tumor volumes were monitored by caliper measurement twice per week for the duration of the experiment (17 days for Study 1, 21 days for Study 2) and percent survival was recorded at the end of each study. The number of tumor-free mice was also scored at the end of each study. Exemplary results, expressed as mean tumor volume (mm$^3$±SD), percent survival, and number of tumor-free mice, are set forth in Tables 7 and 8. Exemplary tumor growth curves are provided in FIG. 4.

TABLE 7

Study 1

| | Mean tumor volume (mm$^3$ ± SD) | | Survival (%) | | Tumor-free mice |
|---|---|---|---|---|---|
| Antibody | Days 10 | Day 17 | Day 10 | Day 17 | Day 17 |
| Ab A | 6 ± 10 | 2 ± 5 | 100 | 100 | 4/5 |
| Ab B | 16 ± 17 | 0 ± 0 | 100 | 100 | 5/5 |
| Ab C | 13 ± 14 | 0 ± 0 | 100 | 100 | 5/5 |
| Control 1 | 65 ± 27 | 148 ± 109 | 100 | 100 | 0/5 |
| Control 2 | 54 ± 44 | 80 ± 63 | 100 | 100 | 0/5 |

TABLE 8

Study 2

| | Mean tumor volume (mm$^3$ ± SD) | | | | Survival (%) | | | | Tumor-free mice | |
|---|---|---|---|---|---|---|---|---|---|---|
| | Day 10 | | Day 21 | | Day 10 | | Day 21 | | Day 21 | |
| Antibody | 10 mg/kg | 5 mg/kg | 10 mg/kg | 5 mg/kg | 10 mg/kg | 5 mg/kg | 10 mg/kg | 5 mg/kg | 10 mg/kg | 5 mg/kg |
| Ab A | 14 ± 15 | 17 ± 4 | 19 ± 922 | 108 ± 101 | 100 | 100 | 100 | 100 | 3/6 | 2/5 |
| Ab B | 18 ± 10 | 23 ± 10 | 34 ± 81 | 231 ± 238 | 100 | 100 | 100 | 100 | 5/6 | 1/5 |
| Ab C | 10 ± 8 | 25 ± 929 | 7 ± 16 | 37 ± 59 | 100 | 100 | 100 | 100 | 5/6 | 3/5 |
| Control 1 | 55 ± 37 | N/A | 534 ± 356 | N/A | 100 | N/A | 100 | N/A | 0/6 | N/A |

For Study 1, all three anti-PD-L1 antibodies were efficacious in promoting tumor regression at 500 μg/mouse with all mice from treatment groups that received Ab B and Ab C being tumor free at day 17 (Table 7). In the Ab A treatment group, four of five mice (80%) were tumor free by day 17, whereas none of the animals in the control groups were tumor-free. One-way ANOVA with Dunnett's multiple comparison post-test revealed a significant difference in tumor volumes between treatments with anti-PD-L1 antibodies and the control antibodies with a p value <0.05. Control 2 is an unrelated matched isotype control antibody, while control 1 is an unrelated unmatched isotype control antibody.

For Study 2, administration of the selected anti-PD-L1 antibodies resulted in inhibition of tumor growth and thereby promoted tumor regression (Table 8). All anti-PD-L1 antibodies tested were efficacious at 10 mg/kg and 5 mg/kg, and promoted tumor regression in treated mice in a dose dependent manner throughout the course of the experiment. None of the animals treated with control antibodies were tumor-free (Table 8). One-way ANOVA with Tukey's multiple comparison post-test revealed a significant difference in tumor volumes between treatments with the anti-PD-L1 antibodies and control antibodies with p value <0.05 or lower. Control 1 is an unrelated matched isotype control.

Figure 4:
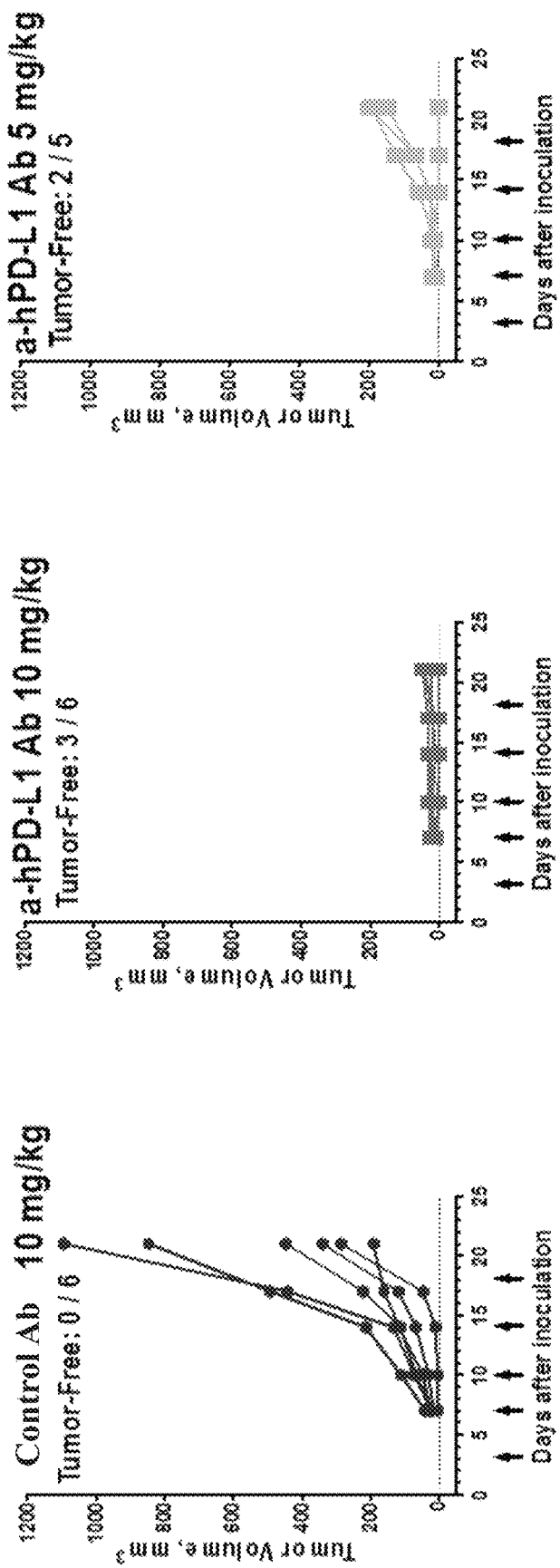
FIG. 4 shows exemplary MC38.ova/hPD-L1 tumor growth curves over 21 days in mice homozygous for humanization of an endogenous PD-L1 gene as described in Example 1. Control Ab: antibody not specific for PD-L1, a-hPD-LL: antibody specific for human PD-L1. Arrows indicate the days for antibody treatment during the experiment. The number of tumor-free mice on day 21 is shown for each treatment group.

As shown in FIG. 4 and Tables 7 and 8, anti-PD-L1 antibodies significantly inhibited tumor growth in a prophylactic MC38.ova/hPD-L1 tumor growth model in mice having a humanized CD274 gene as described in Example 1. Anti-PD-L1 antibody therapy at 10 mg/kg and 5 mg/kg promoted tumor regression in all mice throughout the course of the experiment resulting in three out of six mice remaining tumor-free in 10 mg/kg group and two out of five mice remaining tumor-free in 5 mg/kg treatment group by Day 21, whereas none of the animals remained tumor-free in the control group (0/6) (FIG. 4). One-way ANOVA with Dunnett's multiple comparison post-test revealed a significant difference in tumor volumes on Day 21 between anti-PD-L1 and control antibody treatments with a p value <0.01 (5 mg/kg treatment group) and p value <0.0001 (10 mg/kg treatment group).

In a similar experiment, intact functional PD-L1 signaling in mice containing a humanized CD274 gene as described in Example 1 was investigated by measuring $CD8^+$ and $CD3^+$ T cell responses in splenocytes of tumor-bearing mice treated with anti-PD-L1 antibody.

Briefly, splenocytes were isolated from mice containing a humanized CD274 gene as described in Example 1 treated with anti-PD-L1 or control antibody at the end of the experiment on Day 21 (described above). Total RNA was isolated, and real-time PCR was performed on reverse transcribed cDNA using oligonucleotides and TAQMAN™ probe mix specific for mouse CD8b, mouse CD3ζ (Mm00446171_m1, Applied Biosystems), human PD-L1 and mouse PD-L1 (Table 9). Samples were normalized relative to expression of mouse cyclophilin B. Exemplary results are provided in FIG. 5.

TABLE 9

| Name | Description | Sequence (5'-3') |
|---|---|---|
| mCD8b | Forward primer | GCTCTGGCTGGTCTTCAGTATG SEQ ID NO: 30 |
|  | Probe | AGCAGCTCTGCCCTCAT SEQ ID NO: 31 |
|  | Reverse primer | TTGCCGTATGGTTGGTTTGAAC SEQ ID NO: 32 |
| hPD-L1 | Forward primer | ACAGCCTGCTGTCACTTGC SEQ ID NO: 33 |
|  | Probe | TACGGGCGTTTACTGTCAC SEQ ID NO: 34 |
|  | Reverse primer | ACCACATATAGGTCCTTGGGAAC SEQ ID NO: 35 |
| mPD-L1 | Forward primer | TTCTCAATGTGACCAGCAGTC SEQ ID NO: 36 |
|  | Probe | AGGGTCAACGCCACAGCGAATGA SEQ ID NO: 37 |
|  | Reverse primer | TCCTGTTCTGTGGAGGATGTG SEQ ID NO: 38 |

Figure 5:
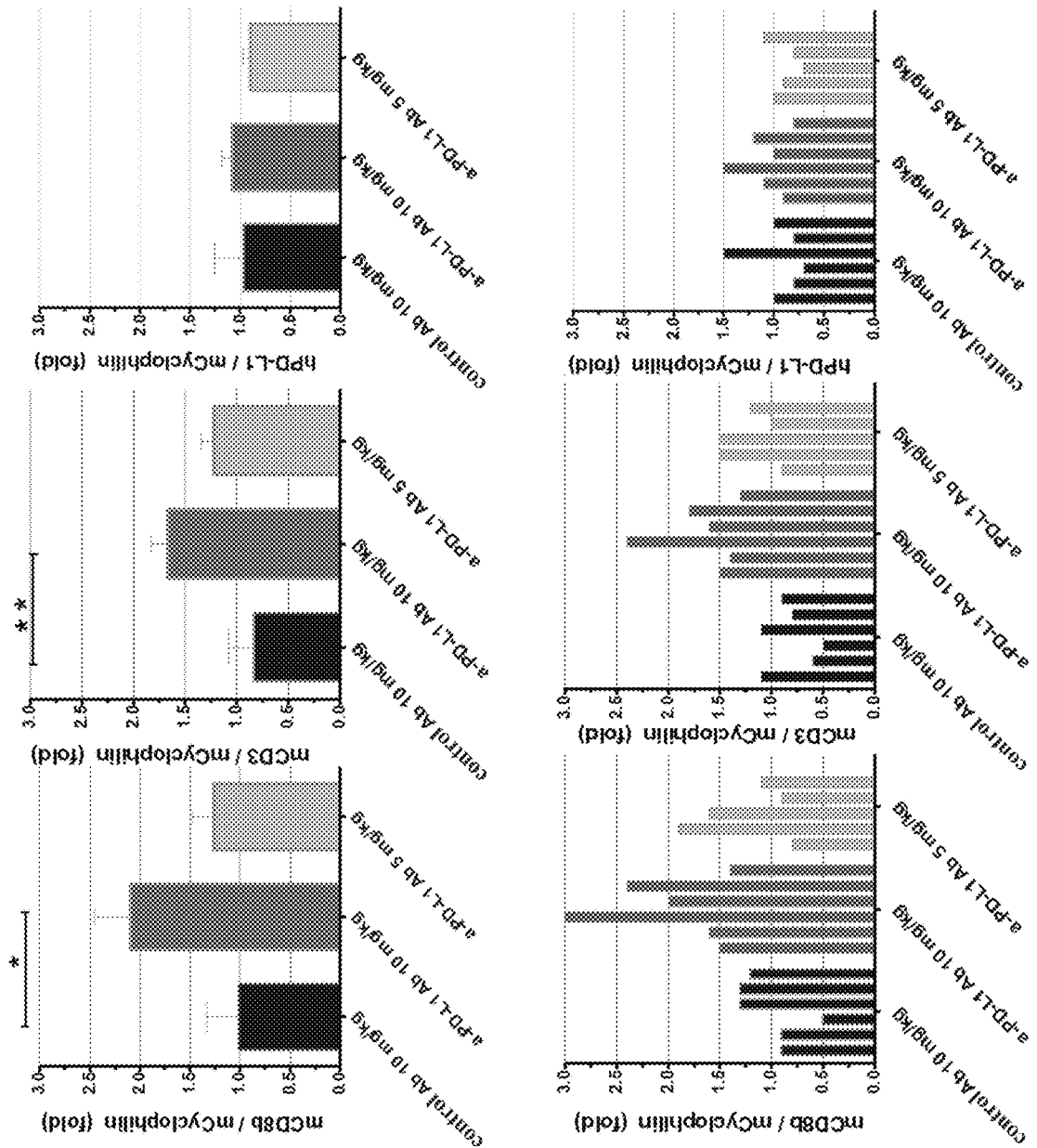
FIG. 5 shows exemplary real-time PCR analysis of CD8b, CD3 and PD-L1 mRNA expression in splenocytes of mice homozygous for an endogenous CD274 gene as described in Example 1 after treatment with anti-PD-L1 or control antibodies. A, mean of six mice per group. B, expression levels for individual mice in each treatment group. Control Ab: antibody not specific for PD-L1; a-PD-L1: anti-PD-L antibody.

As shown in FIG. 5, administration of anti-hPD-L1 antibody induced an increase in the number of $CD8^+$ and $CD3^+$ T cells in splenocytes of mice containing a humanized CD274 gene (as described in Example 1) and bearing MC38.ova/hPD-L1 tumors. This confirms that mice containing a humanized CD274 gene (as described in Example 1) demonstrate proper expression and signaling through humanized PD-L1 on the cell surface in that PD-L1 expression by MC38.ova cells was not able to suppress proliferation of anti-tumor CD8T cells. Overall, the demonstrated increase in T cells as compared to control-treated mice was observed for both treatment groups, however, statistical difference in CD8b (p value <0.01) and CD3 (p<0.001) levels using a one-way ANOVA with Dunnett's multiple comparison post-test was only reached between the 10 mg/kg anti-PD-L1 antibody and control treatment groups.

Human PD-L1 mRNA expression was measured with human specific probes designed for the extracellular portion of human PD-L1 polypeptide (Table 9) and confirmed proper expression of humanized PD-L1 protein on the cell surface (FIG. 5). Additionally, measurement of mouse PD-L1 mRNA expression with primers designed to detect the extracellular portion of mouse PD-L1 (Table 9) failed to produce a product. These data confirm the flow cytometry results presented in Table 5, i.e., humanized PD-L1 mice indeed express humanized PD-L1 that is intact and functional on the cell surface.

Taken together, this example demonstrates that non-human animals of the present invention can be used to assess the in vivo efficacy of drugs (e.g., antibodies) that target PD-L1, and such animals are useful in discriminating the therapeutic effect of anti-PD-L1 antibodies. Moreover, non-human animals described herein can be used to assess the extent to which drugs targeting PD-L1 can promote the regression of tumors and/or mediate killing of tumor cells. Non-human animals (e.g. mice) of the present invention demonstrate expression of functional humanized PD-L1 polypeptide on the cell surface and proper PD-L1 regulation of immune responses via inhibition of PD-L1-dependent suppression of $CD8^+$ T cells in a tumor model.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein. The publications, websites and other reference materials referenced herein to describe the background of the invention and to provide additional detail regarding its practice are hereby incorporated by reference.

We claim:

1. A genetically modified mouse whose genome comprises a humanized PD-L1 gene encoding a humanized PD-L1 polypeptide, and a humanized PD-1 gene encoding a humanized PD-1 polypeptide,
   wherein said humanized PD-L1 gene comprises a replacement of a nucleic acid sequence of an endogenous PD-L1 gene with a nucleic acid sequence encoding the extracellular sequence of a human PD-L1 polypeptide, and the humanized PD-L1 polypeptide comprises (i) the extracellular sequence of the human PD-L1 polypeptide and (ii) the intracellular and transmembrane sequences of a mouse PD-L1 polypeptide;
   wherein the humanized PD-1 gene comprises mouse PD-1 exon 1, human PD-1 exon 2, a 5' portion of human PD-1 exon 3, a 3' portion of mouse PD-1 exon 3, mouse PD-1 exon 4 and mouse PD-1 exon 5;
   wherein the humanized PD-1 polypeptide comprises (i) an extracellular portion of a human PD-1 polypeptide and (ii) the transmembrane and intracellular domains of a mouse PD-1 polypeptide; and
   wherein the humanized PD-L1 polypeptide and the humanized PD-1 polypeptide are expressed and functional in the mouse.

2. An isolated cell or tissue of the mouse of claim 1, wherein the isolated cell or tissue comprises the humanized PD-L1 gene and the humanized PD-1 gene in the genome.

3. The isolated cell or tissue of claim 2, wherein the humanized PD-L1 gene comprises (i) exon 1 and exon 2 of the endogenous PD-L1 gene, (ii) exon 3, exon 4, and a portion of exon 5 of a human PD-L1 gene, and (iii) exon 6, exon 7, and a portion of exon 5 of the endogenous PD-L1 gene.

4. A method of assessing the pharmacokinetic properties of a drug targeting a human PD-L1 polypeptide, the method comprising the steps of
   administering a drug targeting the human PD-L1 polypeptide to the mouse of claim 1; and
   performing an assay using a sample obtained from the mouse to determine one or more pharmacokinetic properties of the drug.

5. The method of claim 4, wherein the humanized PD-L1 gene comprises exon 6, exon 7, and a portion of exon 5 of the endogenous CD274 gene.

6. The method of claim 5, wherein the humanized CD274 gene comprises exon 1 and exon 2 of the endogenous PD-L1 gene.

7. The method of claim 6, wherein the nucleic acid sequence encoding the extracellular sequence of the human PD-L1 polypeptide comprises exon 3, exon 4, and a portion of exon 5 of a human PD-L1 gene.

* * * * *

UNITED STATES PATENT AND TRADEMARK OFFICE
CERTIFICATE OF CORRECTION

PATENT NO. : 12,089,575 B2
APPLICATION NO. : 17/110868
DATED : September 17, 2024
INVENTOR(S) : Elena Burova Page 1 of 2

It is certified that error appears in the above-identified patent and that said Letters Patent is hereby corrected as shown below:

On the Title Page

Item (57) ABSTRACT Line 8, should read:
(PD-L1) polypeptide that includes a human portion and an In the Claims Column 113, Line 28, replace Claim 1 with the following:
1. A genetically modified mouse whose genome comprises:
A) a humanized PD-L1 gene comprising a replacement of a nucleic acid sequence of an endogenous PD-L1 gene encoding an extracellular domain of a mouse PD-L1 polypeptide with a nucleic acid sequence encoding an extracellular domain of a human PD-L1 polypeptide, wherein the humanized PD-L1 gene encodes a humanized PD-L1 polypeptide comprising:
    i) the extracellular domain of the human PD-L1 polypeptide; and
    ii) the intracellular and transmembrane domains of the mouse PD-L1 polypeptide; and
B) a humanized PD-1 gene comprising mouse PD-1 exon 1, human PD-1 exon 2, a 5′ portion of human PD-1 exon 3, a 3′ portion of mouse PD-1 exon 3, mouse PD-1 exon 4, and mouse PD-1 exon 5, wherein the humanized PD-1 gene encodes a humanized PD-1 polypeptide comprising:
    i) the extracellular domain of a human PD-1 polypeptide; and
    ii) the intracellular and transmembrane domains of a mouse PD-1 polypeptide,
    wherein the mouse functionally expresses the humanized PD-L1 and PD-1 polypeptides.

Column 113, Line 50, replace Claim 2 with the following:
2. A cell or tissue isolated from the genetically modified mouse of claim 1.

Column 114, Line 27, replace Claim 3 with the following:
3. The isolated cell or tissue of claim 2, wherein the humanized PD-L1 gene comprises (i) exon 1 and exon 2 of the endogenous PD-L1 gene, (ii) exon 3, exon 4, and a portion of exon 5 of a human PD-L1 gene, and (iii) exon 6, exon 7, and a portion of exon 5 of the endogenous PD-L1 gene.

Signed and Sealed this
First Day of April, 2025

Coke Morgan Stewart
*Acting Director of the United States Patent and Trademark Office*

Column 114, Line 33, replace Claim 4 with the following:
4. A method of assessing the pharmacokinetics of a drug that binds a human PD-L1 polypeptide, the method comprising:
   a) administering the drug to the genetically modified mouse of claim 1; and
   b) analyzing the pharmacokinetics of the drug using a sample from the mouse obtained in step a).

Column 114, Line 42, replace Claim 5 with the following:
5. The method of claim 4, wherein the humanized PD-L1 gene comprises exon 6, exon 7, and a portion of exon 5 of the endogenous PD-L1 gene.

Column 114, Line 45, replace Claim 6 with the following:
6. The method of claim 5, wherein the humanized PD-L1 gene comprises exon 1 and exon 2 of the endogenous PD-L1 gene.

Column 114, Line 48, replace Claim 7 with the following:
7. The method of claim 6, wherein the nucleic acid sequence encoding the extracellular sequence of the human PD-L1 polypeptide comprises exon 3, exon 4, and a portion of exon 5 of a human PD-L1 gene.